US008642837B2

(12) United States Patent
Douwe de Boer et al.

(10) Patent No.: US 8,642,837 B2
(45) Date of Patent: *Feb. 4, 2014

(54) METHOD TO INCREASE PATHOGEN RESISTANCE IN PLANTS

(75) Inventors: Anne Douwe de Boer, Dreumel (NL); Eduard Daniel Leendert Schmidt, Oosterbeek (NL); Paul Alexandre Passarinho, Wageningen (NL)

(73) Assignee: Expressive Research B.V., Wageningen (NL)

( * ) Notice: Subject to any disclaimer, the term of this patent is extended or adjusted under 35 U.S.C. 154(b) by 271 days.

This patent is subject to a terminal disclaimer.

(21) Appl. No.: 11/699,401

(22) Filed: Jan. 29, 2007
(Under 37 CFR 1.47)

(65) Prior Publication Data
US 2008/0220971 A1  Sep. 11, 2008

Related U.S. Application Data

(63) Continuation-in-part of application No. PCT/NL2005/000540, filed on Jul. 25, 2005.

(30) Foreign Application Priority Data

Jul. 28, 2004 (EP) ..................................... 04077173

(51) Int. Cl.
*C12N 15/09* (2006.01)
*C12N 15/82* (2006.01)
*A01H 5/00* (2006.01)
*A01H 1/00* (2006.01)

(52) U.S. Cl.
USPC ........... 800/279; 800/278; 800/298; 800/301; 800/302; 435/6.1

(58) Field of Classification Search
None
See application file for complete search history.

(56) References Cited

U.S. PATENT DOCUMENTS

| 5,859,339 | A | * | 1/1999 | Ronald et al. ................. 800/279 |
| 5,986,082 | A | | 11/1999 | Ryals et al. |
| 7,838,728 | B2 | * | 11/2010 | Schmidt ......................... 800/278 |
| 2003/0041344 | A1 | * | 2/2003 | Chory et al. ................... 800/278 |
| 2006/0265783 | A1 | | 11/2006 | Schmidt |
| 2009/0138991 | A1 | | 5/2009 | Reuzeau |

FOREIGN PATENT DOCUMENTS

| EP | 1 382682 | * | 1/2004 |
| WO | WO 0210367 | * | 2/2002 |
| WO | WO 03/016551 | | 2/2003 |
| WO | WO 03016551 | * | 2/2003 |
| WO | WO 2004/007712 | | 1/2004 |

OTHER PUBLICATIONS

Fontes et al. Genes and Development (2004) 18:2545-2556.*
Shiu, et al., "Comparative Analysis of the Receptor-Like Kinase Family in Arabidopsis and Rice", The Plant Cell, 16 (5): 1220-1234, 2004, American Society of Plant Biologists.
Ziaorong Zhang, "Leucine-rich Repeat Receptor-like Kinases in Plants", Plant Molecular Biology Reporter, 16:301-311, 1998, Kluwer Academic Publishers.
Lehti-Shiu et al., Plant Physiol. 150:12-26 (2009).
Shiu et al., Plant Physiol. 132:530-543 (2003).
Schmidt et al., Development 124:2049-2062 (1997).
Cao et al., "The Arabidopsis NPR1 Gene That Controls Systemic Acquired Resistance Encodes a Novel Protein Containing Ankyrin Repeats", Cell, Cell Press, vol. 88; pp. 57-63; Jan. 1997.
Ciardi et al., "Response to Xanthomonas Campestris Pv. Vesicatoria in Tomato Involves Regulation of Ethylene Receptor Gene Expression", Plant Physiology, vol. 123:1; pp. 81-92; May 2005.
Cirardi et al., "Reduced Expression of the Tomato Ethylene Receptor Gene Leetr4 Enhances the Hypersensitive Response to Xanthomonas Campestris PV. Vesicatoria", Molecular Plant-Microbe Interactions, vol. 14:4; pp. 487-495; Apr. 2001.
Kumar et al., "High-Affinity Salicylic Acid-Binding Protein 2 is Required for Plant Innate Immunity and Has Salicylic Acid-Stimulated Lipase Activity", Proceeding of the National Academy of Sciences of the United States of America, vol. 100:26; pp. 16101-16106; Dec. 2003.
Kumar et al., "Identification of SA-Binding Protein 2 (SABP2) and its Role in Disease Resistance", Phtopatholgy, vol. 93:6; pp. S47-S48; Jun. 2003.
Nuki et al., "Transgenic Lotus Japonicus with an Ethylene Receptor Gene Cm-ERS1/H701 enhances Formation of Infection Threads and Nodule Primordia", Pkant & Cell Physiology, vol. 45:4; pp. 427-435; Apr. 2004.
Ryals et al., "Systemic Acquired Resistance", Plant Cell, American Society of Plant Physiologists, pp. 1809-1819; Oct. 1996.

* cited by examiner

Primary Examiner — Medina A Ibrahim
(74) Attorney, Agent, or Firm — Hoffmann & Baron, LLP

(57) ABSTRACT

The invention provides a method for enhancing resistance in plants by providing these plants with a gene construct comprising a DNA sequence coding for a receptor for a systemic signal compound, wherein such a systemic signal compound is one or more of the group consisting of salicylic acid, jasmonic acid and brassinosteroids. The resistance can the be induced by contacting said plants with said signal compound. Preferably, the receptor is an RKS receptor, salicylic acid receptor or jasmonic acid receptor. Also combinations and/or chimaeric receptors can be applied.

14 Claims, 17 Drawing Sheets

SEQUENCE LISTING

<160> NUMBER OF SEQ ID NOS: 28

<210> SEQ ID NO 1
<211> LENGTH: 2087
<212> TYPE: DNA
<213> ORGANISM: Arabidopsis thaliana

<400> SEQUENCE: 1

```
attttattt tatttttac tctttgtttg tttaatgct aatgggtttt taaaagggtt    60
atcgaaaaaa tgagtgagtt tgtgttgagg ttgtctctgt aaagtgttaa tggtggtgat   120
tttcggaagt tagggttttc tcggatctga agagatcaaa tcaagattcg aaatttacca   180
ttgttgtttg aaatggagtc gagttatgtg gtgtttatct tactttcact gatcttactt   240
ccgaatcatt cactgtggct tgcttctgct aatttggaag gtgatgcttt gcatactttg   300
agggttactc tagttgatcc aaacaatgtc ttgcagagct gggatcctac gctagtgaat   360
ccttgcacat ggttccatgt cacttgcaac aacgagaaca gtgtcataag agttgatttg   420
gggaatgcag agttatctgg ccatttagtt ccagagcttg gtgtgctcaa gaatttgcag   480
tatttggagc tttacagtaa caacataact ggcccgattc ctagtaatct tggaaatctg   540
acaaacttag tgagtttgga tctttactta aacagcttct ccggtcctat tccggaatca   600
ttgggaaagc tttcaaagct gagatttctc cggcttaaca caacagtct cactgggtca   660
attcctatgt cactgaccaa tattactacc cttcaagtgt tagatctatc aaataacaga   720
ctctctggtt cagttcctga caatggctcc ttctcactct tcacacccat cagttttgct   780
aataacttag acctatgtgg acctgttaca agtcacccat gtcctggatc tccccgttt   840
tctcctccac cacctttat tcaacctccc cagtttcca ccccgagtgg gtatggtata   900
actggagcaa tagctggtgg agttgctgca ggtgctgctt tgcccttgc tgctcctgca   960
atagcctttg cttggtggcg acgaagaagc ccactagata ttttcttcga tgtccctgcc  1020
gaagaagatc cagaagttca tctgggacag ctcaagaggt tttctttgcg ggagctacaa  1080
gtggcgagtg atgggtttag taacaagaac attttgggca gaggtggggtt tgggaaagtc  1140
tacaagggac gcttggcaga cggaactctt gttgctgtca agagactgaa ggaagagcga  1200
actccaggtg gagagctcca gtttcaaaca gaagtagaga tgataagtat ggcagttcat  1260
cgaaacctgt tgagattacg aggtttctgt atgacaccga ccgagagatt gcttgtgtat  1320
ccttacatgg ccaatggaag tgttgcttcg tgtctcagag agaggccacc gtcacaacct  1380
ccgcttgatt ggccaacgcg gaagagaatc gcgctaggct cagctcgagg tttgtcttac  1440
ctacatgatc actgcgatcc gaagatcatt caccgtgacg taaaagcagc aaacatcctc  1500
ttagacgaag aattcgaagc ggttgttgga gatttcgggt tggcaaagct tatggactat  1560
aaagacactc acgtgacaac agcagtccgt ggcaccatcg gtcacatcgc tccagaatat  1620
ctctcaaccg gaaaatcttc agagaaaacc gacgttttcg gatacggaat catgcttcta  1680
gaactaatca caggacaaag agctttcgat ctcgctcggc tagctaacga cgacgacgtc  1740
atgttacttg actgggtgaa aggattgttg aaggagaaga agctagagat gttagtggat  1800
ccagatcttc aaacaaacta cgaggagaga gaactggaac aagtgataca agtggcgttg  1860
ctatgcacgc aaggatcacc aatggaaaga ccaaagatgt ctgaagttgt aaggatgctg  1920
gaaggagatg ggcttgcgga gaaatgggac gaatggcaaa aagttgagat tttgagggaa  1980
gagattgatt tgagtcctaa tcctaactct gattggattc ttgattctac ttacaatttg  2040
cacgccgttg agttatctgg tccaaggtaa aaaaaaaaaa aaaaaaa      2087
```

<210> SEQ ID NO 2
<211> LENGTH: 625
<212> TYPE: PRT
<213> ORGANISM: Arabidopsis thaliana

<400> SEQUENCE: 2

-continued

```
Met Glu Ser Ser Tyr Val Val Phe Ile Leu Leu Ser Leu Ile Leu Leu
 1               5                  10                 15

Pro Asn His Ser Leu Trp Leu Ala Ser Ala Asn Leu Glu Gly Asp Ala
             20                  25                  30

Leu His Thr Leu Arg Val Thr Leu Val Asp Pro Asn Asn Val Leu Gln
             35                  40                  45

Ser Trp Asp Pro Thr Leu Val Asn Pro Cys Thr Trp Phe His Val Thr
 50                  55                  60

Cys Asn Asn Glu Asn Ser Val Ile Arg Val Asp Leu Gly Asn Ala Glu
 65                  70                  75                  80

Leu Ser Gly His Leu Val Pro Glu Leu Gly Val Leu Lys Asn Leu Gln
                 85                  90                  95

Tyr Leu Glu Leu Tyr Ser Asn Asn Ile Thr Gly Pro Ile Pro Ser Asn
             100                 105                 110

Leu Gly Asn Leu Thr Asn Leu Val Ser Leu Asp Leu Tyr Leu Asn Ser
                 115                 120                 125

Phe Ser Gly Pro Ile Pro Glu Ser Leu Gly Lys Leu Ser Lys Leu Arg
 130                 135                 140

Phe Leu Arg Leu Asn Asn Asn Ser Leu Thr Gly Ser Ile Pro Met Ser
145                 150                 155                 160

Leu Thr Asn Ile Thr Thr Leu Gln Val Leu Asp Leu Ser Asn Asn Arg
                 165                 170                 175

Leu Ser Gly Ser Val Pro Asp Asn Gly Ser Phe Ser Leu Phe Thr Pro
             180                 185                 190

Ile Ser Phe Ala Asn Asn Leu Asp Leu Cys Gly Pro Val Thr Ser His
             195                 200                 205

Pro Cys Pro Gly Ser Pro Pro Phe Ser Pro Pro Pro Phe Ile Gln
 210                 215                 220

Pro Pro Pro Val Ser Thr Pro Ser Gly Tyr Gly Ile Thr Gly Ala Ile
225                 230                 235                 240

Ala Gly Gly Val Ala Ala Gly Ala Ala Leu Pro Phe Ala Ala Pro Ala
                 245                 250                 255

Ile Ala Phe Ala Trp Trp Arg Arg Arg Lys Pro Leu Asp Ile Phe Phe
             260                 265                 270

Asp Val Pro Ala Glu Glu Asp Pro Glu Val His Leu Gly Gln Leu Lys
             275                 280                 285

Arg Phe Ser Leu Arg Glu Leu Gln Val Ala Ser Asp Gly Phe Ser Asn
             290                 295                 300

Lys Asn Ile Leu Gly Arg Gly Gly Phe Gly Lys Val Tyr Lys Gly Arg
305                 310                 315                 320

Leu Ala Asp Gly Thr Leu Val Ala Val Lys Arg Leu Lys Glu Glu Arg
             325                 330                 335

Thr Pro Gly Gly Glu Leu Gln Phe Gln Thr Glu Val Glu Met Ile Ser
             340                 345                 350

Met Ala Val His Arg Asn Leu Leu Arg Leu Arg Gly Phe Cys Met Thr
             355                 360                 365

Pro Thr Glu Arg Leu Leu Val Tyr Pro Tyr Met Ala Asn Gly Ser Val
 370                 375                 380

Ala Ser Cys Leu Arg Glu Arg Pro Pro Ser Gln Pro Pro Leu Asp Trp
385                 390                 395                 400

Pro Thr Arg Lys Arg Ile Ala Leu Gly Ser Ala Arg Gly Leu Ser Tyr
             405                 410                 415

Leu His Asp His Cys Asp Pro Lys Ile Ile His Arg Asp Val Lys Ala
             420                 425                 430
```

Ala Asn Ile Leu Leu Asp Glu Glu Phe Glu Ala Val Val Gly Asp Phe
        435                 440                 445

Gly Leu Ala Lys Leu Met Asp Tyr Lys Asp Thr His Val Thr Thr Ala
450                 455                 460

Val Arg Gly Thr Ile Gly His Ile Ala Pro Glu Tyr Leu Ser Thr Gly
465                 470                 475                 480

Lys Ser Ser Glu Lys Thr Asp Val Phe Gly Tyr Gly Ile Met Leu Leu
                485                 490                 495

Glu Leu Ile Thr Gly Gln Arg Ala Phe Asp Leu Ala Arg Leu Ala Asn
            500                 505                 510

Asp Asp Val Met Leu Leu Asp Trp Val Lys Gly Leu Leu Lys Glu
        515                 520                 525

Lys Lys Leu Glu Met Leu Val Asp Pro Asp Leu Gln Thr Asn Tyr Glu
530                 535                 540

Glu Arg Glu Leu Glu Gln Val Ile Gln Val Ala Leu Leu Cys Thr Gln
545                 550                 555                 560

Gly Ser Pro Met Glu Arg Pro Lys Met Ser Glu Val Val Arg Met Leu
                565                 570                 575

Glu Gly Asp Gly Leu Ala Glu Lys Trp Asp Glu Trp Gln Lys Val Glu
            580                 585                 590

Ile Leu Arg Glu Glu Ile Asp Leu Ser Pro Asn Pro Asn Ser Asp Trp
        595                 600                 605

Ile Leu Asp Ser Thr Tyr Asn Leu His Ala Val Glu Leu Ser Gly Pro
610                 615                 620

Arg
625

<210> SEQ ID NO 3
<211> LENGTH: 1950
<212> TYPE: DNA
<213> ORGANISM: Arabidopsis thaliana

<400> SEQUENCE: 3

```
ccaaagttga ttgctttaag aagggatatg aaggtgtga  gatttgtggt gtggagatta      60
ggatttctgg tttttgtatg gttctttgat atctcttctg ctacactttc tcctactggt     120
gtaaactatg aagtgacagc tttggttgct gtgaagaatg aattgaatga tccgtacaaa     180
gttcttgaga attgggatgt gaattcagtt gatccttgta gctggagaat ggtttcttgc     240
actgatggct atgtctcttc actggatctt cctagccaaa gcttgtctgg tacattgtct     300
cctagaatcg gaaacctcac ctatttacaa tcagtggtgt tgcaaaacaa tgcaatcact     360
ggtccaattc cggaaacgat tgggaggttg agaagcttc agtcacttga tctttcgaac     420
aattcattca ccggggagat accggcctca cttggagaac tcaagaactt gaattacttg     480
cggttaaaca ataacagtct tataggaact tgccctgagt ctctatccaa gattgaggga     540
ctcactctag tcgacatttc gtataacaat cttagtggtt cgctgccaaa gtttctgcc      600 agaactttca aggtaattgg taatgcgtta atctgtggcc caaaagctgt ttcaaactgt     660
tctgctgttc ccgagcctct cacgcttcca aagatggtc cagatgaatc aggaactcgt      720
accaatggcc atcacgttgc tcttgcattt gccgcaagct tcagtgcagc attttttgtt     780
ttctttacaa gcggaatgtt tctttggtgg agatatcgcc gtaacaagca atatttttt     840 gacgttaatg aacaatatga tccagaagtg agtttagggc acttgaagag gtatacattc     900
aaagagctta gatctgccac caatcatttc aactcgaaga acattctcgg aagaggcgga     960
```

```
tacgggattg tgtacaaagg acacttaaac gatggaactt tggtggctgt caaacgtctc    1020
aaggactgta acattgcggg tggagaagtc cagtttcaga cagaagtaga gactataagt    1080
ttggctcttc atcgcaatct cctccggctc cgcggtttct gtagtagcaa ccaggagaga    1140
attttagtct acccttacat gccaaatggg agtgtcgcat cacgcttaaa agataatatc    1200
cgtggagagc cagcattaga ctggtcgaga aggaagaaga tagcggttgg gacagcgaga    1260
ggactagttt acctacacga gcaatgtgac ccgaagatta tacaccgcga tgtgaaagca    1320
gctaacattc tgttagatga ggacttcgaa gcagttgttg gtgattttgg gttagctaag    1380
cttctagacc atagagactc tcatgtcaca actgcagtcc gtggaactgt tggccacatt    1440
gcacctgagt acttatccac gggtcagtcc tcagagaaga ctgatgtctt tggctttggc    1500
atacttctcc ttgagctcat tactggtcag aaagctcttg attttggcag atccgcacac    1560
cagaaaggtg taatgcttga ctgggtgaag aagctgcacc aagaagggaa actaaagcag    1620
ttaatagaca aagatctaaa tgacaagttc gatagagtag aactcgaaga aatcgttcaa    1680
gttgcgctac tctgcactca attcaatcca tctcatcgac cgaaaatgtc agaagttatg    1740
aagatgcttg aaggtgacgg tttggctgag agatgggaag cgacgcagaa cggtactggt    1800
gagcatcagc caccgccatt gccaccgggg atggtgagtt cttcgccgcg tgtgaggtat    1860
tactcggatt atattcagga atcgtctctt gtagtagaag ccattgagct ctcgggtcct    1920
cgatgattat gactcactgt ttttaaaaaa                                     1950

<210> SEQ ID NO 4
<211> LENGTH: 632
<212> TYPE: PRT
<213> ORGANISM: Arabidopsis thaliana

<400> SEQUENCE: 4

Met Glu Gly Val Arg Phe Val Val Trp Arg Leu Gly Phe Leu Val Phe
1               5                   10                  15

Val Trp Phe Phe Asp Ile Ser Ser Ala Thr Leu Ser Pro Thr Gly Val
            20                  25                  30

Asn Tyr Glu Val Thr Ala Leu Val Ala Val Lys Asn Glu Leu Asn Asp
        35                  40                  45

Pro Tyr Lys Val Leu Glu Asn Trp Asp Val Asn Ser Val Asp Pro Cys
    50                  55                  60

Ser Trp Arg Met Val Ser Cys Thr Asp Gly Tyr Val Ser Ser Leu Asp
65                  70                  75                  80

Leu Pro Ser Gln Ser Leu Ser Gly Thr Leu Ser Pro Arg Ile Gly Asn
                85                  90                  95

Leu Thr Tyr Leu Gln Ser Val Leu Gln Asn Asn Ala Ile Thr Gly Pro
            100                 105                 110

Ile Pro Glu Thr Ile Gly Arg Leu Glu Lys Leu Gln Ser Leu Asp Leu
        115                 120                 125

Ser Asn Asn Ser Phe Thr Gly Glu Ile Pro Ala Ser Leu Gly Glu Leu
    130                 135                 140

Lys Asn Leu Asn Tyr Leu Arg Leu Asn Asn Ser Leu Ile Gly Thr
145                 150                 155                 160

Cys Pro Glu Ser Leu Ser Lys Ile Glu Gly Leu Thr Leu Val Asp Ile
                165                 170                 175

Ser Tyr Asn Asn Leu Ser Gly Ser Leu Pro Lys Val Ser Ala Arg Thr
            180                 185                 190

Phe Lys Val Ile Gly Asn Ala Leu Ile Cys Gly Pro Lys Ala Val Ser
        195                 200                 205
```

```
Asn Cys Ser Ala Val Pro Glu Pro Leu Thr Leu Pro Gln Asp Gly Pro
    210                 215                 220

Asp Glu Ser Gly Thr Arg Thr Asn Gly His His Val Ala Leu Ala Phe
225                 230                 235                 240

Ala Ala Ser Phe Ser Ala Ala Phe Phe Val Phe Phe Thr Ser Gly Met
                245                 250                 255

Phe Leu Trp Trp Arg Tyr Arg Arg Asn Lys Gln Ile Phe Phe Asp Val
            260                 265                 270

Asn Glu Gln Tyr Asp Pro Glu Val Ser Leu Gly His Leu Lys Arg Tyr
        275                 280                 285

Thr Phe Lys Glu Leu Arg Ser Ala Thr Asn His Phe Asn Ser Lys Asn
    290                 295                 300

Ile Leu Gly Arg Gly Gly Tyr Gly Ile Val Tyr Lys Gly His Leu Asn
305                 310                 315                 320

Asp Gly Thr Leu Val Ala Val Lys Arg Leu Lys Asp Cys Asn Ile Ala
                325                 330                 335

Gly Gly Glu Val Gln Phe Gln Thr Glu Val Glu Thr Ile Ser Leu Ala
                340                 345                 350

Leu His Arg Asn Leu Leu Arg Leu Arg Gly Phe Cys Ser Ser Asn Gln
        355                 360                 365

Glu Arg Ile Leu Val Tyr Pro Tyr Pro Met Pro Asn Gly Ser Val Ala
    370                 375                 380

Ser Arg Leu Lys Asp Asn Ile Arg Gly Glu Pro Ala Leu Asp Trp Ser
385                 390                 395                 400

Arg Arg Lys Lys Ile Ala Val Gly Thr Ala Arg Gly Leu Val Tyr Leu
                405                 410                 415

His Glu Gln Cys Asp Pro Lys Ile Ile His Arg Asp Val Lys Ala Ala
        420                 425                 430

Asn Ile Leu Leu Asp Glu Asp Phe Glu Ala Val Val Gly Asp Phe Gly
    435                 440                 445

Leu Ala Lys Leu Leu Asp His Arg Asp Ser His Val Thr Thr Ala Val
450                 455                 460

Arg Gly Thr Val Gly His Ile Ala Pro Glu Tyr Leu Ser Thr Gly Gln
465                 470                 475                 480

Ser Ser Glu Lys Thr Asp Val Phe Gly Phe Gly Ile Leu Leu Leu Glu
                485                 490                 495

Leu Ile Thr Gly Gln Lys Ala Leu Asp Phe Gly Arg Ser Ala His Gln
        500                 505                 510

Lys Gly Val Met Leu Asp Trp Val Lys Lys Leu His Gln Glu Gly Lys
    515                 520                 525

Leu Lys Gln Leu Ile Asp Lys Asp Leu Asn Asp Lys Phe Asp Arg Val
    530                 535                 540

Glu Leu Glu Glu Ile Val Gln Val Ala Leu Leu Cys Thr Gln Phe Asn
545                 550                 555                 560

Pro Ser His Arg Pro Lys Met Ser Glu Val Met Lys Met Leu Glu Gly
                565                 570                 575

Asp Gly Leu Ala Glu Arg Trp Glu Ala Thr Gln Asn Gly Thr Gly Glu
            580                 585                 590

His Gln Pro Pro Pro Leu Pro Pro Gly Met Val Ser Ser Ser Pro Arg
        595                 600                 605

Val Arg Tyr Tyr Ser Asp Tyr Ile Gln Glu Ser Ser Leu Val Val Glu
    610                 615                 620

Ala Ile Glu Leu Ser Gly Pro Arg
```

```
                       625                 630

<210> SEQ ID NO 5
<211> LENGTH: 1891
<212> TYPE: DNA
<213> ORGANISM: Arabidopsis thaliana

<400> SEQUENCE: 5
tcaattttgg tagctcttag aaaaatggct ctgcttatta tcactgcctt agtttttagt      60
agtttatggt catctgtgtc accagatgct caaggggatg cattatttgc gttgaggagc     120
tcgttacgtg catctcctga acagcttagt gattggaacc agaatcaagt cgatccttgt     180
acttggtctc aagttatttg tgatgacaag aaacatgtta cttctgtaac cttgtcttac     240
atgaacttct cctcgggaac actgtcttca ggaataggaa tcttgacaac tctcaagact     300
cttacattga agggaaatgg aataatgggt ggaataccag aatccattgg aaatctgtct     360
agcttgacca gcttagattt ggaggataat cacttaactg atcgcattcc atccactctc     420
ggtaatctca agaatctaca gttcttcagg accttgagta ggaataaccct taatggttct     480 atcccggatt cacttacagg tctatcaaaa ctgataaata ttctgctcga ctcaaataat     540
ctcagtggtg agattcctca gagtttattc aaaatcccaa aatacaattt cacagcaaac     600
aacttgagct gtggtggcac tttcccgcaa ccttgtgtaa ccgagtccag tccttcaggt     660
gattcaagca gtagaaaaac tggaatcatc gctggagttg ttagcggaat agcggttatt     720
ctactaggat tcttcttctt tttcttctgc aaggataaac ataaaggata taaacgagac     780
gtatttgtgg atgttgcagg aacgaacttt aaaaaaggtt tgatttcagg tgaagtggac     840
agaaggattg cttttggaca gttgagaaga tttgcatgga gagagcttca gttggctaca     900
gatgagttca gtgaaaagaa tgttctcgga caaggaggct ttgggaaagt ttacaaagga     960
ttgctttcgg atggcaccaa agtcgctgta aaaagattga ctgattttga acgtccagga    1020
ggagatgaag ctttccagag agaagttgag atgataagtg tagctgttca taggaatctg    1080
cttcgcctta tcggcttttg tacaacacaa actgaacgac ttttggtgta tcctttcatg    1140
cagaatctaa gtgttgcata ttgcttaaga gagattaaac ccggggatcc agttctggat    1200
tggttcagga ggaaacagat tgcgttaggt gcagcacgag gactcgaata tcttcatgaa    1260
cattgcaacc cgaagatcat acacagagat gtgaaagctg caaatgtgtt actagatgaa    1320
gactttgaag cagtggttgg tgattttggt ttagccaagt tggtagatgt tagaaggact    1380
aatgtaacca ctcaggtccg aggaacaatg ggtcatattg caccagaatg tatatccaca    1440
gggaaatcgt cagagaaaac cgatgttttc gggtacggaa ttatgcttct ggagcttgta    1500
actggacaaa gagcaattga tttctcgcgg ttagaggaag aagatgatgt cttattgcta    1560
gaccatgtga agaaactgga agagagaag agattagaag acatagtaga taagaagctt    1620
gatgaggatt atataaagga agaagttgaa atgatgatac aagtagctct gctatgcaca    1680
caagcagcac cggaagaacg accagcgatg tcggaagtag taagaatgct agaaggagaa    1740
gggcttgcag agagatggga agagtggcag aatcttgaag tgacgagaca agaagagttt    1800
cagaggttgc agaggagatt tgattggggt gaagattcca ttaataatca agatgctatt    1860
gaattatctg gtggaagata gaaacaaaaa a                                   1891

<210> SEQ ID NO 6
<211> LENGTH: 617
<212> TYPE: PRT
<213> ORGANISM: Arabidopsis thaliana
```

<400> SEQUENCE: 6

```
Met Ala Leu Leu Ile Ile Thr Ala Leu Val Phe Ser Ser Leu Trp Ser
1               5                   10                  15

Ser Val Ser Pro Asp Ala Gln Gly Asp Ala Leu Phe Ala Leu Arg Ser
            20                  25                  30

Ser Leu Arg Ala Ser Pro Glu Gln Leu Ser Asp Trp Asn Gln Asn Gln
            35                  40                  45

Val Asp Pro Cys Thr Trp Ser Gln Val Ile Cys Asp Asp Lys Lys His
    50                  55                  60

Val Thr Ser Val Thr Leu Ser Tyr Met Asn Phe Ser Ser Gly Thr Leu
65                  70                  75                  80

Ser Ser Gly Ile Gly Ile Leu Thr Thr Leu Lys Thr Leu Thr Leu Lys
                85                  90                  95

Gly Asn Gly Ile Met Gly Gly Ile Pro Glu Ser Ile Gly Asn Leu Ser
                100                 105                 110

Ser Leu Thr Ser Leu Asp Leu Glu Asp Asn His Leu Thr Asp Arg Ile
            115                 120                 125

Pro Ser Thr Leu Gly Asn Leu Lys Asn Leu Gln Phe Leu Thr Leu Ser
130                 135                 140

Arg Asn Asn Leu Asn Gly Ser Ile Pro Asp Ser Leu Thr Gly Leu Ser
145                 150                 155                 160

Lys Leu Ile Asn Ile Leu Leu Asp Ser Asn Leu Ser Gly Glu Ile
                165                 170                 175

Pro Gln Ser Leu Phe Lys Ile Pro Lys Tyr Asn Phe Thr Ala Asn Asn
            180                 185                 190

Leu Ser Cys Gly Gly Thr Phe Pro Gln Pro Cys Val Thr Glu Ser Ser
            195                 200                 205

Pro Ser Gly Asp Ser Ser Arg Lys Thr Gly Ile Ile Ala Gly Val
210                 215                 220

Val Ser Gly Ile Ala Val Ile Leu Leu Gly Phe Phe Phe Phe Phe
225                 230                 235                 240

Cys Lys Asp Lys His Lys Gly Tyr Lys Arg Asp Val Phe Val Asp Val
                245                 250                 255

Ala Gly Thr Asn Phe Lys Lys Gly Leu Ile Ser Gly Glu Val Asp Arg
            260                 265                 270

Arg Ile Ala Phe Gly Gln Leu Arg Arg Phe Ala Trp Arg Glu Leu Gln
            275                 280                 285

Leu Ala Thr Asp Glu Phe Ser Glu Lys Asn Val Leu Gly Gln Gly Gly
            290                 295                 300

Phe Gly Lys Val Tyr Lys Gly Leu Leu Ser Asp Gly Thr Lys Val Ala
305                 310                 315                 320

Val Lys Arg Leu Thr Asp Phe Glu Arg Pro Gly Gly Asp Glu Ala Phe
                325                 330                 335

Gln Arg Glu Val Glu Met Ile Ser Val Ala Val His Arg Asn Leu Leu
            340                 345                 350

Arg Leu Ile Gly Phe Cys Thr Thr Gln Thr Glu Arg Leu Leu Val Tyr
            355                 360                 365

Pro Phe Met Gln Asn Leu Ser Val Ala Tyr Cys Leu Arg Glu Ile Lys
            370                 375                 380

Pro Gly Asp Pro Val Leu Asp Trp Phe Arg Arg Lys Gln Ile Ala Leu
385                 390                 395                 400

Gly Ala Ala Arg Gly Leu Glu Tyr Leu His Glu His Cys Asn Pro Lys
                405                 410                 415
```

```
Ile Ile His Arg Asp Val Lys Ala Ala Asn Val Leu Leu Asp Glu Asp
            420                 425                 430
Phe Glu Ala Val Val Gly Asp Phe Gly Leu Ala Lys Leu Val Asp Val
            435                 440                 445
Arg Arg Thr Asn Val Thr Thr Gln Val Arg Gly Thr Met Gly His Ile
450                 455                 460
Ala Pro Glu Cys Ile Ser Thr Gly Lys Ser Ser Glu Lys Thr Asp Val
465                 470                 475                 480
Phe Gly Tyr Gly Ile Met Leu Leu Glu Leu Val Thr Gly Gln Arg Ala
                485                 490                 495
Ile Asp Phe Ser Arg Leu Glu Glu Glu Asp Val Leu Leu Leu Asp
            500                 505                 510
His Val Lys Lys Leu Glu Arg Glu Lys Arg Leu Glu Asp Ile Val Asp
            515                 520                 525
Lys Lys Leu Asp Glu Asp Tyr Ile Lys Glu Glu Val Glu Met Met Ile
            530                 535                 540
Gln Val Ala Leu Leu Cys Thr Gln Ala Ala Pro Glu Glu Arg Pro Ala
545                 550                 555                 560
Met Ser Glu Val Val Arg Met Leu Glu Gly Glu Gly Leu Ala Glu Arg
                565                 570                 575
Trp Glu Glu Trp Gln Asn Leu Glu Val Thr Arg Gln Glu Phe Gln
            580                 585                 590
Arg Leu Gln Arg Arg Phe Asp Trp Gly Glu Asp Ser Ile Asn Asn Gln
            595                 600                 605
Asp Ala Ile Glu Leu Ser Gly Gly Arg
            610                 615

<210> SEQ ID NO 7
<211> LENGTH: 1864
<212> TYPE: DNA
<213> ORGANISM: Arabidopsis thaliana

<400> SEQUENCE: 7
aacggtgaaa gtttccatga tcctcttcga ggattcattc aaagaaattg ctttagatgg      60
aacaatcaga aattgatctt acaatgtttc atggccttag cttttgtggg aatcacttcg     120
tcaacaactc aaccagatat cgaaggagga gctctgttgc agctcagaga ttcgcttaat     180
gattcgagca atcgtctaaa atggacacgc gattttgtga gcccttgcta tagttggtct     240
tatgttacct gcagaggcca gagtgttgtg gctctaaatc ttgcctcgag tggattcaca     300
ggaacactct ctccagctat tacaaaactg aagttcttgg ttaccttaga gttacagaac     360
aatagtttat ctggtgcctt accagattct cttgggaaca tggttaatct acagacttta     420
aacctatcag tgaatagttt cagcggatcg ataccagcga gctggagtca gctctcgaat     480
ctaaagcact ggatctctc atccaataat ttaacaggaa gcatcccaac acaattcttc     540
tcaatcccaa cattcgattt tcaggaact cagcttatat gcggtaaaag tttgaatcag     600
ccttgttctt caagttctcg tcttccagtc acatcctcca agaaaaagct gagagacatt     660
actttgactg caagttgtgt tgcttctata atcttattcc ttggagcaat ggttatgtat     720
catcaccatc gcgtccgcag aaccaaatac gacatctttt tgatgtagc tggggaagat     780 gacaggaaga tttcctttgg acaactaaaa cgattctctt tacgtgaaat ccagctcgca     840
acagatagtt tcaacgagag caatttgata ggacaaggag gatttggtaa agtatacaga     900
ggtttgcttc cagacaaaac aaaagttgca gtgaaacgcc ttgcggatta cttcagtcct     960
ggaggagaag ctgctttcca aagagagatt cagctcataa gcgttgcggt tcataaaaat    1020
```

```
ctcttacgcc ttattggctt ctgcacaact tcctctgaga gaatccttgt ttatccatac    1080
atggaaaatc ttagtgttgc atatcgacta agagatttga aagcgggaga ggaaggatta    1140
gactggccaa caaggaagcg tgtagctttt ggttcagctc acggtttaga gtatctacac    1200
gaacattgta acccgaagat catacaccgc gatctcaagg ctgcaaacat acttttagac    1260
aacaattttg agccagttct tggagatttc ggtttagcta agcttgtgga cacatctctg    1320
actcatgtca caactcaagt ccgaggcaca atgggtcaca ttgcgccaga gtatctctgc    1380
acaggaaaat catctgaaaa aaccgatgtt tttggttacg gtataacgct tcttgagctt    1440
gttactggtc agcgcgcaat cgattttca cgcttggaag aagaggaaaa tattctcttg    1500
cttgatcata taaagaagtt gcttagaaaa cagagactta gagacattgt tgatagcaat    1560
ttgactacat atgactccaa agaagttgaa acaatcgttc aagtggctct tctctgcaca    1620
caaggctcac cagaagatag accagcgatg tctgaagtgg tcaaaatgct tcaagggact    1680
ggtggtttgg ctgagaaatg gactgaatgg gaacaacttg aagaagttag gaacaaagaa    1740
gcattgttgc ttccgacttt accggctact tgggatgaag aagaaccac cgttgatcaa    1800
gaatctatcc gattatcgac agcaagatga agaagaaaca gagagagaaa gatatctatg    1860
aaaa                                                                 1864

<210> SEQ ID NO 8
<211> LENGTH: 578
<212> TYPE: PRT
<213> ORGANISM: Arabidopsis thaliana

<400> SEQUENCE: 8

Met Ala Leu Ala Phe Val Gly Ile Thr Ser Ser Thr Thr Gln Pro Asp
1               5                   10                  15

Ile Glu Gly Gly Ala Leu Leu Gln Leu Arg Asp Ser Leu Asn Asp Ser
            20                  25                  30

Ser Asn Arg Leu Lys Trp Thr Arg Asp Phe Val Ser Pro Cys Tyr Ser
        35                  40                  45

Trp Ser Tyr Val Thr Cys Arg Gly Gln Ser Val Val Ala Leu Asn Leu
    50                  55                  60

Ala Ser Ser Gly Phe Thr Gly Thr Leu Ser Pro Ala Ile Thr Lys Leu
65                  70                  75                  80

Lys Phe Leu Val Thr Leu Glu Leu Gln Asn Asn Ser Leu Ser Gly Ala
                85                  90                  95

Leu Pro Asp Ser Leu Gly Asn Met Val Asn Leu Gln Thr Leu Asn Leu
            100                 105                 110

Ser Val Asn Ser Phe Ser Gly Ser Ile Pro Ala Ser Trp Ser Gln Leu
        115                 120                 125

Ser Asn Leu Lys His Leu Asp Leu Ser Ser Asn Asn Leu Thr Gly Ser
    130                 135                 140

Ile Pro Thr Gln Phe Phe Ser Ile Pro Thr Phe Glu Phe Ser Gly Thr
145                 150                 155                 160

Gln Leu Ile Cys Gly Lys Ser Leu Asn Gln Pro Cys Ser Ser Ser Arg
                165                 170                 175

Leu Pro Val Thr Ser Ser Lys Lys Lys Leu Arg Asp Ile Thr Leu Thr
            180                 185                 190

Ala Ser Cys Val Ala Ser Ile Ile Leu Phe Leu Gly Ala Met Val Met
        195                 200                 205

Tyr His His His Arg Val Arg Arg Thr Lys Tyr Asp Ile Phe Phe Asp
    210                 215                 220
```

Val Ala Gly Glu Asp Asp Arg Lys Ile Ser Phe Gly Gln Leu Lys Arg
225                 230                 235                 240

Phe Ser Leu Arg Glu Ile Gln Leu Ala Thr Asp Ser Phe Asn Glu Ser
            245                 250                 255

Asn Leu Ile Gly Gln Gly Gly Phe Gly Lys Val Tyr Arg Gly Leu Leu
        260                 265                 270

Pro Asp Lys Thr Lys Val Ala Val Lys Arg Leu Ala Asp Tyr Phe Ser
    275                 280                 285

Pro Gly Gly Glu Ala Ala Phe Gln Arg Glu Ile Gln Leu Ile Ser Val
290                 295                 300

Ala Val His Lys Asn Leu Leu Arg Leu Ile Gly Phe Cys Thr Thr Ser
305                 310                 315                 320

Ser Glu Arg Ile Leu Val Tyr Pro Tyr Met Glu Asn Leu Ser Val Ala
            325                 330                 335

Tyr Arg Leu Arg Asp Leu Lys Ala Gly Glu Glu Gly Leu Asp Trp Pro
        340                 345                 350

Thr Arg Lys Arg Val Ala Phe Gly Ser Ala His Gly Leu Glu Tyr Leu
    355                 360                 365

His Glu His Cys Asn Pro Lys Ile Ile His Arg Asp Leu Lys Ala Ala
370                 375                 380

Asn Ile Leu Leu Asp Asn Asn Phe Glu Pro Val Leu Gly Asp Phe Gly
385                 390                 395                 400

Leu Ala Lys Leu Val Asp Thr Ser Leu Thr His Val Thr Thr Gln Val
            405                 410                 415

Arg Gly Thr Met Gly His Ile Ala Pro Glu Tyr Leu Cys Thr Gly Lys
        420                 425                 430

Ser Ser Glu Lys Thr Asp Val Phe Gly Tyr Gly Ile Thr Leu Leu Glu
    435                 440                 445

Leu Val Thr Gly Gln Arg Ala Ile Asp Phe Ser Arg Leu Glu Glu Glu
450                 455                 460

Glu Asn Ile Leu Leu Leu Asp His Ile Lys Lys Leu Leu Arg Glu Gln
465                 470                 475                 480

Arg Leu Arg Asp Ile Val Asp Ser Asn Leu Thr Thr Tyr Asp Ser Lys
            485                 490                 495

Glu Val Glu Thr Ile Val Gln Val Ala Leu Leu Cys Thr Gln Gly Ser
        500                 505                 510

Pro Glu Asp Arg Pro Ala Met Ser Glu Val Val Lys Met Leu Gln Gly
    515                 520                 525

Thr Gly Gly Leu Ala Glu Lys Trp Thr Glu Trp Glu Gln Leu Glu Glu
530                 535                 540

Val Arg Asn Lys Glu Ala Leu Leu Leu Pro Thr Leu Pro Ala Thr Trp
545                 550                 555                 560

Asp Glu Glu Glu Thr Thr Val Asp Gln Glu Ser Ile Arg Leu Ser Thr
            565                 570                 575

Ala Arg

<210> SEQ ID NO 9
<211> LENGTH: 1980
<212> TYPE: DNA
<213> ORGANISM: Arabidopsis thaliana

<400> SEQUENCE: 9
tcttccttct ccttctggta atctaatcta aagcttttca tggtggtgat gaagatattc    60
tctgttctgt tactactatg tttcttcgtt acttgttctc tcttctga acccagaaac    120

```
cctgaagtgg aggcgttgat aaacataaag aacgagttac atgatccaca tggtgttttc      180
aaaaactggg atgagttttc tgttgatcct tgtagctgga ctatgatctc ttgttcttca      240
gacaacctcg taattggctt aggagctcca agtcagtctc tttcaggaac tttatctggg      300
tctattggaa atctcactaa tcttcgacaa gtgtcattac agaacaataa catctccggt      360
aaaatcccac cggagatttg ttctcttccc aaattacaga ctctggattt atccaataac      420
cggttctccg gtgaaatccc cggttctgtt aaccagctga gtaatctcca atatctgttg      480
aacaacaact cattatctgg gcccttttcct gcttctctgt ctcaaatccc tcacctctct     540
ttcttagact tgtcttataa caatctcaga ggtcctgttc ctaaatttcc tgcaaggaca      600
ttcaatgttg ctgggaaccc tttgatttgt aaaaacagcc taccggagat tgttcagga       660 tcaatcagtg caagccctct ttctgtctct ttacgttctt catcaggacg tagaaccaac      720
atattagcag ttgcacttgg tgtaagcctt ggctttgctg ttagtgtaat cctctctctc      780
gggttcattt ggtatcgaaa gaaacaaaga cggttaacga tgcttcgcat taacaagcaa      840
gaggaagggt tacttgggtt gggaaatcta agaagcttca cattcaggga acttcatgta      900
gctacggatg gttttagttc caagagtatt cttggtgctg gtgggtttgg taatgtctac      960
agaggaaaat tcggggatgg gacagtggtt gcagtgaaac gattgaaaga tgtgaatgga     1020
acctccggga actcacagtt tcgtactgag cttgagatga tcagcttagc tgttcatagg     1080
aatttgcttc ggttaatcgg ttattgtgcg agttctagcg aaagacttct tgtttaccct    1140
tacatgtcca atggcagcgt cgcctctagg ctcaaagcta agccagcgtt ggactggaac     1200
acaaggaaga agatagcgat tggagctgca agagggttgt tttatctaca cgagcaatgc     1260
gatcccaaga ttattcaccg agatgtcaag gcagcaaaca ttctcctaga tgagtatttt     1320
gaagcagttg ttgggatttt tggactagca aagctactca accacgagga ttcacatgtc     1380
acaaccgcgg ttagaggaac tgttggtcac attgcacctg agtatctctc caccggtcag     1440
tcatctgaga aaaccgatgt cttttgggttc ggtatacttt tgctagagct catcacagga    1500
atgagagctc tcgagtttgg caagtctgtt agccagaaag gagctatgct agaatgggtg     1560
aggaagctac acaaggaaat gaaagtagag gagctagtag accgagaact ggggacaacc     1620
tacgatagaa tagaagttgg agagatgcta caagtggcac tgctctgcac tcagtttctt     1680
ccagctcaca gacccaaaat gtctgaagta gttcagatgc ttgaaggaga tggattagct     1740
gagagatggg ctgcttcaca tgaccattca catttctacc atgccaacat gtcttacagg     1800
actattacct ctactgatgg caacaaccaa accaaacatc tgtttggctc ctcaggattt     1860
gaagatgaag atgataatca agcgttagat tcattcgcca tggaactatc tggtccaagg     1920
tagtaaatct tggacacaga aagaaacaga tataatatcc ccatgacttc aatttttgtt     1980
```

<210> SEQ ID NO 10
<211> LENGTH: 634
<212> TYPE: PRT
<213> ORGANISM: Arabidopsis thaliana

<400> SEQUENCE: 10

Met Val Val Met Lys Leu Ile Thr Met Lys Ile Phe Ser Val Leu Leu
1               5                   10                  15

Leu Leu Cys Phe Phe Val Thr Cys Ser Leu Ser Ser Glu Pro Arg Asn
            20                  25                  30

Pro Glu Val Glu Ala Leu Ile Asn Ile Lys Asn Glu Leu His Asp Pro
        35                  40                  45

-continued

His Gly Val Phe Lys Asn Trp Asp Glu Phe Ser Val Asp Pro Cys Ser
    50                  55                  60

Trp Thr Met Ile Ser Cys Ser Ser Asp Asn Leu Val Ile Gly Leu Gly
65                  70                  75                  80

Ala Pro Ser Gln Ser Leu Ser Gly Thr Leu Ser Gly Ser Ile Gly Asn
                85                  90                  95

Leu Thr Asn Leu Arg Gln Val Ser Leu Gln Asn Asn Asn Ile Ser Gly
            100                 105                 110

Lys Ile Pro Pro Glu Ile Cys Ser Leu Pro Lys Leu Gln Thr Leu Asp
        115                 120                 125

Leu Ser Asn Asn Arg Phe Ser Gly Glu Ile Pro Gly Ser Val Asn Gln
    130                 135                 140

Leu Ser Asn Leu Gln Tyr Leu Arg Leu Asn Asn Asn Ser Leu Ser Gly
145                 150                 155                 160

Pro Pro Phe Pro Ala Ser Leu Ser Gln Ile Pro His Leu Ser Phe Leu
                165                 170                 175

Asp Leu Ser Tyr Asn Asn Leu Arg Gly Pro Val Pro Lys Phe Pro Ala
            180                 185                 190

Arg Thr Phe Asn Val Ala Gly Asn Pro Leu Ile Cys Lys Asn Ser Leu
        195                 200                 205

Pro Glu Ile Cys Ser Gly Ser Ile Ser Ala Ser Pro Leu Ser Val Ser
    210                 215                 220

Leu Arg Ser Ser Ser Gly Arg Arg Thr Asn Ile Leu Ala Val Ala Leu
225                 230                 235                 240

Gly Val Ser Leu Gly Phe Ala Val Ser Val Ile Leu Ser Leu Gly Phe
                245                 250                 255

Ile Trp Tyr Arg Lys Lys Gln Arg Arg Leu Thr Met Leu Arg Ile Asn
            260                 265                 270

Lys Gln Glu Glu Gly Leu Leu Gly Leu Gly Asn Leu Arg Ser Phe Thr
        275                 280                 285

Phe Arg Glu Leu His Val Ala Thr Asp Gly Phe Ser Ser Lys Ser Ile
    290                 295                 300

Leu Gly Ala Gly Gly Phe Gly Asn Val Tyr Arg Gly Lys Phe Gly Asp
305                 310                 315                 320

Gly Thr Val Val Ala Val Lys Arg Leu Lys Asp Val Asn Gly Thr Ser
                325                 330                 335

Gly Asn Ser Gln Phe Arg Thr Glu Leu Glu Met Ile Ser Leu Ala Val
            340                 345                 350

His Arg Asn Leu Leu Arg Leu Ile Gly Tyr Cys Ala Ser Ser Ser Glu
        355                 360                 365

Arg Leu Leu Val Tyr Pro Tyr Met Ser Asn Gly Ser Val Ala Ser Arg
    370                 375                 380

Leu Lys Ala Lys Pro Ala Leu Asp Trp Asn Thr Arg Lys Lys Ile Ala
385                 390                 395                 400

Ile Gly Ala Ala Arg Gly Leu Phe Tyr Leu His Glu Gln Cys Asp Pro
                405                 410                 415

Lys Ile Ile His Arg Asp Val Lys Ala Ala Asn Ile Leu Leu Asp Glu
            420                 425                 430

Tyr Phe Glu Ala Val Val Gly Asp Phe Gly Leu Ala Lys Leu Leu Asn
        435                 440                 445

His Glu Asp Ser His Val Thr Thr Ala Val Arg Gly Thr Val Gly His
    450                 455                 460

Ile Ala Pro Glu Tyr Leu Ser Thr Gly Gln Ser Ser Glu Lys Thr Asp
465                 470                 475                 480

Val Phe Gly Phe Gly Ile Leu Leu Glu Leu Ile Thr Gly Met Arg
                485                 490                 495

Ala Leu Glu Phe Gly Lys Ser Val Ser Gln Lys Gly Ala Met Leu Glu
                500                 505                 510

Trp Val Arg Lys Leu His Lys Glu Met Lys Val Glu Leu Val Asp
                515                 520                 525

Arg Glu Leu Gly Thr Thr Tyr Asp Arg Ile Glu Val Gly Glu Met Leu
            530                 535                 540

Gln Val Ala Leu Leu Cys Thr Gln Phe Leu Pro Ala His Arg Pro Lys
545                 550                 555                 560

Met Ser Glu Val Val Gln Met Leu Gly Asp Gly Leu Ala Glu Arg
                565                 570                 575

Trp Ala Ala Ser His Asp His Ser His Phe Tyr His Ala Asn Met Ser
                580                 585                 590

Tyr Arg Thr Ile Thr Ser Thr Asp Gly Asn Asn Gln Thr Lys His Leu
            595                 600                 605

Phe Gly Ser Ser Gly Phe Glu Asp Glu Asp Asn Gln Ala Leu Asp
            610                 615                 620

Ser Phe Ala Met Glu Leu Ser Gly Pro Arg
625                 630

<210> SEQ ID NO 11
<211> LENGTH: 1893
<212> TYPE: DNA
<213> ORGANISM: Arabidopsis thaliana

<400> SEQUENCE: 11

```
ctagagaatt cttatacttt ttctacgatg gagatttctt tgatgaagtt tctgttttta      60
ggaatctggg tttattatta ctctgttctt gactctgttt ctgccatgga tagtcttttta    120
tctcccaagg tggctgcgtt aatgtcagtg aagaacaaga tgaaagatga aaagaggtt     180
ttgtctggtt gggatattaa ctctgttgat ccttgtactt ggaacatggt tggttgttct    240
tctgaaggtt ttgtggtttc tctagagatg gctagtaaag gattatcagg gatactatct    300
actagtattg gggaattaac tcatcttcat actttgttac ttcagaataa tcagttaact    360
ggtccgattc cttctgagtt aggccaactc tctgagcttg aaacgcttga tttatcgggg    420
aatcggttta gtggtgaaat cccagcttct ttagggttct taactcactt aaactacttg    480
cggcttagca ggaatctttt atctgggcaa gtccctcacc tcgtcgctgg cctctcaggt    540
cttttctttct tggatctatc tttcaacaat ctaagcggac caactccgaa tatatcagca    600
aaagattaca ggaaatgcat ttcttttgtgg tccagcttcc caagagcttt gctcagatgc    660
tacacctgtg agaaatgctg caatcgatct gcagcgacgg gtttgtctga aaaggacaat    720
agcaaacatc acagcttagt gctctctttt gcatttggca ttgttgttgc ctttatcatc    780
tccctaatgt ttctcttctt ctgggtgctt tggcatcgat cacgtctctc aagatcacac    840
gtgcagcaag actacgaatt tgaaatcggc catctgaaaa ggttcagttt tcgcgaaata    900
caaaccgcaa caagcaattt tagtccaaag aacatttttgg gacaaggagg gtttgggatg    960
gtttataaag ggtatctccc aaatggaact gtggtggcag ttaaaagatt gaaagatccg   1020
atttatacag gagaagttca gtttcaaacc gaagtagaga tgattggctt agctgttcac   1080
cgtaacctt tacgcctctt tggattctgt atgaccccgg aagagagaat gcttgtgtat   1140
ccgtacatgc caaatggaag cgtagctgat cgtctgagag attggaatcg gaggataagc   1200
attgcactcg gcgcagctcg aggacttgtt tacttgcacg agcaatgcaa tccaaagatt   1260
```

```
attcacagag acgtcaaagc tgcaaatatt ctacttgatg agagctttga agcaatagtt      1320
ggcgattttg gtctagcaaa gcttttagac cagagagatt cacatgtcac taccgcagtc      1380
cgaggaacca ttggacacat cgctcccgag tacctttcca ctggacagtc ctcagagaaa      1440
accgatgttt tcggattcgg agtactaatc cttgaactca taacaggtca taagatgatt      1500
gatcaaggca atggtcaagt tcgaaaagga atgatattga gctgggtaag gacattgaaa      1560
gcagagaaga gatttgcaga gatggtggac agagatttga agggagagtt tgatgatttg      1620
gtgttggagg aagtagtgga attggctttg ctttgtacac agccacatcc gaatctaaga      1680
ccgaggatgt ctcaagtgtt gaaggtacta gaaggtttag tggaacagtg tgaaggaggg      1740
tatgaagcta gagctccaag tgtctctagg aactacagta atggtcatga agagcagtcc      1800
tttattattg aagccattga gctctctgga ccacgatgat agacttcata gtgtcttaac      1860
tagtcttctt gattttgttg tcattgtcat ggc                                   1893
```

<210> SEQ ID NO 12
<211> LENGTH: 604
<212> TYPE: PRT
<213> ORGANISM: Arabidopsis thaliana

<400> SEQUENCE: 12

```
Met Glu Ile Ser Leu Met Lys Phe Leu Phe Leu Gly Ile Trp Val Tyr
1               5                   10                  15

Tyr Tyr Ser Val Leu Asp Ser Val Ser Ala Met Asp Ser Leu Leu Ser
                20                  25                  30

Pro Lys Val Ala Ala Leu Met Ser Val Lys Asn Lys Met Lys Asp Glu
            35                  40                  45

Lys Glu Val Leu Ser Gly Trp Asp Ile Asn Ser Val Asp Pro Cys Thr
        50                  55                  60

Trp Asn Met Val Gly Cys Ser Ser Glu Gly Phe Val Val Ser Leu Glu
65                  70                  75                  80

Met Ala Ser Lys Gly Leu Ser Gly Ile Leu Ser Thr Ser Ile Gly Glu
                85                  90                  95

Leu Thr His Leu His Thr Leu Leu Leu Gln Asn Asn Gln Leu Thr Gly
                100                 105                 110

Pro Ile Pro Ser Glu Leu Gly Gln Leu Ser Glu Leu Glu Thr Leu Asp
            115                 120                 125

Leu Ser Gly Asn Arg Phe Ser Gly Glu Ile Pro Ala Ser Leu Gly Phe
        130                 135                 140

Leu Thr His Leu Asn Tyr Leu Arg Leu Ser Arg Asn Leu Leu Ser Gly
145                 150                 155                 160

Gln Val Pro His Leu Val Ala Gly Leu Ser Gly Leu Ser Phe Leu Asp
                165                 170                 175

Leu Ser Phe Asn Asn Leu Ser Gly Pro Thr Pro Asn Ile Ser Ala Lys
            180                 185                 190

Asp Tyr Arg Lys Cys Ile Ser Leu Trp Ser Ser Phe Pro Arg Ala Leu
        195                 200                 205

Leu Arg Cys Tyr Thr Cys Glu Lys Cys Cys Asn Arg Ser Ala Ala Thr
    210                 215                 220

Gly Leu Ser Glu Lys Asp Asn Ser Lys His His Ser Leu Val Leu Ser
225                 230                 235                 240

Phe Ala Phe Gly Ile Val Val Ala Phe Ile Ile Ser Leu Met Phe Leu
                245                 250                 255

Phe Phe Trp Val Leu Trp His Arg Ser Arg Leu Ser Arg Ser His Val
```

```
                260             265             270
Gln Gln Asp Tyr Glu Phe Glu Ile Gly His Leu Lys Arg Phe Ser Phe
            275                 280                 285
Arg Glu Ile Gln Thr Ala Thr Ser Asn Phe Ser Pro Lys Asn Ile Leu
        290                 295                 300
Gly Gln Gly Gly Phe Gly Met Val Tyr Lys Gly Tyr Leu Pro Asn Gly
305                 310                 315                 320
Thr Val Ala Val Lys Arg Leu Lys Asp Pro Ile Tyr Thr Gly Glu
                325                 330                 335
Val Gln Phe Gln Thr Glu Val Glu Met Ile Gly Leu Ala Val His Arg
            340                 345                 350
Asn Leu Leu Arg Leu Phe Gly Phe Cys Met Thr Pro Glu Glu Arg Met
            355                 360                 365
Leu Val Tyr Pro Tyr Met Pro Asn Gly Ser Val Ala Asp Arg Leu Arg
        370                 375                 380
Asp Trp Asn Arg Arg Ile Ser Ile Ala Leu Gly Ala Ala Arg Gly Leu
385                 390                 395                 400
Val Tyr Leu His Glu Gln Cys Asn Pro Lys Ile Ile His Arg Asp Val
                405                 410                 415
Lys Ala Ala Asn Ile Leu Leu Asp Glu Ser Phe Glu Ala Ile Val Gly
            420                 425                 430
Asp Phe Gly Leu Ala Lys Leu Leu Asp Gln Arg Asp Ser His Val Thr
            435                 440                 445
Thr Ala Val Arg Gly Thr Ile Gly His Ile Ala Pro Glu Tyr Leu Ser
        450                 455                 460
Thr Gly Gln Ser Ser Glu Lys Thr Asp Val Phe Gly Phe Gly Val Leu
465                 470                 475                 480
Ile Leu Glu Leu Ile Thr Gly His Lys Met Ile Asp Gln Asn Gly
                485                 490                 495
Gln Val Arg Lys Gly Met Ile Leu Ser Trp Val Arg Thr Leu Lys Ala
            500                 505                 510
Glu Lys Arg Phe Ala Glu Met Val Asp Arg Asp Leu Lys Gly Glu Phe
            515                 520                 525
Asp Asp Leu Val Leu Glu Glu Val Val Glu Leu Ala Leu Leu Cys Thr
        530                 535                 540
Gln Pro His Pro Asn Leu Arg Pro Arg Met Ser Gln Val Leu Lys Val
545                 550                 555                 560
Leu Glu Gly Leu Val Glu Gln Cys Glu Gly Gly Tyr Glu Ala Arg Ala
                565                 570                 575
Pro Ala Ser Val Ser Arg Asn Tyr Ser Asn Gly His Glu Glu Gln Ser
            580                 585                 590
Phe Ile Ile Glu Ala Ile Glu Leu Ser Gly Pro Arg
            595                 600

<210> SEQ ID NO 13
<211> LENGTH: 1920
<212> TYPE: DNA
<213> ORGANISM: Arabidopsis thaliana

<400> SEQUENCE: 13
attgtttcct tcttttggga ttttctcctt ggatggaacc agctcaatta atgagatgag    60
atgagaatgt tcagcttgca gaagatggct atggctttta ctctcttgtt ttttgcctgt   120
ttatgctcat ttgtgtctcc agatgctcaa ggggatgcac tgtttgcgtt gaggatctcc   180
ttacgtgcat taccgaatca gctaagtgac tggaatcaga accaagttaa tccttgcact   240
```

-continued

```
tggtcccaag ttatttgtga tgacaaaaac tttgtcactt ctcttacatt gtcagatatg    300
aacttctcgg gaaccttgtc ttcaagagta ggaatcctag aaaatctcaa gactcttact    360
ttaaagggaa atggaattac gggtgaaata ccagaagact ttggaaatct gactagcttg    420
actagtttgg atttggagga caatcagcta actggtcgta taccatccac tatcggtaat    480
ctcaagaaac ttcagttctt gaccttgagt aggaacaaac ttaatgggac tattccggag    540
tcactcactg gtcttccaaa cctgttaaac ctgctgcttg attccaatag tctcagtggt    600
cagattcctc aaagtctgtt tgagatccca aaatataatt tcacgtcaaa caacttgaat    660
tgtggcggtc gtcaacctca cccttgtgta tccgcggttg cccattcagg tgattcaagc    720
aagcctaaaa ctggcattat tgctggagtt gttgctggag ttacagttgt tctctttgga    780
atcttgttgt ttctgttctg caaggatagg cataaaggat atagacgtga tgtgtttgtg    840
gatgttgcag gtgaagtgga caggagaatt gcatttggac agttgaaaag gtttgcatgg    900
agagagctcc agttagcgac agataacttc agcgaaaaga atgtacttgg tcaaggaggc    960
tttgggaaag tttacaaagg agtgcttccg gatacaccca agttgctgtg aagagattg    1020 acggatttcg aaagtcctgg tggagatgct gctttccaaa gggaagtaga gatgataagt    1080
gtagctgttc ataggaatct actccgtctt atcgggttct gcaccacaca aacagaacgc    1140
cttttggttt atcccttcat gcagaatcta agtcttgcac atcgtctgag agagatcaaa    1200
gcaggcgacc cggttctaga ttgggagacg aggaaacgga ttgccttagg agcagcgcgt    1260
ggttttgagt atcttcatga acattgcaat ccgaagatca tacatcgtga tgtgaaagca    1320
gctaatgtgt tactagatga agattttgaa gcagtggttg gtgattttgg tttagccaag    1380
ctagtagatg ttagaaggac taatgtgact actcaagttc gaggaacaat gggtcacatt    1440
gcaccagaat atttatcaac agggaaatca tcagagagaa ccgatgtttt cgggtatgga    1500
attatgcttc ttgagcttgt tacaggacaa cgcgcaatag acttttcacg tttggaggaa    1560
gaagatgatg tcttgttact tgaccacgtg aagaaactgg aaagagagaa gagattagga    1620
gcaatcgtag ataagaattt ggatggagag tatataaaag aagaagtaga gatgatgata    1680
caagtggctt tgctttgtac acaaggttca ccagaagacc gaccagtgat gtctgaagtt    1740
gtgaggatgt tagaaggaga agggcttgcg gagagatggg aagagtggca aaacgtggaa    1800
gtcacgagac gtcatgagtt tgaacggttg cagaggagat ttgattgggg tgaagattct    1860
atgcataacc aagatgccat tgaattatct ggtggaagat gaccaaaaac atcaaacctt    1920
```

<210> SEQ ID NO 14
<211> LENGTH: 613
<212> TYPE: PRT
<213> ORGANISM: Arabidopsis thaliana

<400> SEQUENCE: 14

```
Met Arg Met Phe Ser Leu Gln Lys Met Ala Met Ala Phe Thr Leu Leu
1               5                   10                  15

Phe Phe Ala Cys Leu Cys Ser Phe Val Ser Pro Asp Ala Gln Gly Asp
            20                  25                  30

Ala Leu Phe Ala Leu Arg Ile Ser Leu Arg Ala Leu Pro Asn Gln Leu
        35                  40                  45

Ser Asp Trp Asn Gln Asn Gln Val Asn Pro Cys Thr Trp Ser Gln Val
    50                  55                  60

Ile Cys Asp Asp Lys Asn Phe Val Thr Ser Leu Thr Leu Ser Asp Met
65                  70                  75                  80
```

-continued

```
Asn Phe Ser Gly Thr Leu Ser Ser Arg Val Gly Ile Leu Glu Asn Leu
                85                  90                  95

Lys Thr Leu Thr Leu Lys Gly Asn Gly Ile Thr Gly Glu Ile Pro Glu
            100                 105                 110

Asp Phe Gly Asn Leu Thr Ser Leu Thr Ser Leu Asp Leu Glu Asp Asn
            115                 120                 125

Gln Leu Thr Gly Arg Ile Pro Ser Thr Ile Gly Asn Leu Lys Lys Leu
        130                 135                 140

Gln Phe Leu Thr Leu Ser Arg Asn Lys Leu Asn Gly Thr Ile Pro Glu
145                 150                 155                 160

Ser Leu Thr Gly Leu Pro Asn Leu Leu Asn Leu Leu Asp Ser Asn
                165                 170                 175

Ser Leu Ser Gly Gln Ile Pro Gln Ser Leu Phe Glu Ile Pro Lys Tyr
            180                 185                 190

Asn Phe Thr Ser Asn Asn Leu Asn Cys Gly Gly Arg Gln Pro His Pro
                195                 200                 205

Cys Val Ser Ala Val Ala His Ser Gly Asp Ser Ser Lys Pro Lys Thr
        210                 215                 220

Gly Ile Ile Ala Gly Val Val Ala Gly Val Thr Val Val Leu Phe Gly
225                 230                 235                 240

Ile Leu Leu Phe Leu Phe Cys Lys Asp Arg His Lys Gly Tyr Arg Arg
                245                 250                 255

Asp Val Phe Val Asp Val Ala Gly Glu Val Asp Arg Arg Ile Ala Phe
            260                 265                 270

Gly Gln Leu Lys Arg Phe Ala Trp Arg Glu Leu Gln Leu Ala Thr Asp
        275                 280                 285

Asn Phe Ser Glu Lys Asn Val Leu Gly Gln Gly Gly Phe Gly Lys Val
290                 295                 300

Tyr Lys Gly Val Leu Pro Asp Thr Pro Lys Val Ala Val Lys Arg Leu
305                 310                 315                 320

Thr Asp Phe Glu Ser Pro Gly Gly Asp Ala Ala Phe Gln Arg Glu Val
                325                 330                 335

Glu Met Ile Ser Val Ala Val His Arg Asn Leu Leu Arg Leu Ile Gly
            340                 345                 350

Phe Cys Thr Thr Gln Thr Glu Arg Leu Leu Val Tyr Pro Phe Met Gln
        355                 360                 365

Asn Leu Ser Leu Ala His Arg Leu Arg Glu Ile Lys Ala Gly Asp Pro
370                 375                 380

Val Leu Asp Trp Glu Thr Arg Lys Arg Ile Ala Leu Gly Ala Ala Arg
385                 390                 395                 400

Gly Phe Glu Tyr Leu His Glu His Cys Asn Pro Lys Ile Ile His Arg
                405                 410                 415

Asp Val Lys Ala Ala Asn Val Leu Leu Asp Glu Asp Phe Glu Ala Val
            420                 425                 430

Val Gly Asp Phe Gly Leu Ala Lys Leu Val Asp Val Arg Arg Thr Asn
        435                 440                 445

Val Thr Thr Gln Val Arg Gly Thr Met Gly His Ile Ala Pro Glu Tyr
450                 455                 460

Leu Ser Thr Gly Lys Ser Ser Glu Arg Thr Asp Val Phe Gly Tyr Gly
465                 470                 475                 480

Ile Met Leu Leu Glu Leu Val Thr Gly Gln Arg Ala Ile Asp Phe Ser
                485                 490                 495

Arg Leu Glu Glu Glu Asp Asp Val Leu Leu Leu Asp His Val Lys Lys
            500                 505                 510
```

```
Leu Glu Arg Glu Lys Arg Leu Gly Ala Ile Val Asp Lys Asn Leu Asp
        515                 520                 525

Gly Glu Tyr Ile Lys Glu Val Glu Met Met Ile Gln Val Ala Leu
    530                 535                 540

Leu Cys Thr Gln Gly Ser Pro Glu Asp Arg Pro Val Met Ser Glu Val
545                 550                 555                 560

Val Arg Met Leu Glu Gly Glu Gly Leu Ala Glu Arg Trp Glu Trp
            565                 570                 575

Gln Asn Val Glu Val Thr Arg Arg His Glu Phe Glu Arg Leu Gln Arg
            580                 585                 590

Arg Phe Asp Trp Gly Glu Asp Ser Met His Asn Gln Asp Ala Ile Glu
        595                 600                 605

Leu Ser Gly Gly Arg
    610

<210> SEQ ID NO 15
<211> LENGTH: 2217
<212> TYPE: DNA
<213> ORGANISM: Arabidopsis thaliana

<400> SEQUENCE: 15
acatcttgtt ttctgctcat tcctctgttt caacaatgga gagtactatt gttatgatga      60
tgatgataac aagatctttc ttttgcttct tgggattttt atgccttctc tgctcttctg     120
ttcacggatt gctttctcct aaaggtgtta actttgaagt gcaagctttg atggacataa     180
aagcttcatt acatgatcct catggtgttc ttgataactg ggatagagat gctgttgatc     240
cttgtagttg acaatggtc acttgttctt ctgaaaactt tgtcattggc ttaggcacac      300
caagtcagaa tttatctggt acactatctc aagcattac caacttaaca aatcttcgga     360
ttgtgctgtt gcagaacaac aacataaaag gaaaaattcc tgctgagatt ggtcggctta     420
cgaggcttga gactcttgat cttctgata atttcttcca cggtgaaatt ccttttttcag     480 taggctatct acaaagcctg caatatctga ggcttaacaa caattctctc tctggagtgt     540
ttcctctgtc actatctaat atgactcaac ttgccttct tgatttatca tacaacaatc     600
ttagtggtcc tgttccaaga tttgctgcaa agacgtttag catcgttggg aacccgctga     660
tatgtccaac gggtaccgaa ccagactgca atggaacaac attgatacct atgtctatga     720
acttgaatca aactggagtt cctttatacg ccggtggatc gaggaatcac aaaatggcaa     780
tcgctgttgg atccagcgtt gggactgtat cattaatctt cattgctgtt ggtttgtttc     840
tctggtggag acaaagacat aaccaaaaca cattctttga tgttaaagat gggaatcatc     900
atgaggaagt ttcacttgga aacctgagga gatttggttt cagggagctt cagattgcga     960
ccaataactt cagcagtaag aacttattgg ggaaaggtgg ctatggaaat gtatacaaag    1020
gaatacttgg agatagtaca gtggttgcag tgaaaaggct taaagatgga ggagcattgg    1080
gaggagagat tcagtttcag acagaagttg aaatgatcag tttagctgtt catcgaaatc    1140
tcttaagact ctacggtttc tgcatcacac aaactgagaa gcttctagtt tatccttata    1200
tgtctaatgg aagcgttgca tctcgaatga agcaaaacc tgttcttgac tggagcataa    1260
ggaagaggat agcctagga gctgcaagag ggcttgtgta tctccatgag caatgtgatc    1320
cgaagattat ccaccgcgat gtcaaagcag cgaatatact tcttgatgac tactgtgaag    1380
ctgtggttgg cgattttggt ttagctaaac tcttggatca tcaagattct catgtgacaa    1440
ccgcggttag aggcacggtg ggtcacattg ctccagagta tctctcaact ggtcaatcct    1500
```

-continued

```
ctgagaaaac agatgttttt ggcttcggga ttcttcttct tgagcttgta accggacaaa   1560
gagcttttga gtttggtaaa gcggctaacc agaaaggtgt gatgcttgat tgggttaaaa   1620
agattcatca agagaagaaa cttgagctac ttgtggataa agagttgttg aagaagaaga   1680
gctacgatga gattgagtta gacgaaatgg taagagtagc tttgttgtgc acacagtacc   1740
tgccaggaca tagaccaaaa atgtctgaag ttgttcgaat gctggaagga gatggacttg   1800
cagagaaatg ggaagcttct caaagatcag acagtgtttc aaaatgtagc aacaggataa   1860
atgaattgat gtcatcttca gacagatact ctgatcttac cgatgactct agtttacttg   1920
tgcaagcaat ggagctctct ggtcctagat gaaatctata catgaatctg aagaagaaga   1980
agaacatgca tctgtttctt gaatcaagag ggattcttgt ttttttgtat aatagagagg   2040
ttttttggag ggaaatgttg tgtctctgta actgtatagg cttgttgtgt aagaagttat   2100
tactgcactt agggttaatt caaagttctt tacataaaaa atgattagtt gcgttgaata   2160
gagggaacac tttgggagat ttcatgtatg aaatttggaa aaaaaaaaaa aaaaaaa     2217
```

<210> SEQ ID NO 16
<211> LENGTH: 638
<212> TYPE: PRT
<213> ORGANISM: Arabidopsis thaliana

<400> SEQUENCE: 16

```
Met Glu Ser Thr Ile Val Met Met Met Ile Thr Arg Ser Phe Phe
1               5                   10                  15

Cys Phe Leu Gly Phe Leu Cys Leu Leu Cys Ser Ser Val His Gly Leu
                20                  25                  30

Leu Ser Pro Lys Gly Val Asn Phe Glu Val Gln Ala Leu Met Asp Ile
            35                  40                  45

Lys Ala Ser Leu His Asp Pro His Gly Val Leu Asp Asn Trp Asp Arg
        50                  55                  60

Asp Ala Val Asp Pro Cys Ser Trp Thr Met Val Thr Cys Ser Ser Glu
65                  70                  75                  80

Asn Phe Val Ile Gly Leu Gly Thr Pro Ser Gln Asn Leu Ser Gly Thr
                85                  90                  95

Leu Ser Pro Ser Ile Thr Asn Leu Thr Asn Leu Arg Ile Val Leu Leu
            100                 105                 110

Gln Asn Asn Asn Ile Lys Gly Lys Ile Pro Ala Glu Ile Gly Arg Leu
        115                 120                 125

Thr Arg Leu Glu Thr Leu Asp Leu Ser Asp Asn Phe Phe His Gly Glu
    130                 135                 140

Ile Pro Phe Ser Val Gly Tyr Leu Gln Ser Leu Gln Tyr Leu Arg Leu
145                 150                 155                 160

Asn Asn Asn Ser Leu Ser Gly Val Phe Pro Leu Ser Leu Ser Asn Met
                165                 170                 175

Thr Gln Leu Ala Phe Leu Asp Leu Ser Tyr Asn Asn Leu Ser Gly Pro
            180                 185                 190

Val Pro Arg Phe Ala Ala Lys Thr Phe Ser Ile Val Gly Asn Pro Leu
        195                 200                 205

Ile Cys Pro Thr Gly Thr Glu Pro Asp Cys Asn Gly Thr Thr Leu Ile
    210                 215                 220

Pro Met Ser Met Asn Leu Asn Gln Thr Gly Val Pro Leu Tyr Ala Gly
225                 230                 235                 240

Gly Ser Arg Asn His Lys Met Ala Ile Ala Val Gly Ser Ser Val Gly
                245                 250                 255
```

```
Thr Val Ser Leu Ile Phe Ile Ala Val Gly Leu Phe Leu Trp Trp Arg
            260                 265                 270

Gln Arg His Asn Gln Asn Thr Phe Asp Val Lys Asp Gly Asn His
        275                 280                 285

His Glu Glu Val Ser Leu Gly Asn Leu Arg Arg Phe Gly Phe Arg Glu
290                 295                 300

Leu Gln Ile Ala Thr Asn Asn Phe Ser Ser Lys Asn Leu Leu Gly Lys
305                 310                 315                 320

Gly Gly Tyr Gly Asn Val Tyr Lys Gly Ile Leu Gly Asp Ser Thr Val
                325                 330                 335

Val Ala Val Lys Arg Leu Lys Asp Gly Gly Ala Leu Gly Gly Glu Ile
            340                 345                 350

Gln Phe Gln Thr Glu Val Glu Met Ile Ser Leu Ala Val His Arg Asn
        355                 360                 365

Leu Leu Arg Leu Tyr Gly Phe Cys Ile Thr Gln Thr Glu Lys Leu Leu
    370                 375                 380

Val Tyr Pro Tyr Met Ser Asn Gly Ser Val Ala Ser Arg Met Lys Ala
385                 390                 395                 400

Lys Pro Val Leu Asp Trp Ser Ile Arg Lys Arg Ile Ala Ile Gly Ala
                405                 410                 415

Ala Arg Gly Leu Val Tyr Leu His Glu Gln Cys Asp Pro Lys Ile Ile
            420                 425                 430

His Arg Asp Val Lys Ala Ala Asn Ile Leu Leu Asp Asp Tyr Cys Glu
        435                 440                 445

Ala Val Val Gly Asp Phe Gly Leu Ala Lys Leu Leu Asp His Gln Asp
    450                 455                 460

Ser His Val Thr Thr Ala Val Arg Gly Thr Val Gly His Ile Ala Pro
465                 470                 475                 480

Glu Tyr Leu Ser Thr Gly Gln Ser Ser Glu Lys Thr Asp Val Phe Gly
                485                 490                 495

Phe Gly Ile Leu Leu Leu Glu Leu Val Thr Gly Gln Arg Ala Phe Glu
            500                 505                 510

Phe Gly Lys Ala Ala Asn Gln Lys Gly Val Met Leu Asp Trp Val Lys
        515                 520                 525

Lys Ile His Gln Glu Lys Lys Leu Glu Leu Leu Val Asp Lys Glu Leu
    530                 535                 540

Leu Lys Lys Lys Ser Tyr Asp Glu Ile Glu Leu Asp Glu Met Val Arg
545                 550                 555                 560

Val Ala Leu Leu Cys Thr Gln Tyr Leu Pro Gly His Arg Pro Lys Met
                565                 570                 575

Ser Glu Val Val Arg Met Leu Glu Gly Asp Gly Leu Ala Glu Lys Trp
            580                 585                 590

Glu Ala Ser Gln Arg Ser Asp Ser Val Ser Lys Cys Ser Asn Arg Ile
        595                 600                 605

Asn Glu Leu Met Ser Ser Ser Asp Arg Tyr Ser Asp Leu Thr Asp Asp
    610                 615                 620

Ser Ser Leu Leu Val Gln Ala Met Glu Leu Ser Gly Pro Arg
625                 630                 635

<210> SEQ ID NO 17
<211> LENGTH: 2021
<212> TYPE: DNA
<213> ORGANISM: Arabidopsis thaliana

<400> SEQUENCE: 17
```

```
gtttttttttt ttttaccctc ttggaggatc tgggaggaga aatttgcttt ttttggtaa      60
atggggagaa aaaagtttga agcttttggt tttgtctgct taatctcact gcttcttctg     120
tttaattcgt tatggcttgc ctcttctaac atggaaggtg atgcactgca cagtttgaga     180
gctaatctag ttgatccaaa taatgtcttg caaagctggg atcctacgct tgttaatccg     240
tgtacttggt ttcacgtaac gtgtaacaac gagaacagtg ttataagagt cgatcttggg     300
aatgcagact tgtctggtca gttggttcct cagctaggtc agctcaagaa cttgcagtac     360
ttggagcttt atagtaataa cataaccggg ccggttccaa gcgatcttgg gaatctgaca     420
aacttagtga gcttggatct ttacttgaac agcttcactg gtccaattcc agattctcta     480
ggaaagctat tcaagcttcg ctttcttcgg ctcaacaata acagtctcac cggaccaatt     540
cccatgtcat tgactaatat catgacccct caagttttgg atctgtcgaa caaccgatta     600
tccggatctg ttcctgataa tggttccttc tcgctcttca ctcccatcag ttttgctaac     660
aacttggatc tatgcggccc agttactagc cgtccttgtc ctggatctcc cccgttttct     720
cctccaccac ctttatacc acctcccata gttcctacac caggtgggta tagtgctact     780
ggagccattg cggaggagt tgctgctggt gctgctttac tatttgctgc ccctgcttta     840
gcttttgctt ggtggcgtag aagaaaacct caagaattct tctttgatgt tcctgccgaa     900
gaggaccctg aggttcactt ggggcagctt aagcggttct ctctacggga acttcaagta     960
gcaactgata gcttcagcaa caagaacatt ttgggccgag gtgggttcgg aaaagtctac    1020
aaaggccgtc ttgctgatgg aacacttgtt gcagtcaaac ggcttaaaga agagcgaacc    1080
ccaggtggcg agctccagtt tcagacagaa gtggagatga taagcatggc cgttcacaga    1140
aatctcctca ggctacgcgg tttctgtatg acccctaccg agagattgct tgtttatcct    1200
tacatggcta atggaagtgt cgcttcctgt ttgagagaac gtccaccatc acagttgcct    1260
ctagcctggt caataagaca gcaaatcgcg ctaggatcag cgaggggttt gtcttatctt    1320
catgatcatt gcgaccccaa aattattcac cgtgatgtga agctgctaa tattctgttg    1380
gacgaggaat ttgaggcggt ggtaggtgat ttcgggttag ctagacttat ggactataaa    1440
gatactcatg tcacaacggc tgtgcgtggg actattggac acattgctcc tgagtatctc    1500
tcaactggaa atcttcaga gaaaactgat gttttggct acgggatcat gcttttggaa    1560
ctgattacag gtcagagagc ttttgatctt gcaagactgg cgaatgacga tgacgttatg    1620
ctcctagatt gggtgaaagg gcttttgaag gagaagaagc tggagatgct tgtggatcct    1680
gacctgcaaa gcaattacac agaagcagaa gtagaacagc tcatacaagt ggctcttctc    1740
tgcacacaga gctcacctat ggaacgacct aagatgtctg aggttgttcg aatgcttgaa    1800
ggtgacggtt tagcggagaa atgggacgag tggcagaaag tggaagttct caggcaagaa    1860
gtggagctct cttctcaccc cacctctgac tggatccttg attcgactga taatcttcat    1920
gctatggagt tgtctggtcc aagataaacg acattgtaat ttgcctaaca gaaaagagaa    1980
agaacagaga aatattaaga gaatcacttc tctgtattct                           2021
```

<210> SEQ ID NO 18
<211> LENGTH: 628
<212> TYPE: PRT
<213> ORGANISM: Arabidopsis thaliana

<400> SEQUENCE: 18

```
Met Gly Arg Lys Lys Phe Glu Ala Phe Gly Phe Val Cys Leu Ile Ser
1               5                   10                  15

Leu Leu Leu Leu Phe Asn Ser Leu Trp Leu Ala Ser Ser Asn Met Glu
```

-continued

```
                20                  25                  30
Gly Asp Ala Leu His Ser Leu Arg Ala Asn Leu Val Asp Pro Asn Asn
                35                  40                  45
Val Leu Gln Ser Trp Asp Pro Thr Leu Val Asn Pro Cys Thr Trp Phe
                50                  55                  60
His Val Thr Cys Asn Asn Glu Asn Ser Val Ile Arg Val Asp Leu Gly
65                  70                  75                  80
Asn Ala Asp Leu Ser Gly Gln Leu Val Pro Gln Leu Gly Gln Leu Lys
                    85                  90                  95
Asn Leu Gln Tyr Leu Glu Leu Tyr Ser Asn Asn Ile Thr Gly Pro Val
                    100                 105                 110
Pro Ser Asp Leu Gly Asn Leu Thr Asn Leu Val Ser Leu Asp Leu Tyr
                    115                 120                 125
Leu Asn Ser Phe Thr Gly Pro Ile Pro Asp Ser Leu Gly Lys Leu Phe
                    130                 135                 140
Lys Leu Arg Phe Leu Arg Leu Asn Asn Asn Ser Leu Thr Gly Pro Ile
145                 150                 155                 160
Pro Met Ser Leu Thr Asn Ile Met Thr Leu Gln Val Leu Asp Leu Ser
                    165                 170                 175
Asn Asn Arg Leu Ser Gly Ser Val Pro Asp Asn Gly Ser Phe Ser Leu
                    180                 185                 190
Phe Thr Pro Ile Ser Phe Ala Asn Asn Leu Asp Leu Cys Gly Pro Val
                    195                 200                 205
Thr Ser Arg Phe Cys Pro Gly Ser Pro Pro Phe Ser Pro Pro Pro Pro
                    210                 215                 220
Phe Ile Pro Pro Ile Val Pro Thr Pro Gly Gly Tyr Ser Ala Thr
225                 230                 235                 240
Gly Ala Ile Ala Gly Gly Val Ala Ala Gly Ala Ala Leu Leu Phe Ala
                    245                 250                 255
Ala Pro Ala Leu Ala Phe Ala Trp Trp Arg Arg Arg Lys Pro Gln Glu
                    260                 265                 270
Phe Phe Phe Asp Val Pro Ala Glu Glu Asp Pro Glu Val His Leu Gly
                    275                 280                 285
Gln Leu Lys Arg Phe Ser Leu Arg Glu Leu Gln Val Ala Thr Asp Ser
                    290                 295                 300
Phe Ser Asn Lys Asn Ile Leu Gly Arg Gly Phe Gly Lys Val Tyr
305                 310                 315                 320
Lys Gly Arg Leu Ala Asp Gly Thr Leu Val Ala Val Lys Arg Leu Lys
                    325                 330                 335
Glu Glu Arg Thr Pro Gly Gly Glu Leu Gln Phe Gln Thr Glu Val Glu
                    340                 345                 350
Met Ile Ser Met Ala Val His Arg Asn Leu Leu Arg Leu Arg Gly Phe
                    355                 360                 365
Cys Met Thr Pro Thr Glu Arg Leu Leu Val Tyr Pro Tyr Met Ala Asn
                    370                 375                 380
Gly Ser Val Ala Ser Cys Leu Arg Glu Arg Pro Pro Ser Gln Leu Pro
385                 390                 395                 400
Leu Ala Trp Ser Ile Arg Gln Gln Ile Ala Leu Gly Ser Ala Arg Gly
                    405                 410                 415
Leu Ser Tyr Leu His Asp His Cys Asp Pro Lys Ile Ile His Arg Asp
                    420                 425                 430
Val Lys Ala Ala Asn Ile Leu Leu Asp Glu Glu Phe Glu Ala Val Val
                    435                 440                 445
```

```
Gly Asp Phe Gly Leu Ala Arg Leu Met Asp Tyr Lys Asp Thr His Val
        450                 455                 460

Thr Thr Ala Val Arg Gly Thr Ile Gly His Ile Ala Pro Glu Tyr Leu
465                 470                 475                 480

Ser Thr Gly Lys Ser Ser Glu Lys Thr Asp Val Phe Gly Tyr Gly Ile
                485                 490                 495

Met Leu Leu Glu Leu Ile Thr Gly Gln Arg Ala Phe Asp Leu Ala Arg
            500                 505                 510

Leu Ala Asn Asp Asp Val Met Leu Leu Asp Trp Val Lys Gly Leu
            515                 520                 525

Leu Lys Glu Lys Lys Leu Glu Met Leu Val Asp Pro Asp Leu Gln Ser
    530                 535                 540

Asn Tyr Thr Glu Ala Glu Val Glu Gln Leu Ile Gln Val Ala Leu Leu
545                 550                 555                 560

Cys Thr Gln Ser Ser Pro Met Glu Arg Pro Lys Met Ser Glu Val Val
                565                 570                 575

Arg Met Leu Glu Gly Asp Gly Leu Ala Glu Lys Trp Asp Glu Trp Gln
            580                 585                 590

Lys Val Glu Val Leu Arg Gln Glu Val Glu Leu Ser Ser His Pro Thr
    595                 600                 605

Ser Asp Trp Ile Leu Asp Ser Thr Asp Asn Leu His Ala Met Glu Leu
    610                 615                 620

Ser Gly Pro Arg
625

<210> SEQ ID NO 19
<211> LENGTH: 1992
<212> TYPE: DNA
<213> ORGANISM: Arabidopsis thaliana

<400> SEQUENCE: 19 atcagggtt ttaacaatga tggattttct ctgatgaggg atagttctag ggtttgtttt      60
taatctcttg aggataaaat ggaacgaaga ttaatgatcc cttgcttctt ttggttgatt     120
ctcgttttgg atttggttct cagagtctcg ggcaacgccg aaggtgatgc tctaagtgca     180
ctgaaaaaca gtttagccga ccctaataag gtgcttcaaa gttgggatgc tactcttgtt     240
actccatgta catggtttca tgttacttgc aatagcgaca atagtgttac acgtgttgac     300
cttgggaatg caaatctatc tggacagctc gtaatgcaac ttggtcagct tccaaacttg     360
cagtacttgg agcttatag caataacatt actgggacaa tcccagaaca gcttggaaat     420
ctgacggaat tggtgagctt ggatctttac ttgaacaatt taagcgggcc tattccatca     480
actctcggcc gacttaagaa actccgtttc ttgcgtctta ataacaatag cttatctgga     540
gaaattccaa ggtctttgac tgctgtcctg acgctacaag ttctggatct ctcaaacaat     600
cctctcaccg gagatattcc tgttaatggt tccttttcac ttttcactcc aatcagtttt     660
gccaacacca agttgactcc ccttcctgca tctccaccgc ctcctatctc tcctacaccg     720
ccatcacctg cagggagtaa tagaattact ggagcgattg cgggaggagt tgctgcaggt     780
gctgcacttc tatttgctgt tccggccatt gcactagctt ggtggcgaag gaaaaagccg     840
caggaccact tctttgatgt accagctgaa gaggacccag aagttcattt aggacaactg     900
aagaggtttt cattgcgtga actacaagtt gcttcggata attttagcaa caagaacata     960
ttgggtagag gtggttttgg taagttat aaaggacggt tagctgatgg tacttagtg    1020 gccgttaaaa ggctaaaaga ggagcgcacc caaggtggcg aactgcagtt ccagacagag    1080
```

-continued

```
gttgagatga ttagtatggc ggttcacaga aacttgcttc ggcttcgtgg attttgcatg    1140
actccaaccg aaagattgct tgtttatccc tacatggcta atggaagtgt tgcctcctgt    1200
ttaagagaac gtcccgagtc ccagccacca cttgattggc aaagagaca gcgtattgcg     1260 ttgggatctg caagagggct tgcgtattta catgatcatt gcgacccaaa gattattcat    1320
cgagatgtga agctgcaaa tattttgttg gatgaagagt ttgaagccgt ggttggggat     1380
tttggacttg caaaactcat ggactacaaa gacacacatg tgacaaccgc agtgcgtggg    1440
acaattggtc atatagcccc tgagtacctt tccactggaa aatcatcaga gaaaaccgat    1500
gtctttgggt atggagtcat gcttcttgag cttatcactg gacaaagggc ttttgatctt    1560
gctcgcctcg cgaatgatga tgatgtcatg ttactagact gggtgaaagg gttgttaaaa    1620
gagaagaaat tggaagcact agtagatgtt gatcttcagg gtaattacaa agacgaagaa    1680
gtggagcagc taatccaagt ggctttactc tgcactcaga gttcaccaat ggaaagaccc    1740
aaaatgtctg aagttgtaag aatgcttgaa ggagatggtt tagctgagag atgggaagag    1800
tggcaaaagg aggaaatgtt cagacaagat ttcaactacc caacccacca tccagccgtg    1860
tctggctgga tcattggcga ttccacttcc cagatcgaaa acgaataccc ctcgggtcca    1920
agataagatt cgaaacacga atgttttttc tgtattttgt ttttctctgt atttattgag    1980
ggttttagct tc                                                        1992
```

```
<210> SEQ ID NO 20
<211> LENGTH: 614
<212> TYPE: PRT
<213> ORGANISM: Arabidopsis thaliana

<400> SEQUENCE: 20
```

```
Met Glu Arg Arg Leu Met Ile Pro Cys Phe Phe Trp Leu Ile Leu Val
  1               5                  10                  15

Leu Asp Leu Val Leu Arg Val Ser Gly Asn Ala Glu Gly Asp Ala Leu
             20                  25                  30

Ser Ala Leu Lys Asn Ser Leu Ala Asp Pro Asn Lys Val Leu Gln Ser
         35                  40                  45

Trp Asp Ala Thr Leu Val Thr Pro Cys Thr Trp Phe His Val Thr Cys
     50                  55                  60

Asn Ser Asp Asn Ser Val Thr Arg Val Asp Leu Gly Asn Ala Asn Leu
 65                  70                  75                  80

Ser Gly Gln Leu Val Met Gln Leu Gly Gln Leu Pro Asn Leu Gln Tyr
                 85                  90                  95

Leu Glu Leu Tyr Ser Asn Asn Ile Thr Gly Thr Ile Pro Glu Gln Leu
            100                 105                 110

Gly Asn Leu Thr Glu Leu Val Ser Leu Asp Leu Tyr Leu Asn Asn Leu
        115                 120                 125

Ser Gly Pro Ile Pro Ser Thr Leu Gly Arg Leu Lys Lys Leu Arg Phe
    130                 135                 140

Leu Arg Leu Asn Asn Asn Ser Leu Ser Gly Glu Ile Pro Arg Ser Leu
145                 150                 155                 160

Thr Ala Val Leu Thr Leu Gln Val Leu Asp Leu Ser Asn Asn Pro Leu
                165                 170                 175

Thr Gly Asp Ile Pro Val Asn Gly Ser Phe Ser Leu Thr Pro Ile Ser
            180                 185                 190

Phe Ala Asn Thr Lys Leu Thr Pro Leu Pro Ala Ser Pro Pro Pro
        195                 200                 205

Ile Ser Pro Thr Pro Pro Ser Pro Ala Gly Ser Asn Arg Ile Thr Gly
```

```
                    210                 215                 220
Ala Ile Ala Gly Gly Val Ala Gly Ala Ala Leu Leu Phe Ala Val
225                 230                 235                 240

Pro Ala Ile Ala Leu Ala Trp Trp Arg Arg Lys Lys Pro Gln Asp His
                    245                 250                 255

Phe Phe Asp Val Pro Ala Glu Glu Asp Pro Glu Val His Leu Gly Gln
                    260                 265                 270

Leu Lys Arg Phe Ser Leu Arg Glu Leu Gln Val Ala Ser Asp Asn Phe
                275                 280                 285

Ser Asn Lys Asn Ile Leu Gly Arg Gly Gly Phe Gly Lys Val Tyr Lys
            290                 295                 300

Gly Arg Leu Ala Asp Gly Thr Leu Val Ala Val Lys Arg Leu Lys Glu
305                 310                 315                 320

Glu Arg Thr Gln Gly Gly Glu Leu Gln Phe Gln Thr Glu Val Glu Met
                    325                 330                 335

Ile Ser Met Ala Val His Arg Asn Leu Leu Arg Leu Arg Gly Phe Cys
                    340                 345                 350

Met Thr Pro Thr Glu Arg Leu Leu Val Tyr Pro Tyr Met Ala Asn Gly
                    355                 360                 365

Ser Val Ala Ser Cys Leu Arg Glu Arg Pro Glu Ser Gln Pro Pro Leu
                    370                 375                 380

Asp Trp Pro Lys Arg Gln Arg Ile Ala Leu Gly Ser Ala Arg Gly Leu
385                 390                 395                 400

Ala Tyr Leu His Asp His Cys Asp Pro Lys Ile Ile His Arg Asp Val
                    405                 410                 415

Lys Ala Ala Asn Ile Leu Leu Asp Glu Glu Phe Glu Ala Val Val Gly
                    420                 425                 430

Asp Phe Gly Leu Ala Lys Leu Met Asp Tyr Lys Asp Thr His Val Thr
                    435                 440                 445

Thr Ala Val Arg Gly Thr Ile Gly His Ile Ala Pro Glu Tyr Leu Ser
                    450                 455                 460

Thr Gly Lys Ser Ser Glu Lys Thr Asp Val Phe Gly Tyr Gly Val Met
465                 470                 475                 480

Leu Leu Glu Leu Ile Thr Gly Gln Arg Ala Phe Asp Leu Ala Arg Leu
                    485                 490                 495

Ala Asn Asp Asp Asp Val Met Leu Leu Asp Trp Val Lys Gly Leu Leu
                    500                 505                 510

Lys Glu Lys Lys Leu Glu Ala Leu Val Asp Val Asp Leu Gln Gly Asn
                515                 520                 525

Tyr Lys Asp Glu Glu Val Glu Gln Leu Ile Gln Val Ala Leu Leu Cys
            530                 535                 540

Thr Gln Ser Ser Pro Met Glu Arg Pro Lys Met Ser Glu Val Val Arg
545                 550                 555                 560

Met Leu Glu Gly Asp Gly Leu Ala Glu Arg Trp Glu Glu Trp Gln Lys
                    565                 570                 575

Glu Glu Met Phe Arg Gln Asp Phe Asn Tyr Pro Thr His His Pro Ala
                    580                 585                 590

Val Ser Gly Trp Ile Ile Gly Asp Ser Thr Ser Gln Ile Glu Asn Glu
                    595                 600                 605

Tyr Pro Ser Gly Pro Arg
            610

<210> SEQ ID NO 21
<211> LENGTH: 2034
```

<212> TYPE: DNA
<213> ORGANISM: Arabidopsis thaliana

<400> SEQUENCE: 21

| | | | | | |
|---|---|---|---|---|---|
| ttgttaacct | ctcgtaacta | aaatcttcca | tggtagtagt | aacaaagaag | accatgaaga | 60 |
| ttcaaattca | tctcctttac | tcgttcttgt | tcctctgttt | ctctactctc | actctatctt | 120 |
| ctgagcccag | aaaccctgaa | gttgaggcgt | tgataagtat | aaggaacaat | ttgcatgatc | 180 |
| ctcatggagc | tttgaacaat | tgggacgagt | tttcagttga | tccttgtagc | tgggctatga | 240 |
| tcacttgctc | tcccgacaac | ctcgtcattg | gactaggagc | gccgagccag | tctctctcgg | 300 |
| gaggtttatc | tgagtctatc | ggaaatctca | caaatctccg | acaagtgtca | ttgcaaaata | 360 |
| acaacatctc | cggcaaaatt | ccaccggagc | tcggttttct | acccaaatta | caaaccttgg | 420 |
| atctttccaa | caaccgattc | tccggtgaca | tccctgtttc | catcgaccag | ctaagcagcc | 480 |
| ttcaatatct | gagactcaac | aacaactctt | tgtctgggcc | cttccctgct | tctttgtccc | 540 |
| aaattcctca | cctctccttc | ttggacttgt | cttacaacaa | tctcagtggc | cctgttccta | 600 |
| aattcccagc | aaggacttta | aacgttgctg | gtaatccttt | gatttgtaga | agcaacccac | 660 |
| ctgagatttg | ttctggatca | atcaatgcaa | gtccactttc | tgtttctttg | agctcttcat | 720 |
| caggacgcag | gtctaataga | ttggcaatag | ctcttagtgt | aagccttggc | tctgttgtta | 780 |
| tactagtcct | tgctctcggg | tccttttgtt | ggtaccgaaa | gaaacaaaga | aggctactga | 840 |
| tccttaactt | aaacgcagat | aaacaagagg | aagggcttca | aggacttggg | aatctaagaa | 900 |
| gcttcacatt | cagagaactc | catgtttata | cagatggttt | cagttccaag | aacattctcg | 960 |
| gcgctggtgg | attcggtaat | gtgtacagag | gcaagcttgg | agatgggaca | atggtggcag | 1020 |
| tgaaacggtt | gaaggatatt | aatggaacct | caggggattc | acagtttcgt | atggagctag | 1080 |
| agatgattag | cttagctgtt | cataagaatc | tgcttcggtt | aattggttat | tgcgcaactt | 1140 |
| ctggtgaaag | gcttcttgtt | taccettaca | tgcctaatgg | aagcgtcgcc | tctaagctta | 1200 |
| aatctaaacc | ggcattggac | tggaacatga | ggaagaggat | agcaattggt | gcagcgagag | 1260 |
| gtttgttgta | tctacatgag | caatgtgatc | ccaagatcat | tcatagagat | gtaaaggcag | 1320 |
| ctaatattct | cttagacgag | tgctttgaag | ctgttgttgg | tgactttgga | ctcgcaaagc | 1380 |
| tccttaacca | tgcggattct | catgtcacaa | ctgcggtccg | tggtacggtt | ggccacattg | 1440 |
| cacctgaata | tctctccact | ggtcagtctt | ctgagaaaac | cgatgtgttt | gggttcggta | 1500 |
| tactattgct | cgagctcata | accggactga | gagctcttga | gtttggtaaa | accgttagcc | 1560 |
| agaaaggagc | tatgcttgaa | tgggtgagga | aattacatga | agagatgaaa | gtagaggaac | 1620 |
| tattggatcg | agaactcgga | actaactacg | ataagattga | agttggagag | atgttgcaag | 1680 |
| tggctttgct | atgcacacaa | tatctgccag | ctcatcgtcc | taaaatgtct | gaagttgttt | 1740 |
| tgatgcttga | aggcgatgga | ttagccgaga | tgggctgc | ttcgcataac | cattcacatt | 1800 |
| tctaccatgc | caatatctct | ttcaagacaa | tctcttctct | gtctactact | tctgtctcaa | 1860 |
| ggcttgacgc | acattgcaat | gatccaactt | atcaaatgtt | tggatcttcg | gctttcgatg | 1920 |
| atgacgatga | tcatcagcct | ttagattcct | ttgccatgga | actatccggt | ccaagataac | 1980 |
| acaatgaaag | aaagatatca | tttttacgat | ggatcaaaca | atccaatgaa | aaaa | 2034 |

<210> SEQ ID NO 22
<211> LENGTH: 650
<212> TYPE: PRT
<213> ORGANISM: Arabidopsis thaliana

<400> SEQUENCE: 22

```
Met Val Val Thr Lys Lys Thr Met Lys Ile Gln Ile His Leu Leu
1               5                   10                  15

Tyr Ser Phe Leu Phe Leu Cys Phe Ser Thr Leu Thr Leu Ser Ser Glu
            20                  25                  30

Pro Arg Asn Pro Glu Val Glu Ala Leu Ile Ser Ile Arg Asn Asn Leu
        35                  40                  45

His Asp Pro His Gly Ala Leu Asn Asn Trp Asp Glu Phe Ser Val Asp
    50                  55                  60

Pro Cys Ser Trp Ala Met Ile Thr Cys Ser Pro Asp Asn Leu Val Ile
65                  70                  75                  80

Gly Leu Gly Ala Pro Ser Gln Ser Leu Ser Gly Gly Leu Ser Glu Ser
                85                  90                  95

Ile Gly Asn Leu Thr Asn Leu Arg Gln Val Ser Leu Gln Asn Asn Asn
                100                 105                 110

Ile Ser Gly Lys Ile Pro Pro Glu Leu Gly Phe Leu Pro Lys Leu Gln
            115                 120                 125

Thr Leu Asp Leu Ser Asn Asn Arg Phe Ser Gly Asp Ile Pro Val Ser
        130                 135                 140

Ile Asp Gln Leu Ser Ser Leu Gln Tyr Leu Arg Leu Asn Asn Asn Ser
145                 150                 155                 160

Leu Ser Gly Pro Phe Pro Ala Ser Leu Ser Gln Ile Pro His Leu Ser
                165                 170                 175

Phe Leu Asp Leu Ser Tyr Asn Asn Leu Ser Gly Pro Val Pro Lys Phe
            180                 185                 190

Pro Ala Arg Thr Phe Asn Val Ala Gly Asn Pro Leu Ile Cys Arg Ser
        195                 200                 205

Asn Pro Pro Glu Ile Cys Ser Gly Ser Ile Asn Ala Ser Pro Leu Ser
    210                 215                 220

Val Ser Leu Ser Ser Ser Ser Gly Arg Arg Ser Asn Arg Leu Ala Ile
225                 230                 235                 240

Ala Leu Ser Val Ser Leu Gly Ser Val Val Ile Leu Val Leu Ala Leu
                245                 250                 255

Gly Ser Phe Cys Trp Tyr Arg Lys Lys Gln Arg Arg Leu Leu Ile Leu
            260                 265                 270

Asn Leu Asn Gly Ala Asp Lys Gln Glu Glu Gly Leu Gln Gly Leu Gly
        275                 280                 285

Asn Leu Arg Ser Phe Thr Phe Arg Glu Leu His Val Tyr Thr Asp Gly
    290                 295                 300

Phe Ser Ser Lys Asn Ile Leu Gly Ala Gly Gly Phe Gly Asn Val Tyr
305                 310                 315                 320

Arg Gly Lys Leu Gly Asp Gly Thr Met Val Ala Val Lys Arg Leu Lys
                325                 330                 335

Asp Ile Asn Gly Thr Ser Gly Asp Ser Gln Phe Arg Met Glu Leu Glu
            340                 345                 350

Met Ile Ser Leu Ala Val His Lys Asn Leu Leu Arg Leu Ile Gly Tyr
        355                 360                 365

Cys Ala Thr Ser Gly Glu Arg Leu Leu Val Tyr Pro Tyr Met Pro Asn
    370                 375                 380

Gly Ser Val Ala Ser Lys Leu Lys Ser Lys Pro Ala Leu Asp Trp Asn
385                 390                 395                 400

Met Arg Lys Arg Ile Ala Ile Gly Ala Ala Arg Gly Leu Leu Tyr Leu
                405                 410                 415

His Glu Gln Cys Asp Pro Lys Ile Ile His Arg Asp Val Lys Ala Ala
```

```
                      420              425              430
Asn Ile Leu Leu Asp Glu Cys Phe Glu Ala Val Val Gly Asp Phe Gly
                435              440              445
Leu Ala Lys Leu Leu Asn His Ala Asp Ser His Val Thr Thr Ala Val
            450              455              460
Arg Gly Thr Val Gly His Ile Ala Pro Glu Tyr Leu Ser Thr Gly Gln
465              470              475              480
Ser Ser Glu Lys Thr Asp Val Phe Gly Phe Gly Ile Leu Leu Leu Glu
                485              490              495
Leu Ile Thr Gly Leu Arg Ala Leu Glu Phe Gly Lys Thr Val Ser Gln
            500              505              510
Lys Gly Ala Met Leu Glu Trp Val Arg Lys Leu His Glu Glu Met Lys
        515              520              525
Val Glu Glu Leu Leu Asp Arg Glu Leu Gly Thr Asn Tyr Asp Lys Ile
        530              535              540
Glu Val Gly Glu Met Leu Gln Val Ala Leu Leu Cys Thr Gln Tyr Leu
545              550              555              560
Pro Ala His Arg Pro Lys Met Ser Glu Val Val Leu Met Leu Glu Gly
                565              570              575
Asp Gly Leu Ala Glu Arg Trp Ala Ala Ser His Asn His Ser His Phe
                580              585              590
Tyr His Ala Asn Ile Ser Phe Lys Thr Ile Ser Ser Leu Ser Thr Thr
            595              600              605
Ser Val Ser Arg Leu Asp Ala His Cys Asn Asp Pro Thr Tyr Gln Met
        610              615              620
Phe Gly Ser Ser Ala Phe Asp Asp Asp Asp His Gln Pro Leu Asp
625              630              635              640
Ser Phe Ala Met Glu Leu Ser Gly Pro Arg
                645              650

<210> SEQ ID NO 23
<211> LENGTH: 1976
<212> TYPE: DNA
<213> ORGANISM: Arabidopsis thaliana

<400> SEQUENCE: 23
tttaaaaacc ttgctagttc tcaattctca tgactttgct tttagtctta gaagtggaaa      60
atggaacatg gatcatcccg tggctttatt tggctgattc tatttctcga ttttgtttcc     120
agagtcaccg gaaaaacaca agttgatgct ctcattgctc taagaagcag tttatcatca     180
ggtgaccata caaacaatat actccaaagc tggaatgcca ctcacgttac tccatgttca     240
tggtttcatg ttacttgcaa tactgaaaac agtgttactc gtcttgacct ggggagtgct     300
aatctatctg gagaactggt gccacagctt gctcagcttc aaatttgca gtacttggaa      360
ctttttaaca ataatattac tggggagata cctgaggagc ttggcgactt gatggaacta     420
gtaagcttgg acctttttgc aaacaacata agcggtccca tcccttcctc tcttggcaaa     480
ctaggaaaac tccgcttctt gcgtctttat aacaacagct tatctggaga aattccaagg     540
tctttgactg ctctgccgct ggatgttctt gatatctcaa caatcggct cagtggagat      600
attcctgtta atggttcctt ttcgcagttc acttctatga gttttgccaa taataaatta     660
aggccgcgac ctgcatctcc ttcaccatca ccttcaggaa cgtctgcagc aatagtagtg     720
ggagttgctg cgggtgcagc acttctattt gcgcttgctt ggtggctgag aagaaaactg     780
cagggtcact ttcttgatgt acctgctgaa gaagacccag aggtttattt aggacaattt     840
```

-continued

```
aaaaggttct ccttgcgtga actgctagtt gctacagaga aatttagcaa aagaaatgta    900
ttgggcaaag gacgttttgg tatattgtat aaaggacgtt tagctgatga cactctagtg    960
gctgtgaaac ggctaaatga agaacgtacc aagggtgggg aactgcagtt tcaaaccgaa   1020
gttgagatga tcagtatggc cgttcatagg aacttgcttc ggcttcgtgg cttttgcatg   1080
actccaactg aaagattact tgtttatccc tacatggcta atggaagtgt tgcttcttgt   1140
ttaagagagc gtcctgaagg caatccagcc cttgactggc aaaaagaaa gcatattgct    1200
ctgggatcag caagggggct cgcatattta cacgatcatt gcgaccaaaa gatcattcac   1260
ctggatgtga agctgcaaa tatactgtta gatgaagagt ttgaagctgt tgttggagat    1320
tttgggctag caaaattaat gaattataac gactcccatg tgacaactgc tgtacggggt   1380
acgattggcc atatagcgcc cgagtacctc tcgacaggaa atcttctga aagactgat    1440
gttttttgggt acggggtcat gcttctcgag ctcatcactg gacaaaaggc tttcgatctt   1500
gctcggcttg caaatgatga tgatatcatg ttactcgact gggtgaaaga ggttttgaaa   1560
gagaagaagt tggaaagcct tgtggatgca gaactcgaag gaaagtacgt ggaaacagaa   1620
gtggagcagc tgatacaaat ggctctgctc tgcactcaaa gttctgcaat ggaacgtcca   1680
aagatgtcag aagtagtgag aatgctggaa ggagatggtt tagctgagag atgggaagaa   1740
tggcaaaagg aggagatgcc aatacatgat tttaactatc aagcctatcc tcatgctggc   1800
actgactggc tcatccccta ttccaattcc cttatcgaaa acgattaccc ctcggggcca   1860
agataacctt ttagaaaggg tcatttcttg tgggttcttc aacaagtata tatataggta   1920
gtgaagttgt aagaagcaaa accccacatt cacctttgaa tatcactact ctataa       1976
```

<210> SEQ ID NO 24
<211> LENGTH: 603
<212> TYPE: PRT
<213> ORGANISM: Arabidopsis thaliana

<400> SEQUENCE: 24

```
Met Glu His Gly Ser Ser Arg Gly Phe Ile Trp Leu Ile Leu Phe Leu
1               5                   10                  15

Asp Phe Val Ser Arg Val Thr Gly Lys Thr Gln Val Asp Ala Leu Ile
            20                  25                  30

Ala Leu Arg Ser Ser Leu Ser Ser Gly Asp His Thr Asn Asn Ile Leu
        35                  40                  45

Gln Ser Trp Asn Ala Thr His Val Thr Pro Cys Ser Trp Phe His Val
    50                  55                  60

Thr Cys Asn Thr Glu Asn Ser Val Thr Arg Leu Asp Leu Gly Ser Ala
65                  70                  75                  80

Asn Leu Ser Gly Glu Leu Val Pro Gln Leu Ala Gln Leu Pro Asn Leu
                85                  90                  95

Gln Tyr Leu Glu Leu Phe Asn Asn Ile Thr Gly Glu Ile Pro Glu
            100                 105                 110

Glu Leu Gly Asp Leu Met Glu Leu Val Ser Leu Asp Leu Phe Ala Asn
        115                 120                 125

Asn Ile Ser Gly Pro Ile Pro Ser Ser Leu Gly Lys Leu Gly Lys Leu
    130                 135                 140

Arg Phe Leu Arg Leu Tyr Asn Asn Ser Leu Ser Gly Glu Ile Pro Arg
145                 150                 155                 160

Ser Leu Thr Ala Leu Pro Leu Asp Val Leu Asp Ile Ser Asn Asn Arg
                165                 170                 175

Leu Ser Gly Asp Ile Pro Val Asn Gly Ser Phe Ser Gln Phe Thr Ser
```

```
                180             185             190
Met Arg Phe Ala Asn Asn Lys Leu Arg Pro Arg Pro Ala Ser Pro Ser
            195             200             205
Pro Ser Pro Ser Gly Gly Thr Ser Ala Ala Ile Val Val Gly Val Ala
        210             215             220
Ala Gly Ala Ala Leu Leu Phe Ala Leu Ala Trp Trp Leu Arg Arg Lys
225             230             235             240
Leu Gln Gly His Phe Leu Asp Val Pro Ala Ala Glu Glu Asp Pro Glu
            245             250             255
Val Tyr Leu Gly Gln Phe Lys Arg Phe Ser Leu Arg Glu Leu Leu Val
        260             265             270
Ala Thr Glu Lys Phe Ser Lys Arg Asn Val Leu Gly Lys Gly Arg Phe
    275             280             285
Gly Ile Leu Tyr Lys Gly Arg Leu Ala Asp Asp Thr Leu Val Ala Val
        290             295             300
Lys Arg Leu Asn Glu Glu Arg Thr Lys Gly Gly Glu Leu Gln Phe Gln
305             310             315             320
Thr Glu Val Glu Met Ile Ser Met Ala Val His Arg Asn Leu Leu Arg
            325             330             335
Leu Arg Gly Phe Cys Met Thr Pro Thr Glu Arg Leu Leu Val Tyr Pro
        340             345             350
Tyr Met Ala Asn Gly Ser Val Ala Ser Cys Leu Arg Glu Arg Pro Glu
        355             360             365
Gly Asn Pro Ala Leu Asp Trp Pro Lys Arg Lys His Ile Ala Leu Gly
    370             375             380
Ser Ala Arg Gly Leu Ala Tyr Leu His Asp His Cys Asp Gln Lys Ile
385             390             395             400
Ile His Leu Asp Val Lys Ala Ala Asn Ile Leu Leu Asp Glu Glu Phe
            405             410             415
Glu Ala Val Val Gly Asp Phe Gly Leu Ala Lys Leu Met Asn Tyr Asn
        420             425             430
Asp Ser His Val Thr Thr Ala Val Arg Gly Thr Ile Gly His Ile Ala
        435             440             445
Pro Glu Tyr Leu Ser Thr Gly Lys Ser Ser Glu Lys Thr Asp Val Phe
    450             455             460
Gly Tyr Gly Val Met Leu Leu Glu Leu Ile Thr Gly Gln Lys Ala Phe
465             470             475             480
Asp Leu Ala Arg Leu Ala Asn Asp Asp Ile Met Leu Leu Asp Trp
            485             490             495
Val Lys Glu Val Leu Lys Glu Lys Lys Leu Glu Ser Leu Val Asp Ala
        500             505             510
Glu Leu Glu Gly Lys Tyr Val Glu Thr Glu Val Glu Gln Leu Ile Gln
        515             520             525
Met Ala Leu Leu Cys Thr Gln Ser Ser Ala Met Glu Arg Pro Lys Met
    530             535             540
Ser Glu Val Val Arg Met Leu Glu Gly Asp Gly Leu Ala Glu Arg Trp
545             550             555             560
Glu Glu Trp Gln Lys Glu Glu Met Pro Ile His Asp Phe Asn Tyr Gln
            565             570             575
Ala Tyr Pro His Ala Gly Thr Asp Trp Leu Ile Pro Tyr Ser Asn Ser
        580             585             590
Leu Ile Glu Asn Asp Tyr Pro Ser Gly Pro Arg
    595             600
```

<210> SEQ ID NO 25
<211> LENGTH: 1982
<212> TYPE: DNA
<213> ORGANISM: Arabidopsis thaliana

<400> SEQUENCE: 25

| | | | | | |
|---|---|---|---|---|---|
| taataaacct | ctaataataa | tggctttgct | tttactctga | tgacaagttc | aaaaatggaa | 60 |
| caaagatcac | tcctttgctt | cctttatctg | ctcctactat | tcaatttcac | tctcagagtc | 120 |
| gctggaaacg | ctgaaggtga | tgctttgact | cagctgaaaa | acagtttgtc | atcaggtgac | 180 |
| cctgcaaaca | atgtactcca | aagctgggat | gctactcttg | ttactccatg | tacttggttt | 240 |
| catgttactt | gcaatcctga | gaataaagtt | actcgtgttg | accttgggaa | tgcaaaacta | 300 |
| tctggaaagt | tggttccaga | acttggtcag | cttttaaact | tgcagtactt | ggagctttat | 360 |
| agcaataaca | ttacagggga | gatacctgag | gagcttggcg | acttggtgga | actagtaagc | 420 |
| ttggatcttt | acgcaaacag | cataagcggt | cccatcccttt | cgtctcttgg | caaactagga | 480 |
| aaactccggt | tcttgcgtct | taacaacaat | agcttatcag | gggaaattcc | aatgactttg | 540 |
| acttctgtgc | agctgcaagt | tctggatatc | tcaaacaatc | ggctcagtgg | agatattcct | 600 |
| gttaatggtt | cttttcgct | cttcactcct | atcagttttg | cgaataatag | cttaacggat | 660 |
| cttcccgaac | ctccgcctac | ttctacctct | cctacgccac | caccaccttc | agggggggcaa | 720 |
| atgactgcag | caatagcagg | gggagttgct | gcaggtgcag | cacttctatt | tgctgttcca | 780 |
| gccattgcgt | ttgcttggtg | gctcagaaga | aaaccacagg | accactttt | tgatgtacct | 840 |
| gctgaagaag | acccagaggt | tcatttagga | caactcaaaa | ggtttacctt | gcgtgaactg | 900 |
| ttagttgcta | ctgataactt | tagcaataaa | aatgtattgg | gtagaggtgg | ttttggtaaa | 960 |
| gtgtataaag | gacgtttagc | cgatggcaat | ctagtggctg | tcaaaaggct | aaaagaagaa | 1020 |
| cgtaccaagg | gtggggaact | gcagtttcaa | accgaagttg | agatgatcag | tatggccgtt | 1080 |
| cataggaact | tgcttcggct | tcgtggctt | tgcatgactc | caactgaaag | attacttgtt | 1140 |
| tatccctaca | tggctaatgg | aagtgttgct | tcttgtttaa | gagagcgtcc | tgaaggcaat | 1200 |
| ccagcacttg | attggccaaa | aagaaagcat | attgctctgg | gatcagcaag | ggggcttgcg | 1260 |
| tatttacatg | atcattgcga | ccaaaaaatc | attcaccggg | atgttaaagc | tgctaatata | 1320 |
| ttgttagatg | aagagtttga | agctgttgtt | ggagattttg | ggctcgcaaa | attaatgaat | 1380 |
| tataatgact | cccatgtgac | aactgctgta | cgcggtacaa | ttggccatat | agcgcccgag | 1440 |
| tacctctcga | caggaaaatc | ttctgagaag | actgatgttt | ttgggtacgg | ggtcatgctt | 1500 |
| ctcgagctca | tcactggaca | aaaggctttc | gatcttgctc | ggcttgcaaa | tgatgatgat | 1560 |
| atcatgttac | tcgactgggt | gaaagaggtt | ttgaaagaga | agaagttgga | aagccttgtg | 1620 |
| gatgcagaac | tcgaaggaaa | gtacgtggaa | acagaagtgg | agcagctgat | acaaatggct | 1680 |
| ctgctctgca | ctcaaagttc | tgcaatgaa | cgtccaaaga | tgtcagaagt | agtgagaatg | 1740 |
| ctggaaggag | atggtttagc | tgagagatgg | gaagaatggc | aaaaggagga | gatgccaata | 1800 |
| catgatttta | actatcaagc | ctatcctcat | gctggcactg | actggctcat | cccctattcc | 1860 |
| aattccctta | tcgaaaacga | ttacccctcg | ggtccaagat | aaccttttag | aaagggtctt | 1920 |
| ttcttgtggg | ttcttcaaca | agtatatata | tagattggtg | aagttttaag | atgcaaaaaa | 1980 |
| aa | | | | | | 1982 |

<210> SEQ ID NO 26
<211> LENGTH: 616
<212> TYPE: PRT

<213> ORGANISM: Arabidopsis thaliana

<400> SEQUENCE: 26

```
Met Glu Gln Arg Ser Leu Leu Cys Phe Leu Tyr Leu Leu Leu Phe
1               5                   10                  15

Asn Phe Thr Leu Arg Val Ala Gly Asn Ala Glu Gly Asp Ala Leu Thr
            20                  25                  30

Gln Leu Lys Asn Ser Leu Ser Ser Gly Asp Pro Ala Asn Asn Val Leu
        35                  40                  45

Gln Ser Trp Asp Ala Thr Leu Val Thr Pro Cys Thr Trp Phe His Val
    50                  55                  60

Thr Cys Asn Pro Glu Asn Lys Val Thr Arg Val Asp Leu Gly Asn Ala
65                  70                  75                  80

Lys Leu Ser Gly Lys Leu Val Pro Glu Leu Gly Gln Leu Leu Asn Leu
                85                  90                  95

Gln Tyr Leu Glu Leu Tyr Ser Asn Asn Ile Thr Gly Glu Ile Pro Glu
            100                 105                 110

Glu Leu Gly Asp Leu Val Glu Leu Val Ser Leu Asp Leu Tyr Ala Asn
        115                 120                 125

Ser Ile Ser Gly Pro Ile Pro Ser Ser Leu Gly Lys Leu Gly Lys Leu
    130                 135                 140

Arg Phe Leu Arg Leu Asn Asn Asn Ser Leu Ser Gly Glu Ile Pro Met
145                 150                 155                 160

Thr Leu Thr Ser Val Gln Leu Gln Val Leu Asp Ile Ser Asn Asn Arg
                165                 170                 175

Leu Ser Gly Asp Ile Pro Val Asn Gly Ser Phe Ser Leu Phe Thr Pro
            180                 185                 190

Ile Ser Phe Ala Asn Asn Ser Leu Thr Asp Leu Pro Glu Pro Pro
        195                 200                 205

Thr Ser Thr Ser Pro Thr Pro Pro Pro Ser Gly Gly Gln Met Thr
    210                 215                 220

Ala Ala Ile Ala Gly Gly Val Ala Gly Ala Ala Leu Leu Phe Ala
225                 230                 235                 240

Val Pro Ala Ile Ala Phe Ala Trp Trp Leu Arg Arg Lys Pro Gln Asp
                245                 250                 255

His Phe Phe Asp Val Pro Gly Ala Glu Glu Asp Pro Glu Val His Leu
            260                 265                 270

Gly Gln Leu Lys Arg Phe Thr Leu Arg Glu Leu Leu Val Ala Thr Asp
        275                 280                 285

Asn Phe Ser Asn Lys Asn Val Leu Gly Arg Gly Gly Phe Gly Lys Val
    290                 295                 300

Tyr Lys Gly Arg Leu Ala Asp Gly Asn Leu Val Ala Val Lys Arg Leu
305                 310                 315                 320

Lys Glu Glu Arg Thr Lys Gly Gly Glu Leu Gln Phe Gln Thr Glu Val
                325                 330                 335

Glu Met Ile Ser Met Ala Val His Arg Asn Leu Leu Arg Leu Arg Gly
            340                 345                 350

Phe Cys Met Thr Pro Thr Glu Arg Leu Leu Val Tyr Pro Tyr Met Ala
        355                 360                 365

Asn Gly Ser Val Ala Ser Cys Leu Arg Glu Arg Pro Glu Gly Asn Pro
    370                 375                 380

Ala Leu Asp Trp Pro Lys Arg Lys His Ile Ala Leu Gly Ser Ala Arg
385                 390                 395                 400

Gly Leu Ala Tyr Leu His Asp His Cys Asp Gln Lys Ile Ile His Arg
```

```
                       405                 410                 415
Asp Val Lys Ala Ala Asn Ile Leu Leu Asp Glu Glu Phe Glu Ala Val
            420                 425                 430

Val Gly Asp Phe Gly Leu Ala Lys Leu Met Asn Tyr Asn Asp Ser His
        435                 440                 445

Val Thr Thr Ala Val Arg Gly Thr Ile Gly His Ile Ala Pro Glu Tyr
    450                 455                 460

Leu Ser Thr Gly Lys Ser Ser Glu Lys Thr Asp Val Phe Gly Tyr Gly
465                 470                 475                 480

Val Met Leu Leu Glu Leu Ile Thr Gly Gln Lys Ala Phe Asp Leu Ala
                485                 490                 495

Arg Leu Ala Asn Asp Asp Asp Ile Met Leu Leu Asp Trp Val Lys Glu
            500                 505                 510

Val Leu Lys Glu Lys Lys Leu Glu Ser Leu Val Asp Ala Glu Leu Glu
        515                 520                 525

Gly Lys Tyr Val Glu Thr Glu Val Glu Gln Leu Ile Gln Met Ala Leu
    530                 535                 540

Leu Cys Thr Gln Ser Ser Ala Met Glu Arg Pro Lys Met Ser Glu Val
545                 550                 555                 560

Val Arg Met Leu Glu Gly Asp Gly Leu Ala Glu Arg Trp Glu Glu Trp
                565                 570                 575

Gln Lys Glu Glu Met Pro Ile His Asp Phe Asn Tyr Gln Ala Tyr Pro
            580                 585                 590

His Ala Gly Thr Asp Trp Leu Ile Pro Tyr Ser Asn Ser Leu Ile Glu
        595                 600                 605

Asn Asp Tyr Pro Ser Gly Pro Arg
    610                 615

<210> SEQ ID NO 27
<211> LENGTH: 1971
<212> TYPE: DNA
<213> ORGANISM: Arabidopsis thaliana

<400> SEQUENCE: 27
ctgcacctta gagattaata ctctcaagaa aaacaagttt tgattcggac aaagatgttg      60
caaggaagaa gagaagcaaa aaagagttat gctttgttct cttcaacttt cttcttcttc     120
tttatctgtt ttctttcttc ttcttctgca gaactcacag acaaagttgt tgccttaata     180
ggaatcaaaa gctcactgac tgatcctcat ggagttctaa tgaattggga tgacacagca     240
gttgatccat gtagctggaa catgatcact tgttctgatg gttttgtcat aaggctagaa     300
gctccaagcc aaaacttatc aggaactctt tcatcaagta ttggaaattt aacaaatctt     360
caaactgtat acaggttatt gcagaacaat tacataacag gaaacatccc tcatgagatt     420
gggaaattga tgaaactcaa aacacttgat ctctctacca ataacttcac tggtcaaatc     480
ccattcactc tttcttactc caaaaatctt cacaggaggg ttaataataa cagcctgaca     540
ggaacaattc ctagctcatt ggcaaacatg acccaactca ctttttttgga tttgtcgtat     600 aataacttga gtggaccagt tccaagatca cttgccaaaa cattcaatgt tatgggcaat     660
tctcagattt gtccaacagg aactgagaaa gactgtaatg ggactcagcc taagccaatg     720
tcaatcacct tgaacagttc tcaaagaact aaaaaccgga aatcgcggt agtcttcggt      780 gtaagcttga catgtgtttg cttgttgatc attggctttg gttttcttct tggtggagaa     840
agaagacata caaacaagt attattcttt gacattaatg agcaaaacaa ggaagaaatg     900
tgtctaggga atctaaggag gtttaatttc aaagaacttc aatccgcaac tagtaacttc     960
```

```
agcagcaaga atctggtcgg aaaaggaggg tttggaaatg tgtataaagg ttgtcttcat    1020
gatggaagta tcatcgcggt gaagagatta aggatataa acaatggtgg tggagaggtt    1080
cagtttcaga cagagcttga atgataagc cttgccgtcc accggaatct cctccgctta    1140
tacggtttct gtactacttc ctctgaacgg cttctcgttt atccttacat gtccaatggc    1200
agtgtcgctt ctcgtctcaa agctaaaccg gtattggatt ggggcacaag aaagcgaata    1260
gcattaggag caggaagagg gttgctgtat ttgcatgagc aatgtgatcc aaagatcatt    1320
caccgtgatg tcaaagctgc gaacatactt cttgacgatt actttgaagc tgttgtcgga    1380
gatttcgggt tggctaagct tttggatcat gaggagtcgc atgtgacaac cgccgtgaga    1440
ggaacagtgg gtcacattgc acctgagtat ctctcaacag acaatcttc tgagaagaca     1500 gatgtgttcg gtttcgggat tcttcttctc gaattgatta ctggattgag agctcttgaa    1560
ttcggaaaag cagcaaacca aagaggagcg atacttgatt gggtaaagaa actacaacaa    1620
gagaagaagc tagaacagat agtagacaag gatttgaaga gcaactacga tagaatagaa    1680
gtggaagaaa tggttcaagt ggctttgctt tgtacacagt atcttcccat tcaccgtcct    1740
aagatgtctg aagttgtgag aatgcttgaa ggcgatggtc ttgttgagaa atgggaagct    1800
tcttctcaga gagcagaaac caatagaagt tacagtaaac ctaacgagtt ttcttcctct    1860
gaacgttatt cggatcttac agatgattcc tcggtgctgg ttcaagccat ggagttatca    1920
ggtccaagat gacaagagaa actatatgaa tggctttggg tttgtaaaaa a             1971

<210> SEQ ID NO 28
<211> LENGTH: 625
<212> TYPE: PRT
<213> ORGANISM: Arabidopsis thaliana

<400> SEQUENCE: 28

Met Leu Gln Gly Arg Arg Glu Ala Lys Lys Ser Tyr Ala Leu Phe Ser
1               5                   10                  15

Ser Thr Phe Phe Phe Phe Ile Cys Phe Leu Ser Ser Ser Ser Ala
            20                  25                  30

Glu Leu Thr Asp Lys Val Val Ala Leu Gly Ile Lys Ser Ser Leu
        35                  40                  45

Thr Asp Pro His Gly Val Leu Met Asn Trp Asp Thr Ala Val Asp
    50                  55                  60

Pro Cys Ser Trp Asn Met Ile Thr Cys Ser Asp Gly Phe Val Ile Arg
65                  70                  75                  80

Leu Glu Ala Pro Ser Gln Asn Leu Ser Gly Thr Leu Ser Ser Ile
            85                  90                  95

Gly Asn Leu Thr Asn Leu Gln Thr Val Tyr Arg Leu Leu Gln Asn Asn
            100                 105                 110

Tyr Ile Thr Gly Asn Ile Pro His Glu Ile Gly Lys Leu Met Lys Leu
        115                 120                 125

Lys Thr Leu Asp Leu Ser Thr Asn Asn Phe Thr Gly Gln Ile Pro Phe
    130                 135                 140

Thr Leu Ser Tyr Ser Lys Asn Leu His Arg Arg Val Asn Asn Asn Ser
145                 150                 155                 160
```

-continued

```
Leu Thr Gly Thr Ile Pro Ser Ser Leu Ala Asn Met Thr Gln Leu Thr
                165                 170                 175

Phe Leu Asp Leu Ser Tyr Asn Asn Leu Ser Gly Pro Val Pro Arg Ser
            180                 185                 190

Leu Ala Lys Thr Phe Asn Val Met Gly Asn Ser Gln Ile Cys Pro Thr
        195                 200                 205

Gly Thr Glu Lys Asp Cys Asn Gly Thr Gln Pro Lys Pro Met Ser Ile
    210                 215                 220

Thr Leu Asn Ser Ser Gln Arg Thr Lys Asn Arg Lys Ile Ala Val Val
225                 230                 235                 240

Phe Gly Val Ser Leu Thr Cys Val Cys Leu Leu Ile Ile Gly Phe Gly
                245                 250                 255

Phe Leu Leu Trp Trp Arg Arg Arg His Asn Lys Gln Val Leu Phe Phe
            260                 265                 270

Asp Ile Asn Glu Gln Asn Lys Glu Glu Met Cys Leu Gly Asn Leu Arg
        275                 280                 285

Arg Phe Asn Phe Lys Glu Leu Gln Ser Ala Thr Ser Asn Phe Ser Ser
    290                 295                 300

Lys Asn Leu Val Gly Lys Gly Phe Gly Asn Val Tyr Lys Gly Cys
305                 310                 315                 320

Leu His Asp Gly Ser Ile Ile Ala Val Lys Arg Leu Lys Asp Ile Asn
                325                 330                 335

Asn Gly Gly Gly Glu Val Gln Phe Gln Thr Glu Leu Glu Met Ile Ser
            340                 345                 350

Leu Ala Val His Arg Asn Leu Leu Arg Leu Tyr Gly Phe Cys Thr Thr
        355                 360                 365

Ser Ser Glu Arg Leu Leu Val Tyr Pro Tyr Met Ser Asn Gly Ser Val
    370                 375                 380

Ala Ser Arg Leu Lys Ala Lys Pro Val Leu Asp Trp Gly Thr Arg Lys
385                 390                 395                 400

Arg Ile Ala Leu Gly Ala Gly Arg Gly Leu Leu Tyr Leu His Glu Gln
                405                 410                 415

Cys Asp Pro Lys Ile Ile His Arg Asp Val Lys Ala Ala Asn Ile Leu
            420                 425                 430

Leu Asp Asp Tyr Phe Glu Ala Val Val Gly Asp Phe Gly Leu Ala Lys
        435                 440                 445

Leu Leu Asp His Glu Glu Ser His Val Thr Thr Ala Val Arg Gly Thr
    450                 455                 460

Val Gly His Ile Ala Pro Glu Tyr Leu Ser Thr Gly Gln Ser Ser Glu
465                 470                 475                 480

Lys Thr Asp Val Phe Gly Phe Gly Ile Leu Leu Leu Glu Leu Ile Thr
                485                 490                 495

Gly Leu Arg Ala Leu Glu Phe Gly Lys Ala Ala Asn Gln Arg Gly Ala
            500                 505                 510

Ile Leu Asp Trp Val Lys Lys Leu Gln Gln Glu Lys Lys Leu Glu Gln
        515                 520                 525

Ile Val Asp Lys Asp Leu Lys Ser Asn Tyr Asp Arg Ile Glu Val Glu
    530                 535                 540

Glu Met Val Gln Val Ala Leu Leu Cys Thr Gln Tyr Leu Pro Ile His
545                 550                 555                 560

Arg Pro Lys Met Ser Glu Val Val Arg Met Leu Glu Gly Asp Gly Leu
                565                 570                 575

Val Glu Lys Trp Glu Ala Ser Ser Gln Arg Ala Glu Thr Asn Arg Ser
            580                 585                 590
```

```
Tyr Ser Lys Pro Asn Glu Phe Ser Ser Ser Glu Arg Tyr Ser Asp Leu
        595                 600                 605

Thr Asp Asp Ser Ser Val Leu Val Gln Ala Met Glu Leu Ser Gly Pro
    610                 615                 620

Arg
625
```

METHOD TO INCREASE PATHOGEN RESISTANCE IN PLANTS

This application is the U.S. National Phase and a continuation-in-part application of, and Applicants claim priority from, International Application Number PCT/NL2005/000540 filed 25 Jul. 2005 and European Patent Application bearing Serial No. EP 04077173.5 filed 28 Jul. 2004, which are incorporated herein by reference.

INCORPORATION OF SEQUENCE LISTING

Incorporated herein by reference in its entirety is the Sequence Listing for the application. The Sequence Listing is disclosed on a computer-readable ASCII text file titled, "Sequence17DEC2009_294-270CIP.txt" created on Dec. 17, 2009. The sequence ASCII text file is 111 kb in size.

BACKGROUND OF THE INVENTION

This invention relates to the field of plant diseases, more specifically to improving the resistance of plants to pathogens, more specifically to increase the induced resistance mechanism.

INTRODUCTION

When plants encounter pathogens, resistance mechanisms are activated that can prevent infection, aid recovery from disease and prevent even future infections. A common feature of resistance is that it is induced in response to a first initial encounter or attack by pathogens.

It has recently become clear that plant resistance proteins when activated by interaction with pathogen-derived elicitor molecules are capable of inducing a signal transduction pathway. It has been established that some interactions at least partly use a common pathway (Science, 1997, 278, 1963-1965). In this publication the NDR1 locus has been shown to be required for resistance to the bacterial pathogen *Pseudomonas syringae* pv. tomato and to be induced by the fungal pathogen *Peronospora parasitica*. Similarly Parker, J. E. et al. (The Plant Cell, 1996, 8, 2033-2046) have shown that the product encoded by the EDS1 locus in *Arabidopsis thaliana* also has a key function in the signal transduction pathway after infection with *Peronospora parasitica*, but not after infection with *Pseudomonas syringae* pv glycinae.

Many different research groups introduced genes coding for such elicitor sensor or receptor molecules into plants in order to make these transformed plants resistant to pathogen infection. In general, these elicitor-receptors are only able to recognize one pathogen, or even one virulent strain of a pathogen species. Moreover, the pathogen can adapt rapidly and easily towards this form of selection pressure and small modifications of the elicitor molecule proved to be sufficient to render the plant unable to recognize the pathogen. Although there is a large number of possible sensor molecules, the number of genes involved in transmitting the signal is very small, and consists of evolutionary conserved proteins.

Much broader levels of perception and of broad-spectrum disease resistance responses are mediated by perception of pathogen molecules, which are conserved in a large variety of pathogens. These pathogen-associated molecular patterns (PAMPs) are recognized by plant receptors like the flagellin peptide receptor FLS2 (Mol Cell., 2000, 5, 1003-1011), or the receptor for elongation factor Tu (The Plant Cell, 2004, 16, 3496-3507).

The intracellular warning signals transmitted by the elicitor-receptors provide a suitable target for basal resistance manipulation (Trends in Genetics, 2000, 16, 449-450). The intracellular signalling cascades at the site of primary invasion are similar and conserved in the majority of plant species. Modulating the basal signalling in transgenic plants to a higher level (see WO99/45129) resulted in an induced basal resistance level.

The continuous activation of the primary defence signal seems therefore the strategy of choice to increase resistance at the first defence barrier. However, constant overstimulation of this level of resistance is undesired due to the fitness costs involved (Trends in Plant Science, 2002, 7, 61-67).

The second resistance barrier is provided by a process of induced resistance (IR) responses throughout the whole plant. This defence barrier is essential in the fight against pathogens. It can be roughly divided in two different processes:

(a) the release of alarm signals from the primary site of infection and the systemic spreading of signals throughout the plant;

(b) the perception of these signals in the different organs and the activation of induced resistance (IR).

Perception of the alarm signals and downstream processing that yield to the activated resistance are processes which can be different among the various alarm signals.

Salicylic acid (SA) has since long been recognised as being one of the major alarm signals. It is also acting as a hormone involved in plant developmental processes like senescence and thermogenesis (Plant Physiol., 1992, 99, 799-803; Science, 1987, 237, 1601-1602; PNAS, 1989, 86, 2214-2218). In the animal medical field salicylic acid (and its derivatives) has since long been used against inflammation induced fever. Rising temperatures in the human body can be lowered by applying salicylic acid that mediates its effect through COX2, a cyclo-oxygenase. The link between resistance in inflammation and disease, both in animal systems (Journal of Endocrinology, 2003, 178, 1-4) and in plant systems is mediated by the activity of COX2. COX2 has clear homologues in the plant kingdom, like Piox in tobacco (The Plant Cell, 1998, 10, 1523-1537), or pCa-COX1 from pepper, which expression pattern is strongly and quickly induced upon pathogen invasion (J. Exp. Botany, 2002, 53, 383-385). Here we define the plant homologues of these cyclo-oxygenase homologues as perception molecules (receptors) of salicylic acid. Binding of SA to cyclo-oxygenase results in modification of its enzymatic activity, resulting in changes in intracellular (lipid) processes that finally result in SA-mediated induction of resistance within the plant.

Another molecule involved in mediating the SA response towards resistance in plants is SABP2. SABP2 binds salicylic acid with high affinity (PNAS, 2003, 100, 16101-16106). SABP2 hydrolase enzymatic activity is thereby modified, resulting in changes in intracellular lipid processes that finally result in SA-mediated induction of plant resistance. It has recently become known that SABP2 is a methyl esterase that modifies MeSA into SA activating SAR and that SA inhibits this reaction in a feedback loop (PNAS, 2005, 102, 1773-1778). Therefore this molecule is presumably miss defined as receptor.

The brassinosteroid receptor BRI1 (BRassinosteroid Insensitive 1) is a LRR (leucine rich repeats containing) transmembrane receptor kinase (Cell, 1997, 90, 929-938). It belongs to a small family in *Arabidopsis* comprising: BMI1 (At4g39400); BRL1 (At1g55610), BRL2 (At2g01950) and BRL3 (At3g13380) (Development, 2004, 131, 5341-5351). BRI1 and homologues are not only directly involved in steroid perception (Nature 2005, 433, 167-171), but also bind with high affinity to systemin (pro-systemin homologue from *Arabidopsis*: At2g22940), a peptide hormone involved in systemic signalling of resistance responses (PNAS, 2002, 99, 9090-9092). Downstream intracellular pathways for plant steroid signalling have been described (Bioassays, 2001, 23, 1028-1036; Trends in Plant Science, 2004, 9, 91-95).

Another family of receptors involved in the brassinosteroid perception is defined by the RKS (Receptor Kinase-like SERK; Development, 1997, 124, 2049-2062) gene products (WO 04/007712, i.e., U.S. patent application Ser. No. 10/521, 518, having a publication number US 2006-0265783, which is incorporated herein by reference). In particular, page 1, lines 9-35 of the WO 04/007712 (which corresponds to paragraph [0001] of US patent publication 20060265783) reference is incorporated herein by reference. See below.

The different domains of RKS gene products essentially have the following functions: The first domain of the predicted protein structure at the N-terminal end consists of a signal sequence, involved in targeting the protein towards the plasma membrane. Protein cleavage removes this sequence from the final mature protein product (Jain et al. 1994, J. Biol. Chemistry 269: 16306-16310). The second domain consists of different numbers of leucine zipper motifs, and is likely to be involved in protein protein dimerization. The next domain contains a conserved pair of cystein residues, involved in disulphate bridge formation. The next domain consists of 5 (or in the case of RKS3 only 4) leucine rich repeats (LRRs) shown in a gray colour, likely to be involved in ligand binding (Kobe and Deisenhofer 1994, TIBS 19: 415-420). This domain is again bordered by a domain containing a conserved pair of cystein residues involved in disulphate bridge formation often followed by a serine/proline rich region. The next domain displays all the characteristics of a single transmembrane domain. At the predicted cytoplasmic site of protein a domain is situated with unknown function, followed by a domain with serine/threonine kinase activity (Schmidt et al. 1997, Development 124: 2049-2062, WO 01/29240). The kinase domain is followed by a domain with unknown function whereas at the C-terminal end of the protein part of a leucine rich repeat is positioned, probably involved in protein-protein interactions.

These RKS gene products are also involved in mediating brassinosteroid signalling in plants and appear to form complexes with the BRI1-like receptors (The Plant Cell, 2004, 16, 3216-3229; Cell, 2002, no 213-222; Cell, 2002, 110, 203-212). They are also involved in binding extracellular peptide ligands, represented by candidate peptide ligands like the 14 *Arabidopsis* GASA (Gibberelic Acid Stimulated *Arabidopsis*; Plant Mol Biol., 1995, 27, 743-752) gene products that have been postulated to bind directly to the 14 *Arabidopsis* RKS gene products (WO 04/007712). GASA proteins contain a pocket in their structure that is postulated to be involved in binding brassinosteroids with high affinity. CASA peptide ligands would thereby act as an intermediate between the RKS/BRI-dimers and the brassinosteroid molecule. The dimerisation complex between RKS and other receptors like BRI1 is a dynamic plasma membrane complex, in which different family-members are able to participate as dimerisation partners (see FIG. 1).

Modulation of activity of these classes of receptor kinases is regulated by both peptide ligands and steroid hormones. Plant brassinosteroids are available in different forms (described in J. Exp. Botany, 1999, 50, 275-282; The Plant Cell, 2002, S97-S110; Plant Physiol., 2003, 131, 287-297). Apart from these, a number of synthetic agonists or antagonists (Trends in Plant Science, 1999, 4, 348-353) can be used to regulate these receptor activities.

In the protein receptor complex described above the ELS proteins (WO 04/007712) are also involved in perception of brassinosteroids and transmission of the signal and thus in mediating the resistance responses throughout the plant. LRP, the tomato homolog of the *Arabidopsis* ELS gene products, is specifically induced and surprisingly also proteolytically processed during pathogenesis (Mol. Gen. Genet., 1994, 243, 47-53; Plant J., 1996, 10, 315-330). ELS protein products are therefore clearly involved in the resistance responses, and might play a role in the modulation of brassinosteroid regulation of resistance.

Jasmonate signalling, mediated by jasmonic acid (JA) and a number of derivative molecules, is also known to play an important role in plant resistance as well as in developmental processes like fruit ripening, senescence, and embryo- and pollen development (The Plant Cell, 2002, 14, S153-S164). JA is involved in mediating ubiquination pathways, through the action of F-Box proteins like COI1. Perception of JA might be mediated by gene products like those encoded by the JAI-1 locus (PNAS, 2002, 99, 6416-6422) or by receptors yet to be identified.

Plants have developed sophisticated processes of activating a systemic immunity mechanism throughout the whole plant. In many aspects this secondary defence barrier is comparable to a vaccination response in humans, and overlapping elements depend on similar gene products and signalling pathways that remained conserved during evolution between plants and animals (EMBO reports, 2005, 6, 504-507). The systemic resistance response in plants can be broadly divided into systemic acquired resistance (SAR) and induced systemic resistance (ISR) (Curr Opin Plant Biol., 2004, 7, 456-464). Although these different modes of resistance are each effective against a broad range of pathogens, their responses are at this stage more or less specific for different classes of pathogens (Mol Plant Microbe Interact., 2002, 15, 27-34). A broad-spectrum resistance response aimed against bacteria or viruses is not necessarily resulting in an induced level of resistance against e.g. nematodes or aphids. Besides each signalling cascade is induced and transmitted by combinations of different signalling molecules (Trends in Genetics, 2000, 16, 449-455).

Normally, the systemic transport of these plant-produced signals results in systemic induction of long-term broad resistance. However, the specific combinations of plant signals together dictate the specific nature of the resulting long-lasting systemic response. Some responses are triggered already by the presence of one signalling chemical; others have overlapping requirements for different chemicals altogether. Examples of the signal compounds are salicylic acid, jasmonic acid, ethylene, (Nature Biotechn., 2000, 18, 779-783), and brassinosteroids (WO 04/007712). Peptide factors such as systemin and GASA are known to interfere with brassinosteroid signal perception, as discussed above. Artificial application from outside the plants by e.g. spraying these specific signalling molecules is able to activate the desired induced resistance responses within the plant. Modulation of the concentration and the composition of the various systemic plant signals in the spraying solutions allows for the modulation of acquisition of systemic resistance.

These systemic signals are perceived by the cells and organs in the parts of the plants, which are not directly involved in the infection process. This perception is accomplished by specific receptors for each of these systemic signal molecules.

Controlling the level of disease resistance in (mono)cultures of crop plants under field conditions is a constant struggle between the producing farmer on one side and the various natural pathogens on the other side. The plant itself often consists of a clonal variety bred for high yield levels, and its genomic make-up is generally not optimized for optimal disease resistance. The major tool available for protection of the growing plants or the subsequent protection of the harvested crop consists of the application of biocides, such as fungicides, bactericides and insecticides. The current understanding of environmental problems associated with these chemicals has resulted in prohibiting many of the available chemicals, leaving farmers without available alternatives for the control of diseases. Many of the currently ongoing classical breeding strategies aimed at disease resistance will take many years to come to produce new valuable hybrids and cultivars for commercial application. However, in the last decades numerous attempts have been made to increase the resistance by genetic engineering, e.g. by transforming the plant with components of the hypersensitive response and intermediates of the signal molecules (Transgenic Res., 2002, 11, 599-613). Most of these transgenic alternatives have, as for yet, not reached the market.

One method in which the farmer takes advantage of the plant's natural defence mechanism is by priming the defence response by administration of signalling compounds such as salicylic acid. These signalling compounds can be applied within the environment (soil additive, spraying, dusting, etc.). The disadvantage of this approach, however, is that the signalling compounds, while they need to be administered in high doses to compensate for losses of spraying and losses during uptake by the plant, at least in the concentration in which they have to be used to induce ISR, are partly toxic and/or environmentally unfriendly. Using the plant's own machinery offers an alternative through an increased endogenous production of the signalling compounds by the plant itself. Hereby the genes regulating the levels of active signalling compounds (like SA, brassinosteroids, etc.) are expressed within the transgenic plant itself under the control of an inducible/tissue specific or stage specific promoter. Modulation of the steady state level of these gene products in turn regulates the level of active signalling compounds. Examples of such gene products are the proteases involved in cleaving the pro-systemin peptide, or the DWARF4 gene product (Plant Journal 26 2001 573-582). A specific disadvantage of this latter approach is that the whole plant is induced, which often is not necessary and reduces the overall fitness (and yield) of the plant. Thus, there is still the need for alternative strategies for enhancing disease resistance in plants that would as little as possible interfere with the fitness and yield characteristics of the plant.

SUMMARY OF THE INVENTION

The invention now provides a method for enhancing pathogen resistance in plants by providing these plants with a gene construct comprising a DNA sequence coding for a receptor for a systemic signal compound, wherein such a systemic signal compound is one or more of the group consisting of salicylic acid, jasmonic acid, and brassinosteroids. More specifically the receptor is chosen among the jasmonic acid receptor, the salicylic acid receptors, and the RKS receptors.

The enhancement of the sensitivity of plants for induced resistance is achieved by increasing the number of receptor molecules, corresponding to one or more of the above-mentioned receptors, per cell/organ.

Increase in perception can be performed by increasing the amount of warning signal receptors but also by increasing the (local) concentration of these warning signals themselves This can be performed by administration or by (local) endogenous production of these signals like SA or brassinosteroids.

A specific embodiment is formed by a method wherein the DNA sequence coding for the receptor is under control of a tissue specific promoter (like promoters specifically expressed in fruits, seeds, or flowers) or an inducible promoter, like pathogen inducible promoters, detergent inducible promoters (TWEEN20; Hunzicker, G. M., et al. (2004) Proceedings for the 4th International Crop Science Congress, Brisbane, Australia, 26 Sep.-1 Oct. 2004), heat shock inducible promoters (Biochem Biophys Res Commun., 200, 321, 364-369), steroid inducible promoters (either animal steroids (e.g. Plant J., 2005, 41, 899-918) or plant steroids (e.g. promoter of At2g14560), tetracyclin-repressor-based promoter systems (Plant J., 2000, 21, 579-588) etc.

A further specific embodiment is formed by a method wherein the DNA sequence coding for the receptor is chimaeric, wherein chimaeric means that the ligand recognising part of the above mentioned receptors has been replaced by a ligand recognising part of another receptor, such as a different signal compound recognising receptor from the selection mentioned above, a steroid receptor, receptor for PAMPs, sterols, peptides, or a receptor for other diffusible molecules involved in mediating a systemic resistance response.

Also part of the invention are plants which are produced by a method according to the invention. A specific embodiment of such a plant is a plant in which two or more receptors, which may or may not be chimaeric, have been introduced. Further part of the invention is an inbred plant variety produced from the offspring of said plant wherein said variety still contains the increased sensitivity for induced resistance. Similar results can be obtained by combining different overexpressing constructs involved in the same pathway, like a construct coding for a receptor in combination with a construct coding for a downstream target molecule like a transcription factor.

Another embodiment of the invention is a method to induce resistance in a plant or a variety according to the invention, comprising applying a ligand molecule to said plant or variety, which is able to bind to and stimulate the heterologous or chimaeric receptor with which the plant or variety is provided. Said application preferably comprises spraying of the molecule.

Proteins interacting with RKS receptors are shown in dark grey. BRL stands for BRI1-like and other RLKs (receptor lika kinases) that may heterodimerise with RKS; NHL (NDR1/HIN1-like) and SPL (Squamosa-binding Protein-Like) correspond to the members of these two families that interact with RKS. Upstream and downstream components are indicated in light grey.

Figure 2:
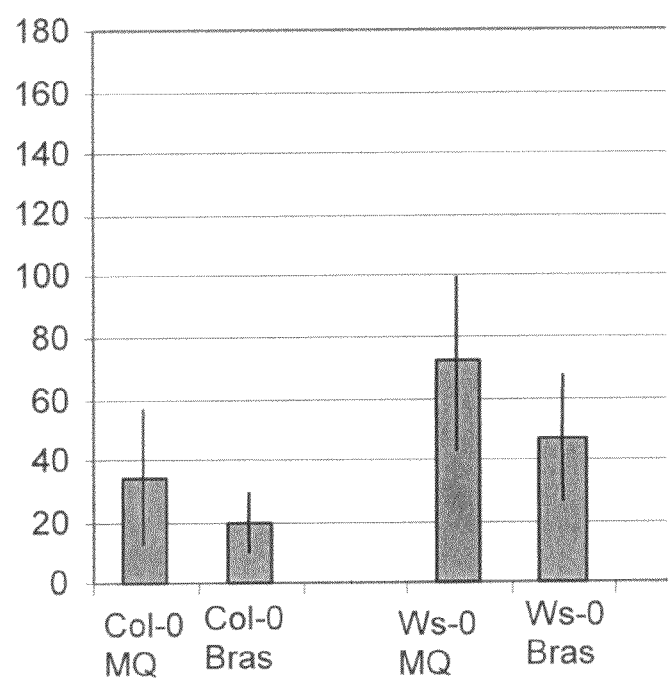
Figure 3A:
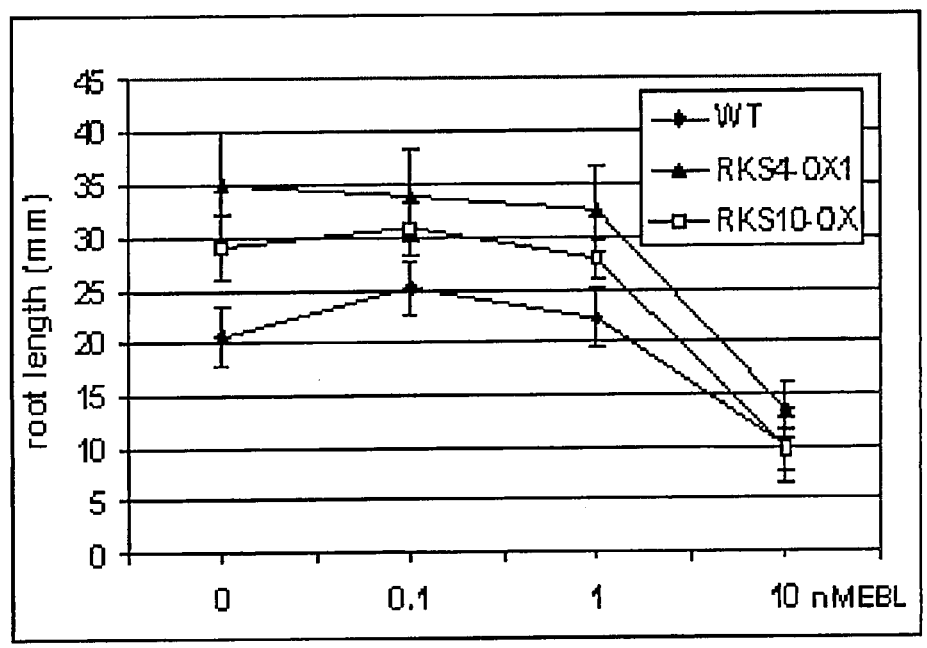
Figure 3C:
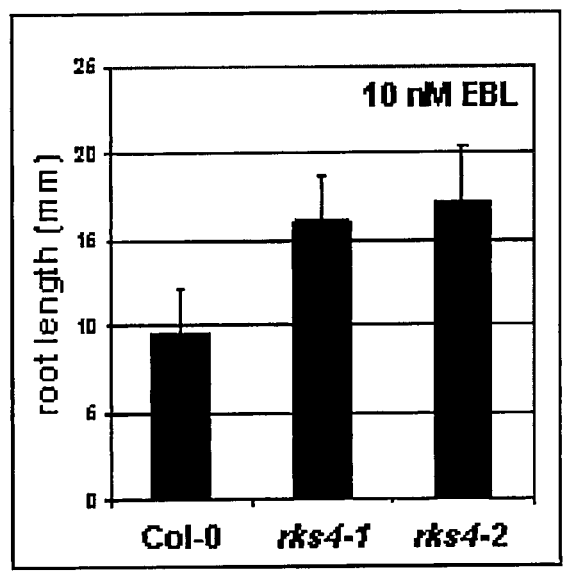
Figure 3B:
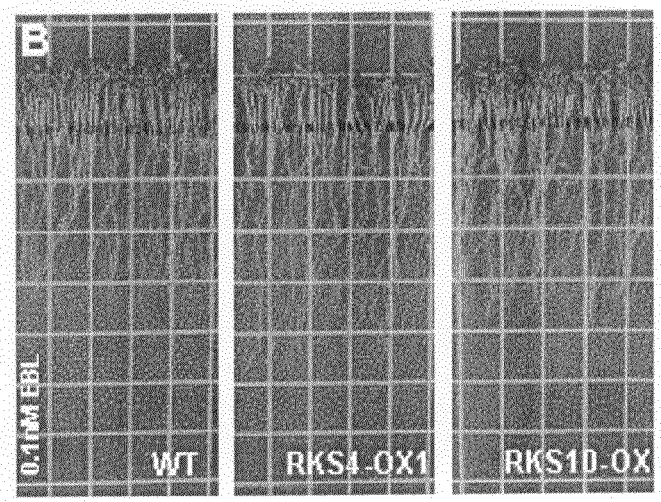
Figure 3D:
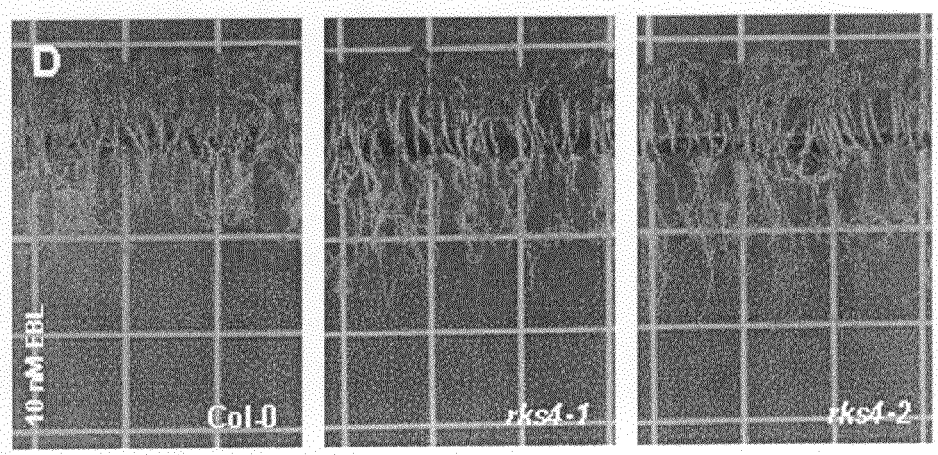

FIG. 2 Brassinosteroids increase resistance to *Peronospora parasitica*.

Nine-day old *Arabidopsis* seedlings, ecotype Columbia (Col-0) or Wassilewskija (WS-0), were sprayed with mock-Silwet L-77 (0.01%) (MQ=water+Silwet) or 0.05 mM brassinosteroids (+0.01% Silwet L-77=Bras). After drying, the plants were incubated in the long day growth chamber (MPMI 2005, 18, 583-592). After two days half of the plants were sprayed on their leaves with Waco9 (50 spores/A; European journal of Plant Pathology, 2001, 107, 63-68). Plants (40 seedlings per line) were scored for sporulation, 7 days post inoculation. The mock was used as a control. Experimental infections and analyses were performed as previously described (MPMI 2005, 18, 583-592). This showed that, two days after spraying the mock and, Brassinosteroid mix, the plants sprayed with brassinosteroids were elongated but after six days they looked almost the same as the mock, only treated with 0.01% Silwett-L77 in water (just slightly more elongated. Also some of the cotyledons had turned upside-down. Col-0 and Ws-0 plants sprayed with brassinosteroids showed less sporulation of Waco9 compared to the mock control.

FIG. 3 The RKS4 receptor is involved in brassinosteroid perception.

A. Effect of 24-epibrassinolide (EBL) concentration on root growth as measured on Ws-0 (WT), RKS4-OX1 and RKS10 (BAK1, Cell, 2002, no, 213-222) overexpression (RKS10-OX) seedlings after 9 days on vertical plates. B. Root length on 0.1 nM EBL. Each square is 1 cm2. C. Effect of high EBL concentration on root growth of RKS4 KO (knock-out) lines (see FIG. 4A for details). D. Root length on 10 nM EBL. Each square is 1 cm2.

Figure 4:
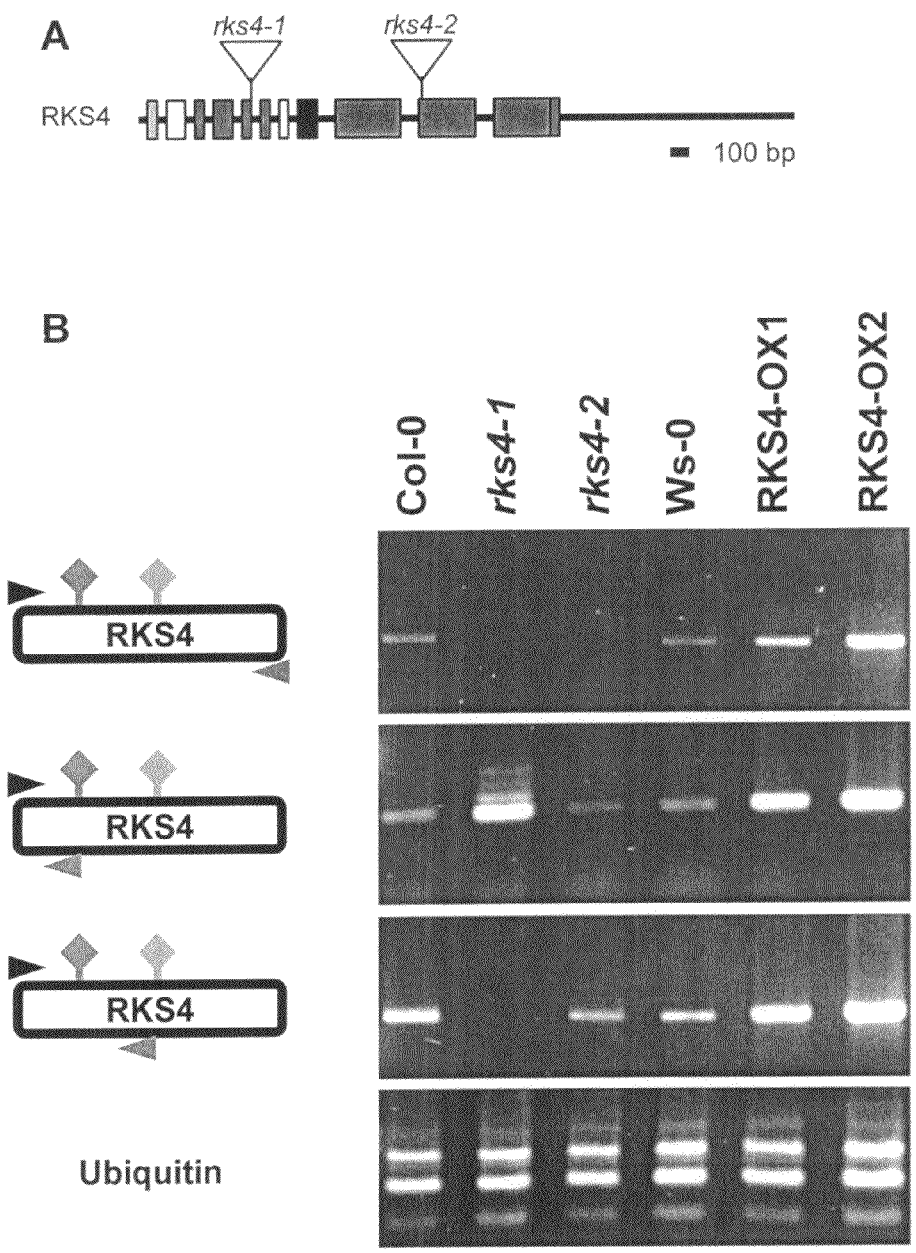

FIG. 4 RKS4 mRNA levels in knock-out and overexpression seedlings.

A. T-DNA insertion sites on the RKS4 gene. B. RT-PCR analysis of the RKS4 full-length messenger in 10 day-old seedlings from wild-type (Ws-0 and Col-0), an overexpression line (RKS4-OX) and two T-DNA insertion lines (rks4-1 and rks4-2). A no template control was included and equal amounts of cDNA template were assessed on the constitutive ubiquitin gene (Ubi). The position of the different oligonucleotides used within the RT-PCR reaction is indicated with respect to the different T-DNA integration sites.

Figure 5A:
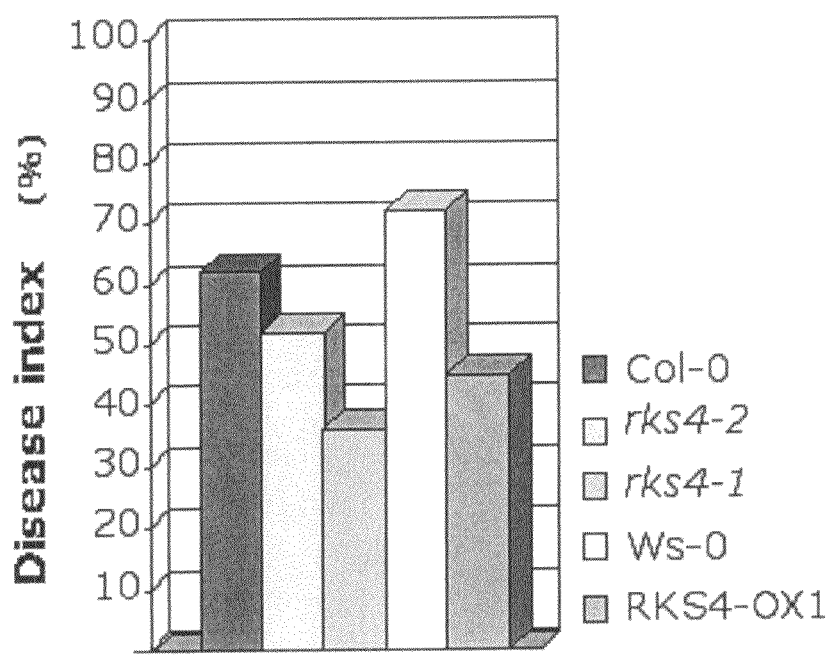
Figure 5B:
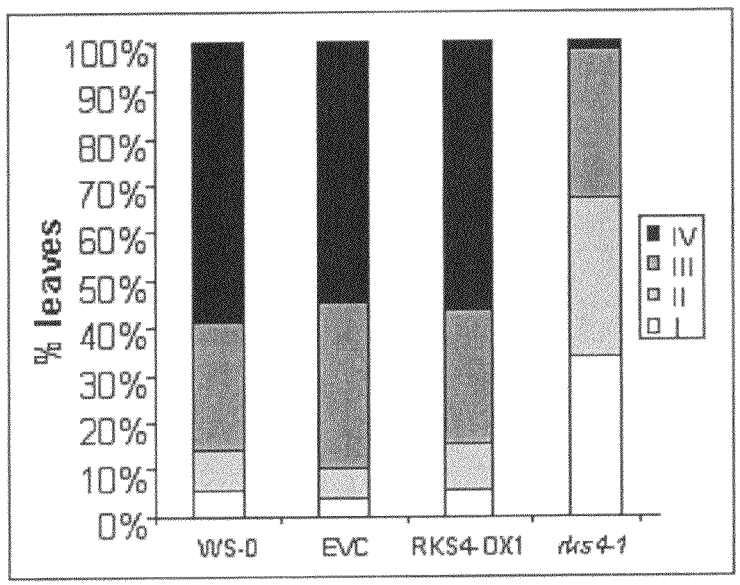
Figure 5C:
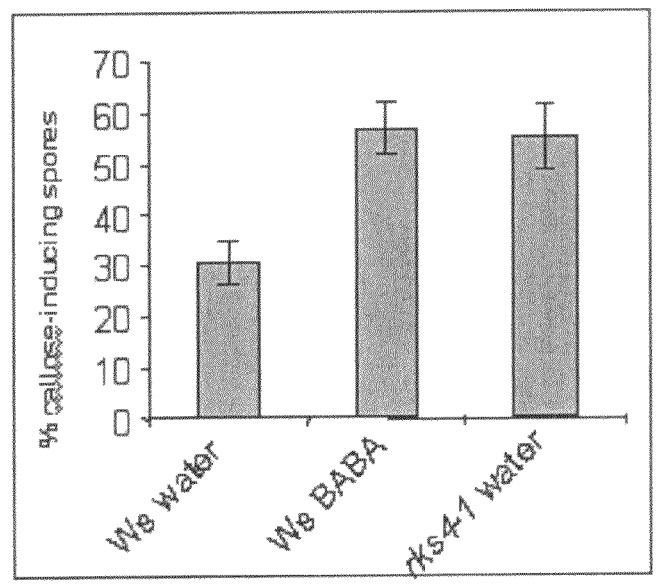

FIG. 5 RKS4 modulates resistance against *Pseudomonas syringae* pv. tomato DC3000 and *Peronospora parasitica*.

A. Overexpression of RKS4 (RKS4-OX1) shows induced levels of resistance against the pathogen *Pseudomonas syringae*. This is represented by the disease index on the Y axis. Extrapolation of available data suggests that knock out lines of RKS4 are also involved in mediating resistance responses. Resistance assays were performed as described previously (Plant Cell 1996, 8, 1225-1237; Plant cell 1998, 10, 1571-1580). B. KO of RKS4 (rks4-1; increased expression of N-terminus, see FIG. 4) also increases resistance to *Peronospora parasitica*, although less than the positive control induced with β-aminobutyric acid (BABA). Plants were scored using an arbitrary scale I-IV, in which I means normal to very slight symptoms and IV means severe symptoms to death. C. Callose deposition was verified in the same plants, which revealed that, as upon treatment with BABA, callose deposition is increased in rks4-1 plants, suggesting that increased resistance mediated by altered levels of RKS4 includes enhanced callose deposition. Both tests were performed as described in (Plant Cell., 2005, 17, 987-999).

Figure 6A:
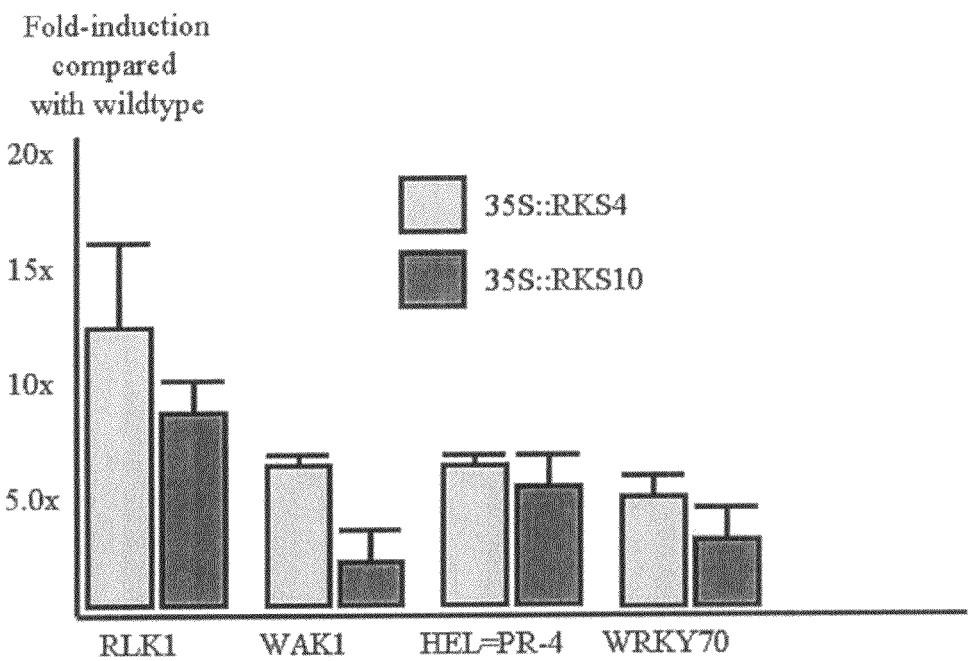
Figure 6B:
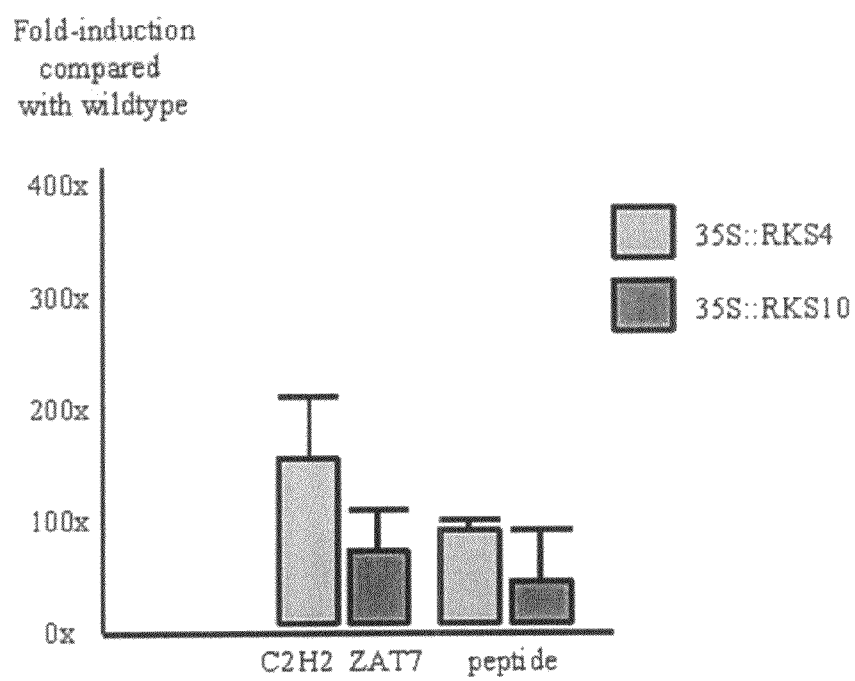

FIG. 6 Expression analysis of disease resistance marker genes in RKS4 overexpression background.

This was performed by quantitative RT-PCR (qRT-PCR) using the Primer Library for *Arabidopsis* Pathogen-inducible genes (SIGMA) on RNA isolated from 10 d-old seedlings from Ws-0, 35S::RKS4 and 35S::RKS10. Fold induction corresponds to the average of three replicates in expression changes ($2^{\Delta\Delta Ct}$ values) after normalisation with Actin (control primers of the library) and using the wild-type as a reference. The error bars correspond to the standard deviation between replicates. A. RLK1=At5g60900, WAK1=At1g21250, HEL (hevein-like protein)= PR4=At3g04720 and WRKY70=At3g56400. B. ZAT7 ($C_2H_2$ zing finger protein)=At3g46090 and the peptide is encoded by At2g32200. Shows that RKS4 overexpression induces the expression of specific defence-related genes, confirming its involvement in disease resistance.

FIG. 7 Morphological phenotypes induced by altered expression of RKS4.

Histograms shown in panels (b), (e), (0 and (g) are based on measurements performed on plants with RKS4 altered expression and depict changes in percentages related to the corresponding wild-type (Col-0 for rks4-1 and -2; Ws-0 for RKS4-OX1 and 2). Statistical significance of the observed differences was analyzed by t-test and the * indicates that the measured differences are not statistically significant (i.e. p-value>0.05).

(a) Increased flower size due to RKS4 overexpression (RKS4-OX1) versus wild-type Ws-0 (WT) (scale bar=1 mm).

(b) Influence of RKS4 overexpression on petal and petal epidermis cell size. The number of cells/petal was obtained by dividing the mean of the petal surface area by the mean of the cell surface area.

(c) Altered leaf shape in rosettes of RKS4-OX1 plants (scale bar in cm).

(d) Overview of rosette shape and size in RKS4-OX1 and WT plants (scale bar in cm).

(e) Influence of RKS4 altered expression on cotyledon size based on measurements of the surface area of cotyledons and of their palisade mesophyll cells. The number of cells per cotyledon was obtained by dividing the mean surface area of the cotyledons by the one of the mesophyll cells.

(f) Influence of RKS4 altered expression on seed yield determined by seed length and weight measurement.

(g) influence of RKS4 altered expression on root length as measured on 9 day-old seedlings grown on vertical plates.

(h-i) Changes in root tip mitotic activity caused by overexpression of RKS4. (h) From left to right: GUS positive/dividing cells in the root tip of a 7-d old seedling containing the pCDG construct (Colón-Carmona, A., You, R., Haimovitch-Gal, T. and Peter Doerner, O. (1999) Spatio-temporal analysis of mitotic activity with a labile cyclin-GUS fusion protein. Plant J. 20, 503-508) alone; reduced number of dividing cells in the root tip of a 7-d old F1 seedling from a cross between RKS4-OX1 and pCDG; root tip of a 7-d old F1 seedling from a cross between RKS4-OX2 and pCDG (scale bar=50 um). (i) Histogram of the average number of GUS positive cells per root tip in the main root (standard deviation indicated by the error bars).

Figure 8:
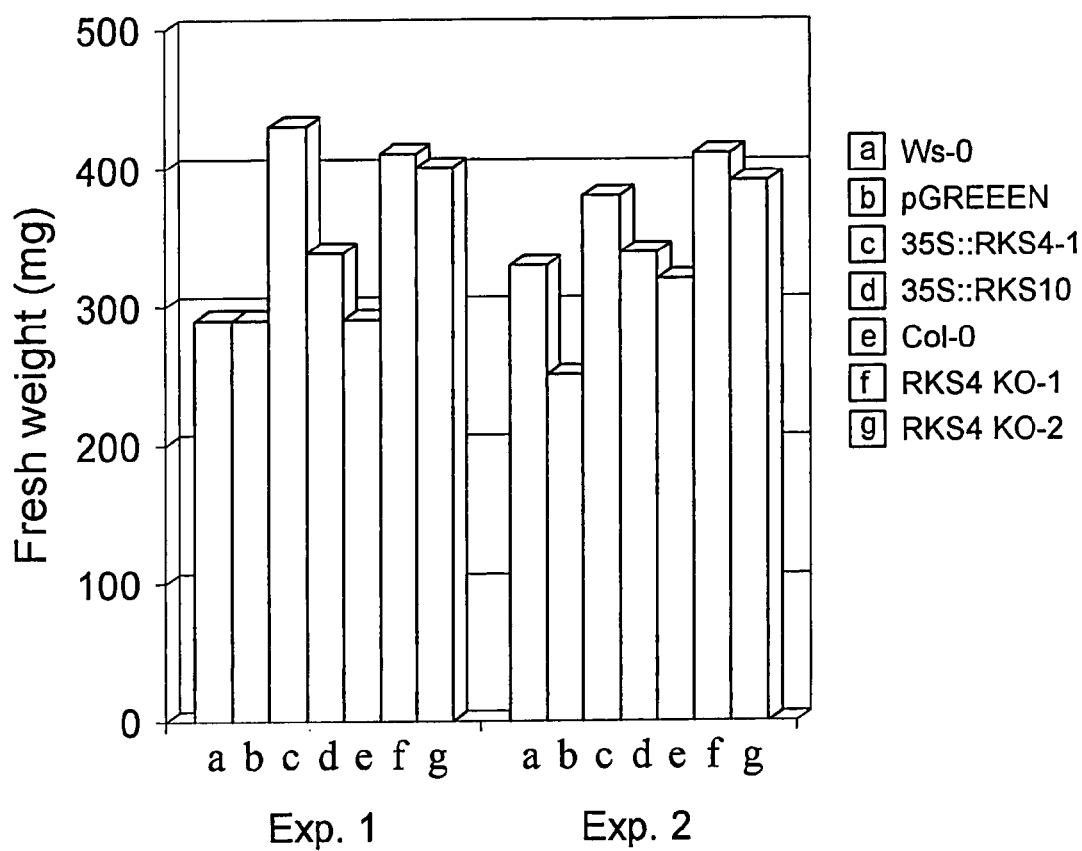

FIG. 8 Altered expression of RKS4 increases fresh weight.

Ws-0, Col-0, pGREEN 4K (empty vector control) and 35S::RKS10 were used as controls. The graph shows that fresh weight is increased, again in the overexpression and in the KO lines, which is in agreement with the data in FIG. 7. Thus, modulation of RKS4 levels enhances, next to disease resistance also plant fitness (growth) characteristics.

Figure 9A:
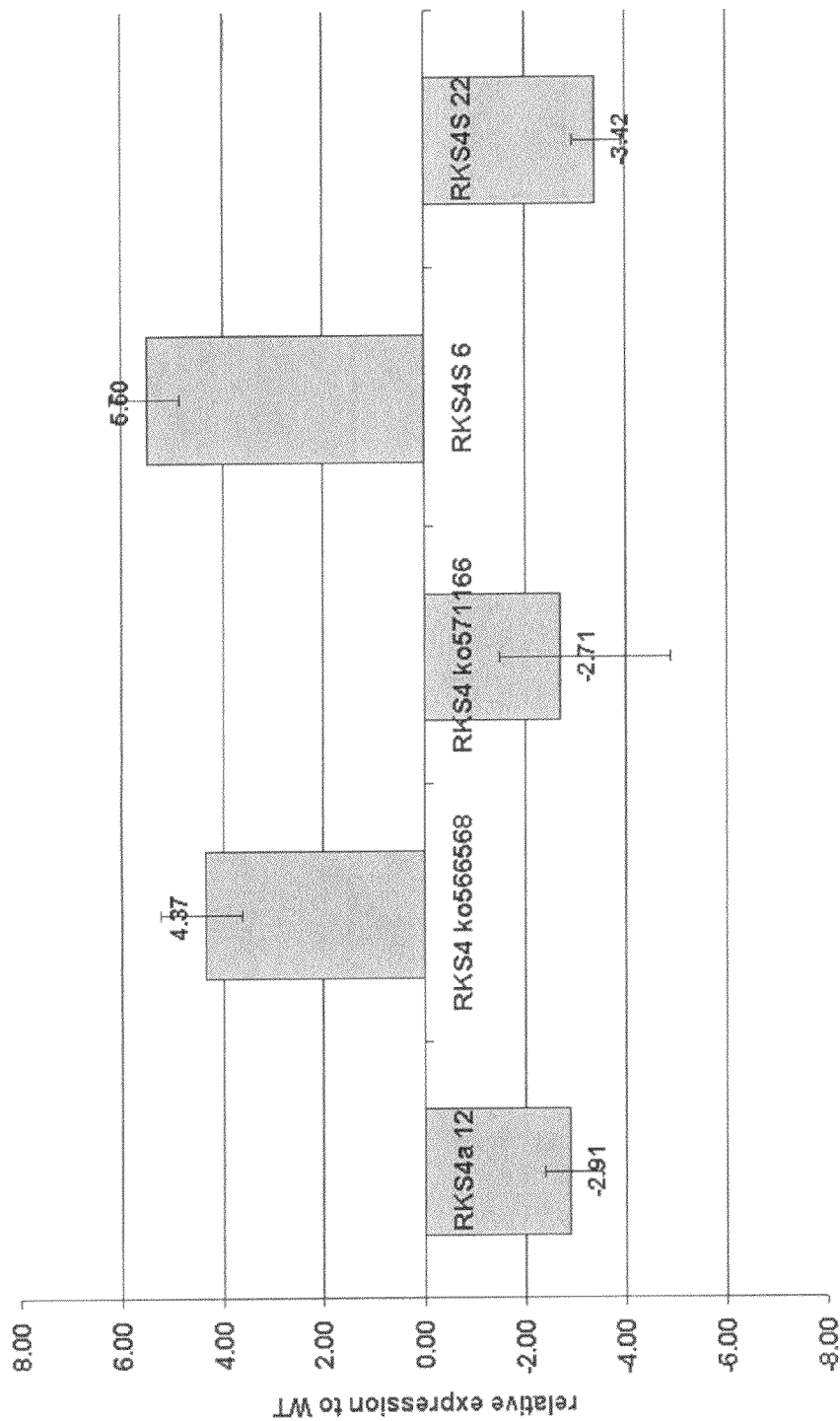
Figure 9B:
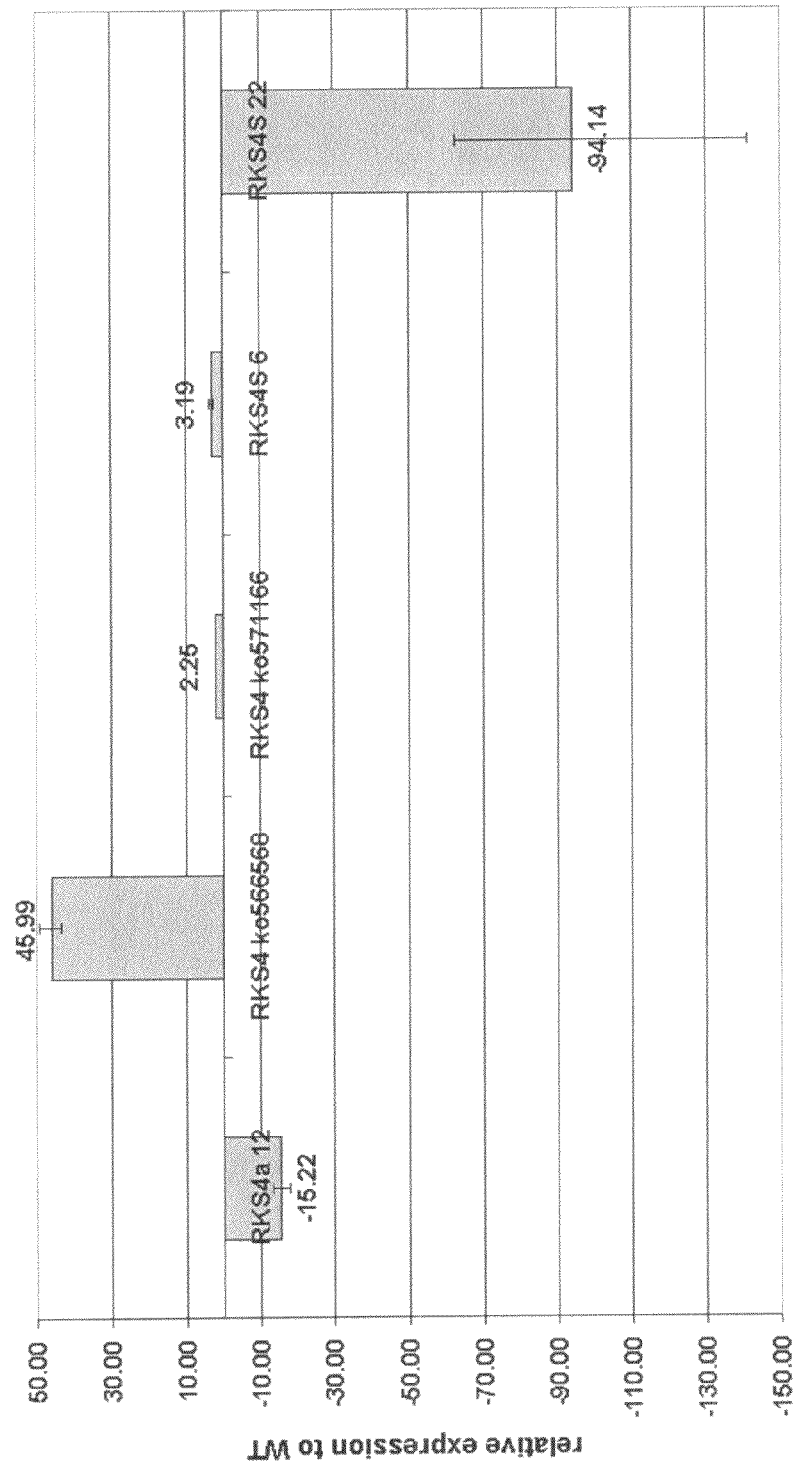

FIG. 9 Influence of altered RKS4 expression levels on the expression of the At2g14560 and PR1 marker genes.

A. qRT-PCR analysis of the reporter gene At2g14560 (a marker for both brassinosteroid induction and for NPR-1 mediated resistance activation). RKS4-OX1 (RKS4S 6) and rks4-1 (ko566568) both show an increase of mRNA levels of this reporter, indicating a function of the N-terminal fragments of RKS4 (as visualised in FIG. 4) in regulating RKS4 signalling-mediated gene expression. RKS4-OX2 (RKS4S 22), knock down of RKS4 (RKS4a 12) and knock out of RKS4 (rks4-2=ko571166) all result in decreased levels of this marker gene. B. qRT-PCR analysis of the reporter gene PR-1=At2g14610 (a marker for SAR induction and NPR-1 mediated resistance activation). At2g 14560 and PR-1 are positioned close to each other on the *Arabidopsis* genome and these and the other genes within this locus, like At2g14620, a xyloglucan:xyloglucosyl transferase, are under direct control of resistance-modulated transcriptional activation. rks4-1 (ko566568) shows a strong increase in mRNA levels of the PR-1 reporter, indicating a function of the N-terminal fragments of RKS4, as visualized in FIG. 4, in regulating RKS4 signalling-mediated gene expression. RKS4-OX2 (RKS4S 22) and knock down of RKS4 (RKS4a 12) result in decreased levels of this reporter marker gene product. These data show that the levels of receptor mRNA determines the responses of downstream target gene products.

Figure 10:
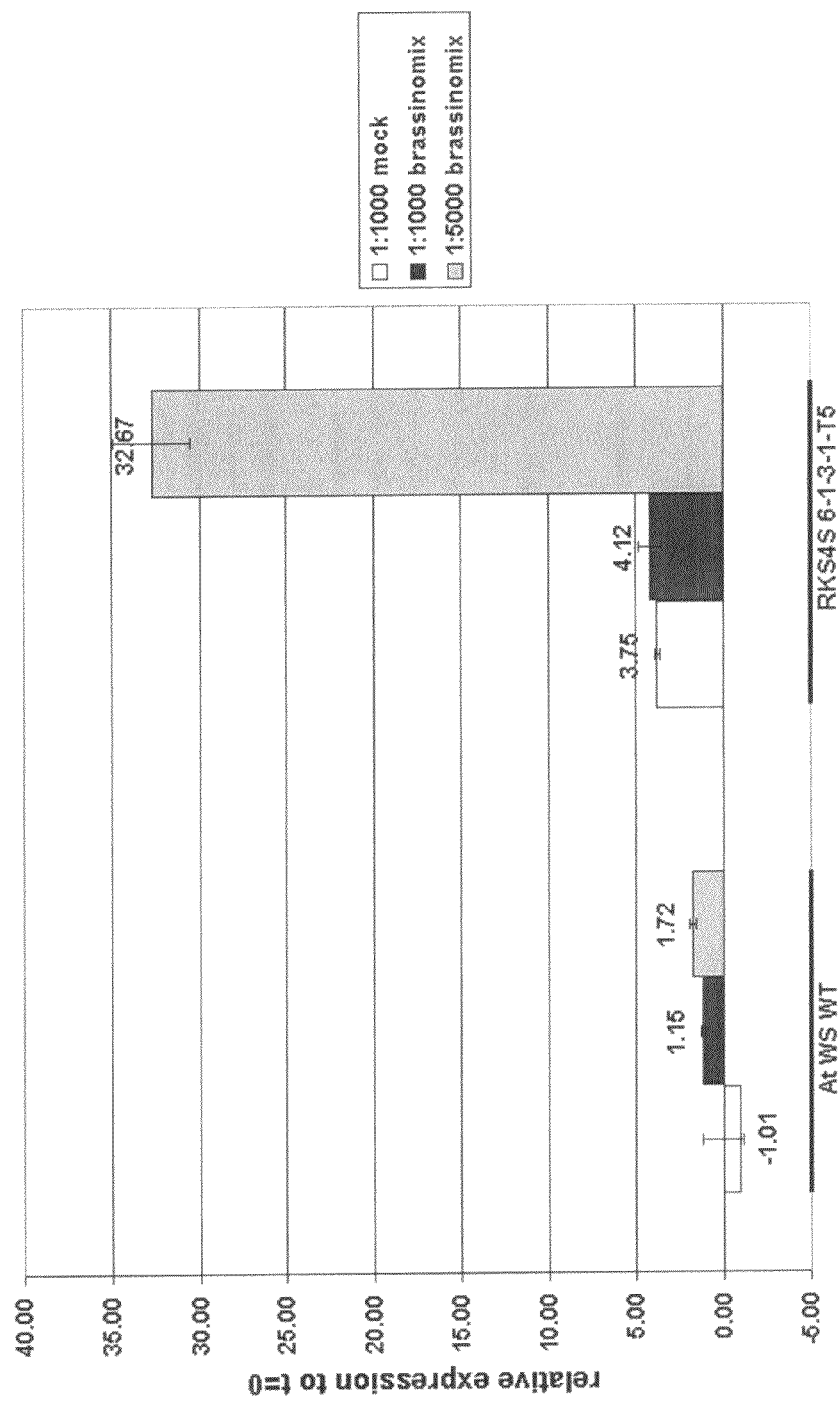

FIG. 10 Influence of Brassinosteroid treatment in combination with RKS4 overexpression on the expression of the At2g14560 marker gene.

At2g14560 mRNA levels were detected by qRT-PCR after spraying of Brassinomix (diluted stock of brassinosteroids, 0.05 or 0.01 mM (resp. 1:1000 or 1:5000 diluted), mixed with Silwett L-77 (final concentration 0.01%)) or a mock solution of 0.01% Silwett L-77. This shows a very strong increase in the amplitude of brassinosteroid responses in the RKS4-OX1 line (RKS4S 6) compared to the wild-type WS control. This increase is already detected at 3 hours after spraying the brassinosteroids. This time is too short for indirect activation responses. The RKS-mediated signalling therefore has a direct effect on transcriptional activation by this brassinosteroid and NPR-1 activated reporter genes. The mRNA levels of At2g14560 within the wild-type and transformed plants at time point t=0, just prior to spraying are used as the baseline in this figure. For each experiment 3 plants were treated and harvested. Material was mixed for mRNA isolation. Q-PCR experiments were performed in triplo, standard errors are indicated.

Interestingly, the optimal brassinosteroid concentration in the RKS4-OX1 plants was the most diluted one (0.01 mM), confirming that too much brassinosteroids does not have stimulating effects any more. Therefore both receptor levels and brassinosteroid levels together determine the final responses of the plant.

Figure 11:
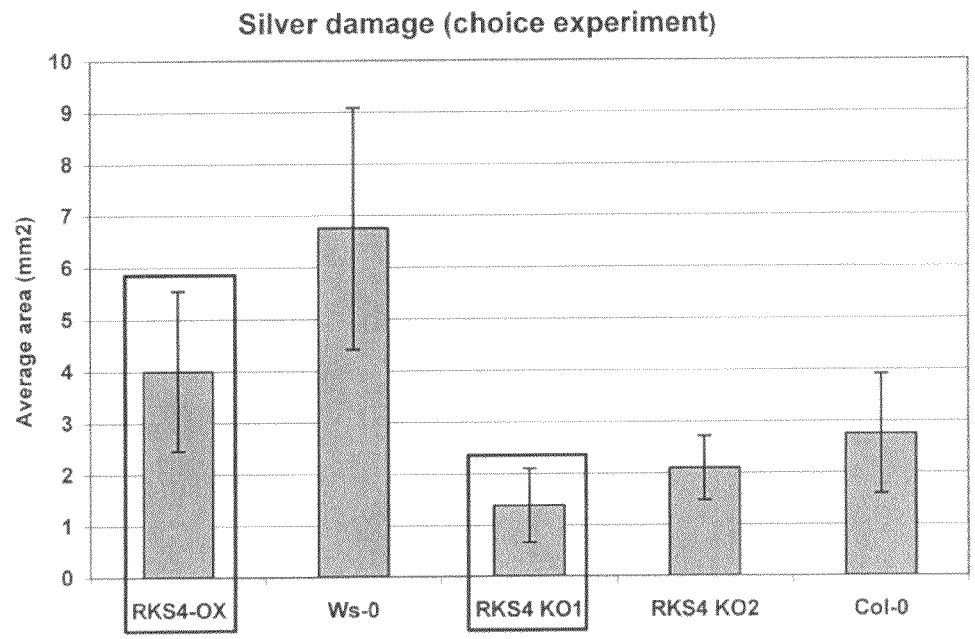

FIG. 11. Distribution of silver damage per genotype per leaf.

Data represent the average of 2-5 replicates. Error bars represent the standard deviation. Boxed genotypes show significantly less damage than the corresponding wild-type (Ws-0 for the overexpression line and Col-0 for the KO lines).

Figure 12:
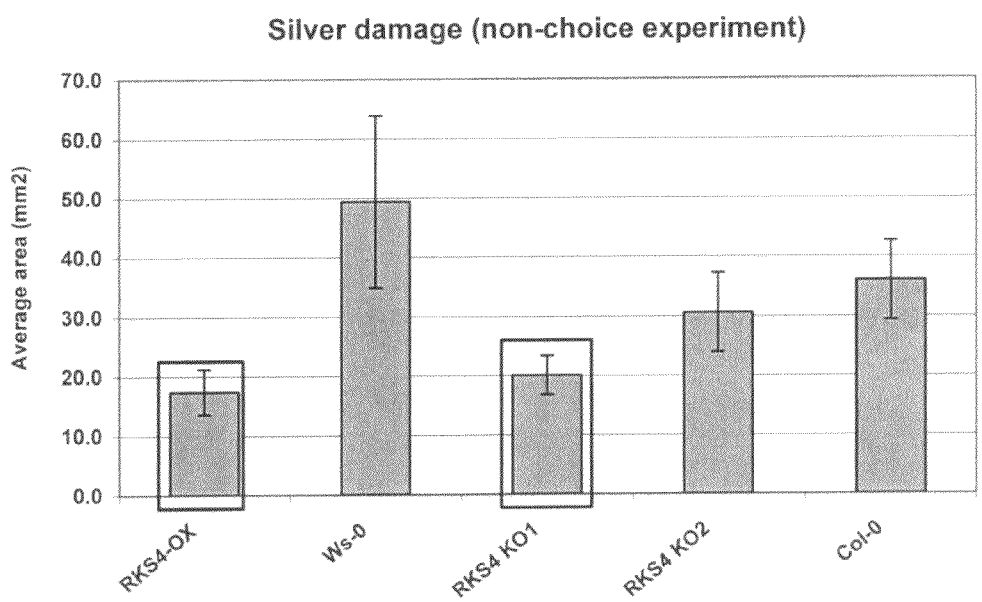

FIG. 12. Distribution of silver damage per genotype per leaf.

Data represent the average of 10 replicates. Error bars represent the standard deviation. Boxed genotypes show significantly less damage than the corresponding wild-type (Ws-0 for the overexpression lines and Col-0 for the KO lines).

DETAILED EMBODIMENT OF THE INVENTION

The basis of the invention is to increase the sensitivity of a plant for induced resistance. As has been discussed in the introduction the induced resistance is caused by an initial reaction of a plant to an attack by a pathogen, which attack subsequently results in the dispersal of systemic signalling compounds such as salicylic acid, jasmonic acid and brassinosteroids. These compounds are perceived by specific receptors in the plant cell. It has now been found by the present inventors that the amount of receptors for these signalling compounds is a limiting factor in the resistance pathways. Thus, increasing the number of receptors per cell or tissue will enable a stronger response to circulating systemic and/or externally applied signalling compounds. This increase will preferably be performed by transformation of the plant cell with a nucleotide construct, which comprises the coding sequence for such a receptor molecule.

Figure 1:
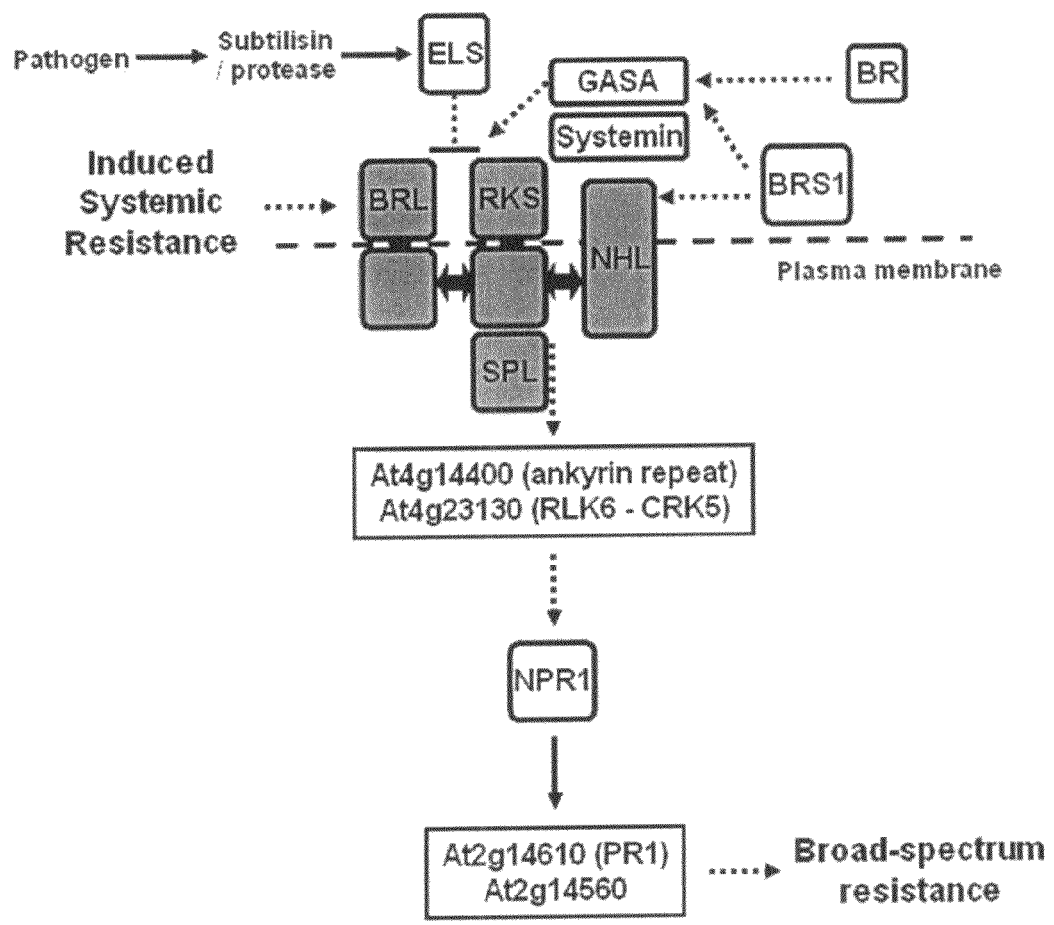
FIG. 1 Proposed model of BRI/RKS mediated signalling with respect to disease resistance.

The BRI/RKS dimerising transmembrane protein complex (see FIG. 1) is involved in developmental processes (The Plant Cell, 2004, 16, 3216-3229; Cell, 2002, 110, 213-222; Cell, 2002, 110, 203-212), as well as in the regulation of resistance through the perception of brassinosteroids (Plant Journal, 2003, 33, 887-898; and data obtained by the present inventors, e.g. FIG. 2 and FIG. 5). The perception of the diffusing systemin peptide and possibly the GASA ligands are also involved in mediating the resistance response through this membrane associated protein complex. The heterodimerising protein partners in this complex (FIG. 1) therefore mediate a diverse set of processes like resistance, growth and flower organ development.

Surprisingly, it has been established by the present inventors that overexpression of the BRI1-receptor does not enhance the pathogen resistance of a plant, whereas overexpression of an RKS-receptor has a marked effect (see Experimental Section). This suggests, that, as far as involvement in the pathogen resistance pathway is concerned, the RKS receptors seem to be a limiting factor.

This makes it an important group of receptors, which are very suitable for use in the present invention. The perception mechanism of these receptors resembles that of the inflammation responses in animal systems, which are controlled by steroids. There, glucocorticoid application reduces the primary responses towards pathogen invasion. This process is modulated by a reduction of mRNA stability of several key regulators of the inflammatory response, e.g. COX2. Furthermore these steroids regulate the activity of several transmembrane TOLL-like receptor complexes such as IL-1 (J. Endocrinology, 2003, 178, 1-4). Homologues of the TOLL-like receptors in plants are represented by a subgroup of LRR receptor kinases, containing among others the BRI1 and RKS homologues together involved in plant steroid signal transduction. One of the pathways modulated by plant steroid signalling is the intracellular MAP kinases pathway (FEBS Lett., 2001, 2, 346-50), which is in animal systems a target for inhibition by glucocorticoids (Curr Opin Pharmacol., 2003, 3, 404-11). These data led to the hypothesis that plant steroid signalling and SA signalling show extensive cross-talk with each other, and that they mediate this interaction by using similar pathways and gene products as in animal systems. Each of these signalling compounds by itself is able to regulate resistance responses, for which they use partially overlapping intracellular processes.

It has now been established that overexpression of such a receptor induces a higher level of pathogen resistance in a plant. A higher level, indeed, because it appears that there already is an endogenous (low) level of signalling compound, which is able to stimulate the receptor, which sets the cascade, discussed above, running and which then leads to a (low) level of induced resistance. This is in particular advantageous since this already provides a level of resistance without the need for additionally applying the signalling compound. Further, this also brings along an increased sensitivity of the downstream cascade, which makes it possible to use ligands, which can stimulate compounds of the downstream cascade for increasing the level of resistance. These ligands can, inter alia, be chosen from the group consisting of SPL, At4g14400, At4g23130, NPR1, At2914610, At2g14560 and other proteins that are part of the downstream cascae. Since it has appeared that there is crosstalk between the brassinosteroid anti-pathogenic cascade and e.g. the SA pathogen resistance cascade, it is possible that application of other factors, such as plant steroids, elicitors from pathogens or fragments thereof, SA, JA and extracellular peptides with a signalling function like GASH or systemin or fragments of these peptides, can also be used to boost the activated cascade. Accordingly, it is possible to replace a signal molecule, which may be undesirable to use under certain conditions (e.g. because of toxicity, environmental issues, etc.) by a ligand acting on the downstream cascade.

It has further been found that overexpression of the receptor for enhancing resistance is bound to an optimum. Apparently, too much receptor can give overstimulation of the downstream cascade, which suggests that it is auto-regulated by inhibition mechanisms (see FIGS. 4 and 7). Hence, when plants are provided with a genetic construct coding for a receptor for a signalling compound, care should be taken to not choose the highest expressors, but rather to test for optimal resistance parameters. Such tests, which are easily performable for a person skilled in the art, are described herein below. Basically, there are several methods to determine optimum resistance, such as: 1) performing resistance assays, such as the ATTA assay (Cell, 1996, 87, 1307-1316); and 2) determining the amount of marker genes, like PR-1 or At2g14560 (a gene under direct transcriptional control of NPR1, strongly induced by SA and brassinosteroid application (Plant Physiology 2005, 137, 1147-1159; Science 2005, 308, 1036-1040)) or At3946090 (ZAT7) or At2932200 (see also FIGS. 9 and 10).

The possibility to use genes, with modified expression after over-expression in plants of RKS4 or other RKS receptor, as markers (as indicated under method 2) above) offers the possibility to engineer assays for optimising priming of transgenic or non-transgenic plants through spraying.

The RKS receptors, of which RKS1, RKS4, RKS7, RKS11 and RKS14 are the most preferred receptors (see e.g. WO 04/007712, pages 45 and 52-93 (which corresponds to Table 2 on page 20, and paragraphs to [0140], respectively, of US patent publication 20060265783), which are herein incorporated by reference). See below.

TABLE overview of accessions numbers of RKS signal complex genes in *arabidopsis* and in rice:

| Gene | code | contig | gene prediction in At database | *Oryza sativa japonica* contig | approximate position in bp around: |
|------|------|--------|-------------------------------|-------------------------------|-----------------------------------|
| RKS0 | At1g71830 | f14o23 | ok | OSJNBa0036B21 | 52.000 |
| RKS1 | At1g60800 | f8a5 | ok | P0038C05 | 60.000 |
| RKS2 | At5g65240 | mqn23 | ok | OJ1212_C08 | 8000 |
| RKS3 | At5g63710 | mbk5 | ok | see rks2 | |
| RKS4 | At2g23950 | t29e15 | wrong, exon missing | P0708B04 | 35.000 |
| RKS5 | At5g45780 | mra19 | wrong, exon missing | OJ1077_A12 | 102.000 |
| RKS6 | At5g10290 | wt e 23 | ok | see rks2 | |
| RKS7 | At5g16000 | ku e 24 | ok | P0038C05 | 60.000 |
| RKS8 | At1g34210 | f23m19 | ok | OJ1134_B10 | 90.000 & 1000 2 different genes! |
| RKS10 | At4g33430 | en d 25 | wrong, exon missing | see rks0 | |

TABLE-continued overview of accessions numbers of RKS signal complex genes in *arabidopsis* and in rice:

| Gene | code | contig | gene prediction in At database | *Oryza sativa japonica* contig | approximate position in bp around: |
|------|------|--------|-------------------------------|-------------------------------|-----------------------------------|
| RKS11 | At4g30520 | wu d 20 | wrong, exon missing | see rks4 | |
| RKS12 | At2g13800 | f13j11 | wrong, exon missing | see rks10 | |
| RKS13 | At2g13790 | f13j11 | ok | P0633E08 | 36.000 |
| RKS14 | At3g25560 | mw12 | wrong, exon missing | OSJNBb0015G09 | 36.000 |
| ELS1 ELS2 | At5g21090 possibly allelic variant of ELS1 no genomic sequence identified yet | ch e 52 see els1 | ok | P0003H10 | 53.000 |
| ELS3 | At3g43740 | by c 21 | ok | P0468B07 | 52.000 |

Homology between aa sequences from *arabidopsis* proteins are compared with the rice databases
protein sequences based on *Oryza sativa japonica* contig sequences.

*Arabidopsis Thaliana* RKS0 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 1)
attttattttatttttactctttgtttgttttaatgctaatgggtttt taaagggttatcgaaaaaatgagtgagtttgtgttgaggttgtctctgt aaagtgttaatggtggtgattttcggaagttagggttttctcggatctga agagatcaaatcaagattcgaaatttaccattgttgtttgaa ATG GAGT

CGAGTTATGTGGTGTTTATCTTACTTTCACTGATCTTACTTCCGAATCATT

CACTGTGGCTTGCTTCTGCTAATTTGGAAGGTGATGCTTTGCATACTTTG

AGGGTTACTCTAGTTGATCCAAACAATGTCTTGCAGAGCTGGGATCCTAC

GCTAGTGAATCCTTGCACATGGTTCCATGTCACTTGCAACAACGAGAACA

GTGTCATAAGAGTTGATTTGGGGAATGCAGAGTTATCTGGCCATTTAGTT

CCAGAGCTTGGTGTGCTCAAGAATTTGCAGTATTTGGAGCTTTACAGTAA

CAACATAACTGGCCCGATTCCTAGTAATCTTGGAAATCTGACAAACTTAG

TGAGTTTGGATCTTTACTTAAACAGCTTCTCCGGTCCTATTCCGGAATCA

TTGGGAAAGCTTTCAAAGCTGAGATTTCTCCGGCTTAACAACAACAGTCT

CACTGGGTCAATTCCTATGTCACTGACCAATATTACTACCCTTCAAGTGT

TAGATCTATCAAATAACAGACTCTCTGGTTCAGTTCCTGACAATGGCTCC

TTCTCACTCTTCACACCCATCAGTTTTGCTAATAACTTAGACCTATGTGG

ACCTGTTACAAGTCACCCATGTCCTGGATCTCCCCCGTTTTCTCCTCCAC

CACCTTTTATTCAACCTCCCCCAGTTTCCACCCCGAGTGGGTATGGTATA

-continued

```
ACTGGAGCAATAGCTGGTGGAGTTGCTGCAGGTGCTGCTTTGCCCTTTGC
TGCTCCTGCAATAGCCTTTGCTTGGTGGCGACGAAGAAGCCCACTAGATA
TTTTCTTCGATGTCCCTGCCGAAGAAGATCCAGAAGTTCATCTGGGACAG
CTCAAGAGGTTTTCTTTGCGGGAGCTACAAGTGGCGAGTGATGGGTTTAG
TAACAAGAACATTTTGGGCAGAGGTGGGTTTGGGAAAGTCTACAAGGGAC
GCTTGGCAGACGGAACTCTTGTTGCTGTCAAGAGACTGAAGGAAGAGCGA
ACTCCAGGTGGAGAGCTCCAGTTTCAAACAGAAGTAGAGATGATAAGTAT
GGCAGTTCATCGAAACCTGTTGAGATTACGAGGTTTCTGTATGACACCGA
CCGAGAGATTGCTTGTGTATCCTTACATGGCCAATGGAAGTGTTGCTTCG
TGTCTCAGAGAGAGGCCACCGTCACAACCTCCGCTTGATTGGCCAACGCG
GAAGAGAATCGCGCTAGGCTCAGCTCGAGGTTTGTCTTACCTACATGATC
ACTGCGATCCGAAGATCATTCACCGTGACGTAAAAGCAGCAAACATCCTC
TTAGACGAAGAATTCGAAGCGGTTGTTGGAGATTTCGGGTTGGCAAAGCT
TATGGACTATAAAGACACTCACGTGACAACAGCAGTCCGTGGCACCATCG
GTCACATCGCTCCAGAATATCTCTCAACCGGAAAATCTTCAGAGAAACC
GACGTTTTCGGATACGGAATCATGCTTCTAGAACTAATCACAGGACAAAG
AGCTTTCGATCTCGCTCGGCTAGCTAACGACGACGACGTCATGTTACTTG
ACTGGGTGAAAGGATTGTTGAAGGAGAAGAAGCTAGAGATGTTAGTGGAT
CCAGATCTTCAAACAAACTACGAGGAGAGAGAACTGGAACAAGTGATACA
AGTGGCGTTGCTATGCACGCAAGGATCACCAATGGAAAGACCAAAGATGT
CTGAAGTTGTAAGGATGCTGGAAGGAGATGGGCTTGCGGAGAAATGGGAC
GAATGGCAAAAAGTTGAGATTTTGAGGGAAGAGATTGATTTGAGTCCTAA
TCCTAACTCTGATTGGATTCTTGATTCTACTTACAATTTGCACGCCGTTG
AGTTATCTGGTCCAAGG TAAaaaaaaaaaaaaaaaaa
```

Predicted Amino Acid Sequence of the *Arabidopsis thaliana* RKS0 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 2)
```
MESSYVVFILLSLILLPNHSL
WLASANLEG
DALHTLRVTLVDP
NNVLQSWDPTLVN
PCTWFHVTCNNENSVIRV
DLGNAELSGHLV
P ELGVLKNLQYLELYSNNITGPI
PSNLGNLTNLVSLDLYLNSFSGPI
PESLGKLSKLRFLRLNNNSLTGSI
PMSLTNITTLQVLDLSNNRLSGSV
PDNGSFSLFTPISFANNLDLCGPV
TSHPCPGSPPFSPPPP
FIQPPPVSTPSGYGITG
AIAGGVAAGAAL
PFAAPAIAFAWW
RRRKPLDIFFDVPAEEDPE
VHLGQLKRFSLRELQVAS
DGESNKNILGRGGEGKVYKGRLAD
GTLVAVKRLKEERTPGGELQFQ
TEVEMISMAVHRNLLRLRGFCM
TPTERLLVYPYMANGSVASCLR
ERPPSQPPLDWPTRKRIALGSA
RGLSYLHDHCDPKIIHRDVKAA
NILLDEEFEAVVGDFGLAKLMD
YKDTHVTTAVRGTIGHIAPEYL
STGKSSEKTDVEGYGIMLLELI
TGQRAFDLARLANDDDVMLLDW
VKGLLKEKKLEMLVDPDLQTNY
EERELEQVIQVALLCTQGSPME
RPKMSEVVRMLE
GDGLAEKWDEWQKVEILREEIDLS
PNPNSDWILDSTYNLHAVELSGPR
```

*Arabidopsis Thaliana* RKS1 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 3)
```
ccaaagttgattgctttaagaagggat ATG GAAGGTGTGAGATTTGTGG
TGTGGAGATTAGGATTTCTGGTTTTTGTATGGTTCTTTGATATCTCTTCTG
```

```
CTACACTTTCTCCTACTGGTGTAAACTATGAAGTGACAGCTTTGGTTGCT

GTGAAGAATGAATTGAATGATCCGTACAAAGTTCTTGAGAATTGGGATGT

GAATTCAGTTGATCCTTGTAGCTGGAGAATGGTTTCTTGCACTGATGGCT

ATGTCTCTTCACTGGATCTTCCTAGCCAAAGCTTGTCTGGTACATTGTCT

CCTAGAATCGGAAACCTCACCTATTTACAATCAGTGGTGTTGCAAAACAA

TGCAATCACTGGTCCAATTCCGGAAACGATTGGGAGGTTGGAGAAGCTTC

AGTCACTTGATCTTTCGAACAATTCATTCACCGGGGAGATACCGGCCTCA

CTTGGAGAACTCAAGAACTTGAATTACTTGCGGTTAAACAATAACAGTCT

TATAGGAACTTGCCCTGAGTCTCTATCCAAGATTGAGGGACTCACTCTAG

TCGACATTTCGTATAACAATCTTAGTGGTTCGCTGCCAAAAGTTTCTGCC

AGAACTTTCAAGGTAATTGGTAATGCGTTAATCTGTGGCCCAAAAGCTGT

TTCAAACTGTTCTGCTGTTCCCGAGCCTCTCACGCTTCCACAAGATGGTC

CAGATGAATCAGGAACTCGTACCAATGGCCATCACGTTGCTCTTGCATTT

GCCGCAAGCTTCAGTGCAGCATTTTTTGTTTTCTTTACAAGCGGAATGTT

TCTTTGGTGGAGATATCGCCGTAACAAGCAAATATTTTTGACGTTAATG

AACAATATGATCCAGAAGTGAGTTTAGGGCACTTGAAGAGGTATACATTC

AAAGAGCTTAGATCTGCCACCAATCATTTCAACTCGAAGAACATTCTCGG

AAGAGGCGGATACGGGATTGTGTACAAAGGACACTTAAACGATGGAACTT

TGGTGGCTGTCAAACGTCTCAAGGACTGTAACATTGCGGGTGGAGAAGTC

CAGTTTCAGACAGAAGTAGAGACTATAAGTTTGGCTCTTCATCGCAATCT

CCTCCGGCTCCGCGGTTTCTGTAGTAGCAACCAGGAGAGAATTTTAGTCT

ACCCTTACATGCCAAATGGGAGTGTCGCATCACGCTTAAAAGATAATATC

CGTGGAGAGCCAGCATTAGACTGGTCGAGAAGGAAGAAGATAGCGGTTGG

GACAGCGAGAGGACTAGTTTACCTACACGAGCAATGTGACCCGAAGATTA

TACACCGCGATGTGAAAGCAGCTAACATTCTGTTAGATGAGGACTTCGAA

GCAGTTGTTGGTGATTTTGGGTTAGCTAAGCTTCTAGACCATAGAGACTC

TCATGTCACAACTGCAGTCCGTGGAACTGTTGGCCACATTGCACCTGAGT

ACTTATCCACGGGTCAGTCCTCAGAGAAGACTGATGTCTTTGGCTTTGGC

ATACTTCTCCTTGAGCTCATTACTGGTCAGAAAGCTCTTGATTTTGGCAG

ATCCGCACACCAGAAAGGTGTAATGCTTGACTGGGTGAAGAAGCTGCACC

AAGAAGGGAAACTAAAGCAGTTAATAGACAAAGATCTAAATGACAAGTTC

GATAGAGTAGAACTCGAAGAAATCGTTCAAGTTGCGCTACTCTGCACTCA

ATTCAATCCATCTCATCGACCGAAAATGTCAGAAGTTATGAAGATGCTTG

AAGGTGACGGTTTGGCTGAGAGATGGGAAGCGACGCAGAACGGTACTGGT

GAGCATCAGCCACCGCCATTGCCACCGGGGATGGTGAGTTCTTCGCCGCG

TGTGAGGTATTACTCGGATTATATTCAGGAATCGTCTCTTGTAGTAGAAG

CCATTGAGCTCTCGGGTCCTCGA TGAttatgactcactgttttaaaaaa
```

Predicted Amino Acid Sequence of the *Arabidopsis thaliana* RKS1 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 4)

MEGVRFVVWRLGFL

VFVWFFDISSATLSPTGVNYEV

TALVAVKNELNDP

YKVLENWDVNSVD

PCSWRMVSCTDGYVSSL

DLPSQSLSGT

LSPRIGNLTYLQSVLQNNAITGPI

PETIGRLEKLQSLDLSNNSFTGEI

PASLGELKNLNYLRLNNNSLIGTC

PESLSKIEGLTLVDISYNNLSGSL

PKVSARTFK VIGNALICGPK

AVSNCSAVPEPLTL

PQDGPDESGTRTNG

HHVALAFAASFS

AAFFVFFTSGMFLWW

RYRRNKQIFFDVNEQYDPE

VSLGHLKRYTFKELRSAT

NHFNSKNILGRGGYGIVYKGHLND

GTLVAVKRLKDCNIAGGEVQFQ

TEVETISLALHRNLLRLRGFCS

SNQERILVYPYPMPNGSVASRLK

DNIRGEPALDWSRRKKIAVGTA

RGLVYLHEQCDPKIIHRDVKAA

NILLDEDFEAVVGDFGLAKLLD

HRDSHVTTAVRGTVGHIAPEYL

STGQSSEKTDVFGFGILLLELI

TGQKALDFGRSAHQKGVMLDW

VKKLHQEGKLKQLIDKDLNDKF

DRVELEEIVQVALLCTQFNPSH

-continued

RPKMSEVMKMLE

GDGLAERWEATQNGTGEHQPPPLPPGMVSSS

PRVRYYSDYIQESSLVVEAIELSGPR

*Arabidopsis Thaliana* RKS2 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

Italics indicate the presence of an alternatively spliced gene product.

(SEQ ID NO: 5)
tcaattttggtagctcttagaaaa ATG GCTCTGCTTATTATCACTGCCT

TAGTTTTTAGTAGTTTATGGTCATCTGTGTCACCAGATGCTCAAGGGGATG

CATTATTTGCGTTGAGGAGCTCGTTACGTGCATCTCCTGAACAGCTTAGT

GATTGGAACCAGAATCAAGTCGATCCTTGTACTTGGTCTCAAGTTATTTG

TGATGACAAGAAACATGTTACTTCTGTAACCTTGTCTTACATGAACTTCT

CCTCGGGAACACTGTCTTCAGGAATAGGAATCTTGACAACTCTCAAGACT

CTTACATTGAAGGGAAATGGAATAATGGGTGGAATACCAGAATCCATTGG

AAATCTGTCTAGCTTGACCAGCTTAGATTTGGAGGATAATCACTTAACTG

ATCGCATTCCATCCACTCTCGGTAATCTCAAGAATCTACAGTTCTTCAGG

ACCTTGAGTAGGAATAACCTTAATGGTTCTATCCCGGATTCACTTACAGG

TCTATCAAAACTGATAAATATTCTGCTCGACTCAAATAATCTCAGTGGTG

AGATTCCTCAGAGTTTATTCAAAATCCCAAAATACAATTTCACAGCAAAC

AACTTGAGCTGTGGTGGCACTTTCCCGCAACCTTGTGTAACCGAGTCCAG

TCCTTCAGGTGATTCAAGCAGTAGAAAAACTGGAATCATCGCTGGAGTTG

TTAGCGGAATAGCGGTTATTCTACTAGGATTCTTCTTCTTTTTCTTCTGC

AAGGATAAACATAAAGGATATAAACGAGACGTATTTGTGGATGTTGCAGG

AACGAACTTTAAAAAAGGTTTGATTTCAGGTGAAGTGGACAGAAGGATTG

CTTTTGGACAGTTGAGAAGATTTGCATGGAGAGAGCTTCAGTTGGCTACA

GATGAGTTCAGTGAAAAGAATGTTCTCGGACAAGGAGGCTTTGGGAAAGT

TTACAAAGGATTGCTTTCGGATGGCACCAAAGTCGCTGTAAAAAGATTGA

CTGATTTTGAACGTCCAGGAGGAGATGAAGCTTTCCAGAGAGAAGTTGAG

ATGATAAGTGTAGCTGTTCATAGGAATCTGCTTCGCCTTATCGGCTTTTG

TACAACACAAACTGAACGACTTTTGGTGTATCCTTTCATGCAGAATCTAA

GTGTTGCATATTGCTTAAGAGAGATTAAACCCGGGGATCCAGTTCTGGAT

TGGTTCAGGAGGAAACAGATTGCGTTAGGTGCAGCACGAGGACTCGAATA

TCTTCATGAACATTGCAACCCGAAGATCATACACAGAGATGTGAAAGCTG

CAAATGTGTTACTAGATGAAGACTTTGAAGCAGTGGTTGGTGATTTTGGT

TTAGCCAAGTTGGTAGATGTTAGAAGGACTAATGTAACCACTCAGGTCCG

AGGAACAATGGGTCATATTGCACCAGAATGTATATCCACAGGGAAATCGT

CAGAGAAAACCGATGTTTTCGGGTACGGAATTATGCTTCTGGAGCTTGTA

ACTGGACAAAGAGCAATTGATTTCTCGCGGTTAGAGGAAGAAGATGATGT

CTTATTGCTAGACCATGTGAAGAAACTGGAAAGAGAGAAGAGATTAGAAG

ACATAGTAGATAAGAAGCTTGATGAGGATTATATAAAGGAAGAAGTTGAA

ATGATGATACAAGTAGCTCTGCTATGCACACAAGCAGCACCGGAAGAACG

ACCAGCGATGTCGGAAGTAGTAAGAATGCTAGAAGGAGAAGGGCTTGCAG

AGAGATGGGAAGAGTGGCAGAATCTTGAAGTGACAGACAAGAAGAGTTT

CAGAGGTTGCAGAGGAGATTTGATTGGGGTGAAGATTCCATTAATAATCA

AGATGCTATTGAATTATCTGGTGGAAGA <u>TAG</u>aaacaaaaaa

Predicted Amino Acid Sequence of the *Arabidopsis thaliana* RKS2 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 3 complete and 2 incomplete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions. Italics indicate an alternatively spliced gene product.

(SEQ ID NO: 6)
MALLIITALVFSSL

WSSVSPDAQG

DALFALRSSLR

ASPEQLSDWNQNQVD

PCTWSQVICDDKKHVTSV

TLSYMNFSS GTLSSGI

GILTTLKTLTLKGNGIMGGI

PESIGNLSSLTSLDLEDNHLTDRI

PSTLGNLKNLQFLTLSRNNLNGSI

PDSLTGLSKLINILLDSNNLSGEI

PQSLFKIPKYN FTANNLSCGG

TFPQPCVTESSPSGDSSSRKTG

IIAGVVSGIAVIL

LGFFFFFFC

KDKHKGYKRDVFVDVAGTNFKKGLISGE

VDRRIAFGQLRRFAWRELQLAT

DEFSEKNVLGQGGFGKVYKGLLSD

GTKVAVKRLTDFERPGGDEAFQ

REVEMISVAVHRNLLRLIGFCT

TQTERLLVYPFMQNLSVAYCLR

EIKPGDPVLDWFRRKQIALGAA

RGLEYLHEHCNPKIIHRDVKAA

NVLLDEDFEAVVGDFGLAKLVD

VRRTNVTTQVRGTMGHIAPECI

STGKSSEKTDVFGYGIMLLELV

TGQRAIDFSRLEEEDDVLLLDH

VKKLEREKRLEDIVDKKLDEDY

IKEEVEMMIQVALLCTQAAPEE

RPAMSEVVRMLE

GEGLAERWEEWQNLEVTRQEEFQ

RLQRRFDWGEDSINNQDAIELSGGR

*Arabidopsis Thaliana* RKS3 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 7)

aacggtgaaagtttccatgatcctcttcgaggattcattcaaagaaattg ctttagatggaacaatcagaaattgatcttacaatgtttc ATG GCCTT

AGCTTTTGTGGGAATCACTTCGTCAACAACTCAACCAGATATCGAAGGAG

GAGCTCTGTTGCAGCTCAGAGATTCGCTTAATGATTCGAGCAATCGTCTA

AAATGGACACGCGATTTTGTGAGCCCTTGCTATAGTTGGTCTTATGTTAC

CTGCAGAGGCCAGAGTGTTGTGGCTCTAAATCTTGCCTCGAGTGGATTCA

CAGGAACACTCTCTCCAGCTATTACAAAACTGAAGTTCTTGGTTACCTTA

GAGTTACAGAACAATAGTTTATCTGGTGCCTTACCAGATTCTCTTGGGAA

CATGGTTAATCTACAGACTTTAAACCTATCAGTGAATAGTTTCAGCGGAT

CGATACCAGCGAGCTGGAGTCAGCTCTCGAATCTAAAGCACTTGGATCTC

TCATCCAATAATTTAACAGGAAGCATCCCAACACAATTCTTCTCAATCCC

AACATTCGATTTTTCAGGAACTCAGCTTATATGCGGTAAAAGTTTGAATC

AGCCTTGTTCTTCAAGTTCTCGTCTTCCAGTCACATCCTCCAAGAAAAAG

CTGAGAGACATTACTTTGACTGCAAGTTGTGTTGCTTCTATAATCTTATT

CCTTGGAGCAATGGTTATGTATCATCACCATCGCGTCCGCAGAACCAAAT

ACGACATCTTTTTTGATGTAGCTGGGGAAGATGACAGGAAGATTTCCTTT

GGACAACTAAAACGATTCTCTTTACGTGAAATCCAGCTCGCAACAGATAG

TTTCAACGAGAGCAATTTGATAGGACAAGGAGGATTTGGTAAAGTATACA

GAGGTTTGCTTCCAGACAAAACAAAAGTTGCAGTGAAACGCCTTGCGGAT

TACTTCAGTCCTGGAGGAGAAGCTGCTTTCCAAAGAGAGATTCAGCTCAT

AAGCGTTGCGGTTCATAAAAATCTCTTACGCCTTATTGGCTTCTGCACAA

CTTCCTCTGAGAGAATCCTTGTTTATCCATACATGGAAAATCTTAGTGTT

GCATATCGACTAAGAGATTTGAAAGCGGGAGAGGAAGGATTAGACTGGCC

AACAAGGAAGCGTGTAGCTTTTGGTTCAGCTCACGGTTTAGAGTATCTAC

ACGAACATTGTAACCCGAAGATCATACACCGCGATCTCAAGGCTGCAAAC

ATACTTTTAGACAACAATTTTGAGCCAGTTCTTGGAGATTTCGGTTTAGC

TAAGCTTGTGGACACATCTCTGACTCATGTCACAACTCAAGTCCGAGGCA

CAATGGGTCACATTGCGCCAGAGTATCTCTGCACAGGAAAATCATCTGAA

AAAACCGATGTTTTTGGTTACGGTATAACGCTTCTTGAGCTTGTTACTGG

TCAGCGCGCAATCGATTTTTCACGCTTGGAAGAAGAGGAAAATATTCTCT

TGCTTGATCATATAAAGAAGTTGCTTAGAGAACAGAGACTTAGAGACATT

GTTGATAGCAATTTGACTACATATGACTCCAAAGAAGTTGAAACAATCGT

TCAAGTGGCTCTTCTCTGCACACAAGGCTCACCAGAAGATAGACCAGCGA

TGTCTGAAGTGGTCAAAATGCTTCAAGGGACTGGTGGTTTGGCTGAGAAA

TGGACTGAATGGGAACAACTTGAAGAAGTTAGGAACAAAGAAGCATTGTT

GCTTCCGACTTTACCGGCTACTTGGGATGAAGAAGAAACCACCGTTGATC

AAGAATCTATCCGATTATCGACAGCAAGA <u>TGA</u> agaagaaacagagaga gaaagatatctatgaaaa

Predicted Amino Acid Sequence of the *Arabidopsis thaliana* RKS3 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 8)

MALAFVGITSSTTQPDIEG

GALLQLRDSLNDSSNRL

KWTRDFVS

PCYSWSYVTCRGQSVVAL

NLASSGFTGTLS

P AITKLKFLVTLELQNNSLSGAL

PDSLGNMVNLQTLNLSVNSFSGSI

PASWSQLSNLKHLDLSSNNLTGSI

PTQFFSIPTFEFSGTQLICGKS

LNQPCSSSRLPVTSSKKKLRD

ITLTASCVASIIL

FLGAMVMYHHH

RVRRTKYDIFFDVAGEDDR

KISFGQLKRFSLREIQLAT

DSFNESNLIGQGGFGKVYRGLLPD

KTKVAVKRLADYFSPGGEAAFQ

REIQLISVAVHKNLLRLIGFCT

TSSERILVYPYMENLSVAYRLR

DLKAGEEGLDWPTRKRVAFGSA

HGLEYLHEHCNPKIIHRDLKAA

NILLDNNFEPVLGDFGLAKLVD

TSLTHVTTQVRGTMGHIAPEYL

CTGKSSEKTDVFGYGITLLELV

TGQRAIDFSRLEEEENILLLD

HIKKLLREQRLRDIVDSNLTTY

DSKEVETIVQVALLCTQGSPED

RPAMSEVVKMLQ

GTGGLAEKWTEWEQLEEVRNKEALLL

PTLPATWDEEETTVDQESIRLSTAR

*Arabidopsis Thaliana* RKS4 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 9)
tcttccttctccttctggtaatctaatctaaagcttttc ATG GTGGTG

ATGAAGATATTCTCTGTTCTGTTACTACTATGTTTCTTCGTTACTTGTTC

TCTCTCTTCTGAACCCAGAAACCCTGAAGTGGAGGCGTTGATAAACATAA

AGAACGAGTTACATGATCCACATGGTGTTTTCAAAAACTGGGATGAGTTT

TCTGTTGATCCTTGTAGCTGGACTATGATCTCTTGTTCTTCAGACAACCT

CGTAATTGGCTTAGGAGCTCCAAGTCAGTCTCTTTCAGGAACTTTATCTG

GGTCTATTGGAAATCTCACTAATCTTCGACAAGTGTCATTACAGAACAAT

AACATCTCCGGTAAAATCCCACCGGAGATTTGTTCTCTTCCCAAATTACA

GACTCTGGATTTATCCAATAACCGGTTCTCCGGTGAAATCCCCGGTTCTG

TTAACCAGCTGAGTAATCTCCAATATCTGTTGAACAACAACTCATTATCT

GGGCCCTTTCCTGCTTCTCTGTCTCAAATCCCTCACCTCTCTTTCTTAGA

CTTGTCTTATAACAATCTCAGAGGTCCTGTTCCTAAATTTCCTGCAAGGA

CATTCAATGTTGCTGGGAACCCTTTGATTTGTAAAAACAGCCTACCGGAG

ATTTGTTCAGGATCAATCAGTGCAAGCCCTCTTTCTGTCTCTTTACGTTC

TTCATCAGGACGTAGAACCAACATATTAGCAGTTGCACTTGGTGTAAGCC

TTGGCTTTGCTGTTAGTGTAATCCTCTCTCTCGGGTTCATTTGGTATCGA

AAGAAACAAAGACGGTTAACGATGCTTCGCATTAACAAGCAAGAGGAAGG

GTTACTTGGGTTGGGAAATCTAAGAAGCTTCACATTCAGGGAACTTCATG

TAGCTACGGATGGTTTTAGTTCCAAGAGTATTCTTGGTGCTGGTGGGTTC

GGTAATGTCTACAGAGGAAAATTCGGGGATGGGACAGTGGTTGCAGTGAA

ACGATTGAAAGATGTGAATGGAACCTCCGGGAACTCACAGTTTCGTACTG

AGCTTGAGATGATCAGCTTAGCTGTTCATAGGAATTTGCTTCGGTTAATC

GGTTATTGTGCGAGTTCTAGCGAAAGACTTCTTGTTTACCCTTACATGTC

CAATGGCAGCGTCGCCTCTAGGCTCAAAGCTAAGCCAGCGTTGGACTGGA

ACACAAGGAAGAAGATAGCGATTGGAGCTGCAAGAGGGTTGTTTTATCTA

CACGAGCAATGCGATCCCAAGATTATTCACCGAGATGTCAAGGCAGCAAA

CATTCTCCTAGATGAGTATTTTGAAGCACTTGTTGGGGATTTTGGACTAG

CAAAGCTACTCAACCACGAGGATTCACATGTCACAACCGCGGTTAGAGGA

ACTGTTGGTCACATTGCACCTGAGTATCTCTCCACCGGTCAGTCATCTGA

GAAAACCGATGTCTTTGGGTTCGGTATACTTTTGCTAGAGCTCATCACAG

GAATGAGAGCTCTCGAGTTTGGCAAGTCTGTTAGCCAGAAAGGAGCTATG

CTAGAATGGGTGAGGAAGCTACACAAGGAAATGAAAGTAGAGGAGCTAGT

AGACCGAGAACTGGGGACAACCTACGATAGAATAGAAGTTGGAGAGATGC

TACAAGTGGCACTGCTCTGCACTCAGTTTCTTCCAGCTCACAGACCCAAA

ATGTCTGAAGTAGTTCAGATGCTTGAAGGAGATGGATTAGCTGAGAGATG

GGCTGCTTCACATGACCATTCACATTTCTACCATGCCAACATGTCTTACA

GGACTATTACCTCTACTGATGGCAACAACCAAACCAAACATCTGTTTGGC

TCCTCAGGATTTGAAGATGAAGATGATAATCAAGCCTTAGATTCATTCGC

CATGGAACTATCTGGTCCAAGG <u>TAG</u> taaatcttggacacagaaagaac agatataatatccccatgacttcaattttttgtt Predicted Amino Acid Sequence of the *Arabidopsis thaliana* RKS4 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 2 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 10)
```
MVVMKLITMKIFSVLLLL
CFFVTCSLSSEPRNPEV
EALINIKNELHDP
HGVFKNWDEFSVD
PCSWTMISCSSDNLVIGL
GAPSQSLSGTLS
G SIGNLTNLRQVSLQNNNISGKI
PPEICSLPKLQTLDLSNNRFSGEI
PGSVNQLSNLQYLRLNNNSLSGPPF
PASLSQIPHLSFLDLSYNNLRGPV
PKFPARTFNVAGNPLICKNS
LPEICSGSISASPL
SVSLRSSSGRRTN
ILAVALGVSLGFAVSVIL
SLGFIWY
RKKQRRLTMLRINKQEE
GLLGLGNLRSFTFRELHVAT
DGFSSKSILGAGGFGNVYRGKFGD
GTVVAVKRLKDVNGTSGNSQFR
TELEMISLAVHRNLLRLIGYCA
SSSERLLVYPYMSNGSVASRLK
AKPALDWNTRKKIAIGAA
RGLFYLHEQCDPKIIHRDVKAA
NILLDEYFEAVVGDFGLAKLLN
HEDSHVTTAVRGTVGHIAPEYL
STGQSSEKTDVFGFGILLLELI
TGMRALEFGKSVSQKGAMLEW
VRKLHKEMKVEELVDRELGTTY
DRIEVGEMLQVALLCTQFLPAH
RPKMSEVVQMLE
GDGLAERWAASHDHSHFYHANM
SYRTITSTDGNNQTKHLFG
SSGFEDEDDNQALDSFAMELSGPR
```

*Arabidopsis Thaliana* RKS5 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 11)
```
ctagagaattcttatactttttctacg ATG GAGATTTCTTTGATGAAG
TTTCTGTTTTTAGGAATCTGGGTTTATTATTACTCTGTTCTTGACTCTGT
TTCTGCCATGGATAGTCTTTTATCTCCCAAGGTGGCTGCGTTAATGTCAG
TGAAGAACAAGATGAAAGATGAGAAAGAGGTTTTGTCTGGTTGGGATATT
AACTCTGTTGATCCTTGTACTTGGAACATGGTTGGTTGTTCTTCTGAAGG
TTTTGTGGTTTCTCTAGAGATGGCTAGTAAAGGATTATCAGGGATACTAT
CTACTAGTATTGGGGAATTAACTCATCTTCATACTTTGTTACTTCAGAAT
AATCAGTTAACTGGTCCGATTCCTTCTGAGTTAGGCCAACTCTCTGAGCT
TGAAACGCTTGATTTATCGGGGAATCGGTTTAGTGGTGAAATCCCAGCTT
CTTTAGGGTTCTTAACTCACTTAAACTACTTGCGGCTTAGCAGGAATCTT
TTATCTGGGCAAGTCCCTCACCTCGTCGCTGGCCTCTCAGGTCTTTCTTT
CTTGGATCTATCTTTCAACAATCTAAGCGGACCAACTCCGAATATATCAG
CAAAAGATTACAGGAAATGCATTTCTTTGTGGTCCAGCTTCCCAAGAGCT
TTGCTCAGATGCTACACCTGTGAGAAATGCTGCAATCGATCTGCAGCGAC
GGGTTTGTCTGAAAAGGACAATAGCAAACATCACAGCTTAGTGCTCTCTT
TTGCATTTGGCATTGTTGTTGCCTTTATCATCTCCCTAATGTTTCTCTTC
TTCTGGGTGCTTTGGCATCGATCACGTCTCTCAAGATCACACGTGCAGCA
AGACTACGAATTTGAAATCGGCCATCTGAAAAGGTTCAGTTTTCGCGAAA
TACAAACCGCAACAAGCAATTTTAGTCCAAAGAACATTTTGGGACAAGGA
GGGTTTGGGATGGTTTATAAAGGGTATCTCCCAAATGGAACTGTGGTGGC
AGTTAAAAGATTGAAAGATCCGATTTATACAGGAGAAGTTCAGTTTCAAA
CCGAAGTAGAGATGATTGGCTTAGCTGTTCACCGTAACCTTTTACGCCTC
TTTGGATTCTGTATGACCCCGGAAGAGAGAATGCTTGTGTATCCGTACAT
GCCAAATGGAAGCGTAGCTGATCGTCTGAGAGATTGGAATCGGAGGATAA
GCATTGCACTCGGCGCAGCTCGAGGACTTGTTTACTTGCACGAGCAATGC
AATCCAAAGATTATTCACAGAGACGTCAAAGCTGCAAATATTCTACTTGA
TGAGAGCTTTGAAGCAATAGTTGGCGATTTTGGTCTAGCAAAGCTTTTAG
ACCAGAGAGATTCACATGTCACTACCGCAGTCCGAGGAACCATTGGACAC
ATCGCTCCCGAGTACCTTTCCACTGGACAGTCCTCAGAGAAAACCGATGT
TTTCGGATTCGGAGTACTAATCCTTGAACTCATAACAGGTCATAAGATGA
TTGATCAAGGCAATGGTCAAGTTCGAAAAGGAATGATATTGAGCTGGGTA
AGGACATTGAAAGCAGAGAAGAGATTTGCAGAGATGGTGGACAGAGATTT
GAAGGGAGAGTTTGATGATTTGGTGTTGGAGGAAGTAGTGGAATTGGCTT
TGCTTTGTACACAGCCACATCCGAATCTAAGACCGAGGATGTCTCAAGTG
TTGAAGGTACTAGAAGGTTTAGTGGAACAGTGTGAAGGAGGGTATGAAGC
```

```
-continued
TAGAGCTCCAAGTGTCTCTAGGAACTACAGTAATGGTCATGAAGAGCAGT

CCTTTATTATTGAAGCCATTGAGCTCTCTGGACCACGA TGA tagactt catagtgtcttaactagtcttcttgattttgttgtcattgtcatggc
```

Predicted Amino Acid Sequence of the *Arabidopsis thaliana* RKS5 Protein.

Different domains are spaced and shown from the N-terminus towards the C-terminus. Overall domain structure is similar as described in Schmidt et al (1997).

At the predicted extracellular domain the first domain represents a signal sequence. The second domain contains no leucine zipper motif, in contrast to the other RKS proteins. The third domain contains conserved cysteine residues, involved in disulphate bridge formation. The fourth domain contains a leucine rich repeat domain, consisting of 5 complete repeats of each approximately 24 amino acid residues. The fifth domain contains many serine residues, and is likely to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
                                    (SEQ ID NO: 12)
MEISLMKFLFLGIWVYYS

VLDSVSAMDSLLSPKV

AALMSVKNKMKDE

KEVLSGWDINSVD

PCTWNMVGCSSEGFVVS

LEMASKGLSGILS

T SIGELTHLHTLLLQNNQLTGPI

PSELGQLSELETLDLSGNRFSGEI

PASLGFLTHLNYLRLSRNLLSGQV

PHLVAGLSGLSFLDLSFNNLSGPT

PNISAK DYRKCISLWSSFPR

ALLRCYTCEKCCNR

SAATGLSEKDNSK

HHSLVLSFAFGIVV

AFIISLMFLFFWVLWH

RSRLSRSHVQQDYEF

EIGHLKRFSFREIQTAT

SNFSPKNILGQGGFGMVYKGYLPN

GTVVAVKRLKDPIYTGEVQFQ

TEVEMIGLAVHRNLLRLFGFCM

TPEERMLVYPYMPNGSVADRLR

DWNRRISIALGAA

RGLVYLHEQCNPKIIHRDVKAA

NILLDESFEAIVGDFGLAKLLD

QRDSHVTTAVRGTIGHIAPEYL

STGQSSEKTDVFGFGVLILELI

TGHKMIDQGNGQVRKGMILSW

VRTLKAEKRFAEMVDRDLKGEF

DDLVLEEVVELALLCTQPHPNL

RPRMSQVLKV

LEGLVEQCEGGYEARA

PASVSRNYSNGHEEQSFIIEAIELSGPR
```

*Arabidopsis Thaliana* RKS6 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
                                    (SEQ ID NO: 13)
attgtttccttcttttgggattttctccttggatggaaccagctcaatta atgagatgag ATG AGAATGTTCAGCTTGCAGAAGATGGCTATGGCTTT

TACTCTCTTGTTTTTTGCCTGTTTATGCTCATTTGTGTCTCCAGATGCTC

AAGGGGATGCACTGTTTGCGTTGAGGATCTCCTTACGTGCATTACCGAAT

CAGCTAAGTGACTGGAATCAGAACCAAGTTAATCCTTGCACTTGGTCCCA

AGTTATTTGTGATGACAAAAACTTTGTCACTTCTCTTACATTGTCAGATA

TGAACTTCTCGGGAACCTTGTCTTCAAGAGTAGGAATCCTAGAAAATCTC

AAGACTCTTACTTTAAAGGGAAATGGAATTACGGGTGAAATACCAGAAGA

CTTTGGAAATCTGACTAGCTTGACTAGTTTGGATTTGGAGGACAATCAGC

TAACTGGTCGTATACCATCCACTATCGGTAATCTCAAGAAACTTCAGTTC

TTGACCTTGAGTAGGAACAAACTTAATGGGACTATTCCGGAGTCACTCAC

TGGTCTTCCAAACCTGTTAAACCTGCTGCTTGATTCCAATAGTCTCAGTG

GTCAGATTCCTCAAAGTCTGTTTGAGATCCCAAAATATAATTTCACGTCA

AACAACTTGAATTGTGGCGGTCGTCAACCTCACCCTTGTGTATCCGCGGT

TGCCCATTCAGGTGATTCAAGCAAGCCTAAAACTGGCATTATTGCTGGAG

TTGTTGCTGGAGTTACAGTTGTTCTCTTTGGAATCTTGTTGTTTCTGTTC

TGCAAGGATAGGCATAAAGGATATAGACGTGATGTGTTTGTGGATGTTGC

AGGTGAAGTGGACAGGAGAATTGCATTTGGACAGTTGAAAAGGTTTGCAT

GGAGAGAGCTCCAGTTAGCGACAGATAACTTCAGCGAAAAGAATGTACTT

GGTCAAGGAGGCTTTGGGAAAGTTTACAAAGGAGTGCTTCCGGATACACC

CAAAGTTGCTGTGAAGAGATTGACGGATTTCGAAAGTCCTGGTGGAGATG

CTGCTTTCCAAAGGGAAGTAGAGATGATAAGTGTAGCTGTTCATAGGAAT

CTACTCCGTCTTATCGGGTTCTGCACCACACAAACAGAACGCCTTTTGGT

TTATCCCTTCATGCAGAATCTAAGTCTTGCACATCGTCTGAGAGAGATCA
```

```
AAGCAGGCGACCCGGTTCTAGATTGGGAGACGAGGAAACGGATTGCCTTA
GGAGCAGCGCGTGGTTTTGAGTATCTTCATGAACATTGCAATCCGAAGAT
CATACATCGTGATGTGAAAGCAGCTAATGTGTTACTAGATGAAGATTTTG
AAGCAGTGGTTGGTGATTTTGGTTTAGCCAAGCTAGTAGATGTTAGAAGG
ACTAATGTGACTACTCAAGTTCGAGGAACAATGGGTCACATTGCACCAGA
ATATTTATCAACAGGGAAATCATCAGAGAGAACCGATGTTTTCGGGTATG
GAATTATGCTTCTTGAGCTTGTTACAGGACAACGCGCAATAGACTTTTCA
CGTTTGGAGGAAGAAGATGATGTCTTGTTACTTGACCACGTGAAGAAACT
GGAAAGAGAGAAGAGATTAGGAGCAATCGTAGATAAGAATTTGGATGGAG
AGTATATAAAAGAAGAAGTAGAGATGATGATACAAGTGGCTTTGCTTTGT
ACACAAGGTTCACCAGAAGACCGACCAGTGATGTCTGAAGTTGTGAGGAT
GTTAGAAGGAGAAGGGCTTGCGGAGAGATGGGAAGAGTGGCAAAACGTGG
AAGTCACGAGACGTCATGAGTTTGAACGGTTGCAGAGGAGATTTGATTGG
GGTGAAGATTCTATGCATAACCAAGATGCCATTGAATTATCTGGTGGAAG
A TGA ccaaaaacatcaaacctt
```

Predicted Amino Acid Sequence of the *Arabidopsis thaliana* RKS6 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 14)
```
MRMFSL
QKMAMAFTLLFFACLCSFVSPDAQG
DALFALRISLRALP
NQLSDWNQNQVN
PCTWSQVICDDKNFVTSL
TLSDMNFSGTLSSRV
GILENLKTLTLKGNGITGEI
PEDFGNLTSLTSLDLEDNQLTGRI
PSTIGNLKKLQFLTLSRNKLNGTI
PESLTGLPNLLNLLLDSNSLSGQI
PQSLFEIPKYNFTSNNLNCGG
RQPHPCVSAVAHSGDSSKPKTG
IIAGVVAGVTVVL
FGILLFLFC
KDRHKGYRRDVFVDVAGE
VDRRIAFGQLKRFAWRELQLAT
DNFSEKNVLGQGGFGKVYKGVLPD
TPKVAVKRLTDFESPGGDAAFQ
REVEMISVAVHRNLLRLIGFCT
TQTERLLVYPFMQNLSLAHRLR
EIKAGDPVLDWETRKRIALGAA
RGFEYLHEHCNPKIIHRDVKAA
NVLLDEDFEAVVGDFGLAKLVD
VRRTNVTTQVRGTMGHIAPEYL
STGKSSERTDVFGYGIMLLELV
TGQRAIDFSRLEEEDDVLLLDH
VKKLEREKRLGAIVDKNLDGEY
IKEEVEMMIQVALLCTQGSPED
RPVMSEVVRMLE
GEGLAERWEEWQNVEVTRRHEFE
RLQRRFDWGEDSMHNQDAIELSGGR
```

*Arabidopsis Thaliana* RKS7 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 15)
```
acatcttgttttctgctcattcctctgtttcaaca ATG GAGAGTACTA
TTGTTATGATGATGATGATAACAAGATCTTTCTTTTGCTTCTTGGGATTT
TTATGCCTTCTCTGCTCTTCTGTTCACGGATTGCTTTCTCCTAAAGGTGT
TAACTTTGAAGTGCAAGCTTTGATGGACATAAAAGCTTCATTACATGATC
CTCATGGTGTTCTTGATAACTGGGATAGAGATGCTGTTGATCCTTGTAGT
TGGACAATGGTCACTTGTTCTTCTGAAAACTTTGTCATTGGCTTAGGCAC
ACCAAGTCAGAATTTATCTGGTACACTATCTCCAAGCATTACCAACTTAA
CAAATCTTCGGATTGTGCTGTTGCAGAACAACAACATAAAAGGAAAAATT
CCTGCTGAGATTGGTCGGCTTACGAGGCTTGAGACTCTTGATCTTTCTGA
TAATTTCTTCCACGGTGAAATTCCTTTTTCAGTAGGCTATCTACAAAGCC
TGCAATATCTGAGGCTTAACAACAATTCTCTCTCTGGAGTGTTTCCTCTG
TCACTATCTAATATGACTCAACTTGCCTTTCTTGATTTATCATACAACAA
```

```
TCTTAGTGGTCCTGTTCCAAGATTTGCTGCAAAGACGTTTAGCATCGTTG

GGAACCCGCTGATATGTCCAACGGGTACCGAACCAGACTGCAATGGAACA

ACATTGATACCTATGTCTATGAACTTGAATCAAACTGGAGTTCCTTTATA

CGCCGGTGGATCGAGGAATCACAAAATGGCAATCGCTGTTGGATCCAGCG

TTGGGACTGTATCATTAATCTTCATTGCTGTTGGTTTGTTTCTCTGGTGG

AGACAAAGACATAACCAAAACACATTCTTTGATGTTAAAGATGGGAATCA

TCATGAGGAAGTTTCACTTGGAAACCTGAGGAGATTTGGTTTCAGGGAGC

TTCAGATTGCGACCAATAACTTCAGCAGTAAGAACTTATTGGGGAAAGGT

GGCTATGGAAATGTATACAAAGGAATACTTGGAGATAGTACAGTGGTTGC

AGTGAAAAGGCTTAAAGATGGAGGAGCATTGGGAGGAGAGATTCAGTTTC

AGACAGAAGTTGAAATGATCAGTTTAGCTGTTCATCGAAATCTCTTAAGA

CTCTACGGTTTCTGCATCACACAAACTGAGAAGCTTCTAGTTTATCCTTA

TATGTCTAATGGAAGCGTTGCATCTCGAATGAAAGCAAAACCTGTTCTTG

ACTGGAGCATAAGGAAGAGGATAGCCATAGGAGCTGCAAGAGGGCTTGTG

TATCTCCATGAGCAATGTGATCCGAAGATTATCCACCGCGATGTCAAAGC

AGCGAATATACTTCTTGATGACTACTGTGAAGCTGTGGTTGGCGATTTTG

GTTTAGCTAAACTCTTGGATCATCAAGATTCTCATGTGACAACCGCGGTT

AGAGGCACGGTGGGTCACATTGCTCCAGAGTATCTCTCAACTGGTCAATC

CTCTGAGAAAACAGATGTTTTTGGCTTCGGGATTCTTCTTCTTGAGCTTG

TAACCGGACAAAGAGCTTTTGAGTTTGGTAAAGCGGCTAACCAGAAAGGT

GTGATGCTTGATTGGGTTAAAAAGATTCATCAAGAGAAGAAACTTGAGCT

ACTTGTGGATAAAGACTTGTTGAAGAAGAAGAGCTACGATGAGATTGAGT

TAGACGAAATGGTAAGAGTAGCTTTGTTGTGCACACAGTACCTGCCAGGA

CATAGACCAAAAATGTCTGAAGTTGTTCGAATGCTGGAAGGAGATGGACT

TGCAGAGAAATGGGAAGCTTCTCAAAGATCAGACAGTGTTTCAAAATGTA

GCAACAGGATAAATGAATTGATGTCATCTTCAGACAGATACTCTGATCTT

ACCGATGACTCTAGTTTACTTGTGCAAGCAATGGAGCTCTCTGGTCCTAG

A TGA aatctatacatgaatctgaagaagaagaagaacatgcatctgtt tcttgaatcaagagggattcttgttttttgtataatagagaggttttt ggagggaaatgttgtgtctctgtaactgtataggcttgttgtgtaagaag ttattactgcacttagggttaattcaaagttctttacataaaaaatgatt agttgcgttgaatagagggaacactttgggagatttcatgtatgaaattt ggaaaaaaaaaaaaaaaaaaa
```

Predicted Amino Acid Sequence of the *Arabidopsis thaliana* RKS7 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 16)

MESTIVMMMMITRSFF

CFLGFLCLLCSSVHGLLSPKGVNFEV

QALMDIKASLHDP

HGVLDNWDRDAVD

PCSWTMVTCSSENFVIG

LGTPSQNLSGTL

SPSITNLTNLRIVLLQNNNIKGKI

PAEIGRLTRLETLDLSDNFFHGEI

PFSVGYLQSLQYLRLNNNSLSGVF

PLSLSNMTQLAFLDLSYNNLSGPV

PRFAA KTFSIVGNPLICPT

GTEPDCNGTTLIPMSMNL

NQTGVPLYAGGSRNHKMA

IAVGSSVGTVSLIFIAVGLFLWW

RQRHNQNTFFDVKDGNHHE

EVSLGNLRRFGFRELQIAT

NNFSSKNLLGKGGYGNVYKGILGD

STVVAVKRLKDGGALGGEIQFQ

TEVEMISLAVHRNLLRLYGFCI

TQTEKLLVYPYMSNGSVA

SRMKAKPVLDWSIRKRIAIGAA

RGLVYLHEQCDPKIIHRDVKAA

NILLDDYCEAVVGDFGLAKLLD

HQDSHVTTAVRGTVGHIAPEYL

STGQSSEKTDVFGFGILLLELV

TGQRAFEFGKAANQKGVMLDW

VKKIHQEKKLELLVDKELLKKKSY

DEIELDEMVRVALLCTQYLPGH

RPKMSEVVRMLE

GDGLAEKWEASQRSDS

VSKCSNRINELMSSS

DRYSDLTDDSSLLVQAMELSGPR

Arabidopsis Thaliana RKS8 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 17)

gtttttttttttttaccctcttggaggatctgggaggagaaatttgctttttttttggtaa ATG GGGAGAAAAAGTTTGAAGCTTTTGGTTTTGTCTG
CTTAATCTCACTGCTTCTTCTGTTTAATTCGTTATGGCTTGCCTCTTCTA
ACATGGAAGGTGATGCACTGCACAGTTTGAGAGCTAATCTAGTTGATCCA
AATAATGTCTTGCAAAGCTGGGATCCTACGCTTGTTAATCCGTGTACTTG
GTTTCACGTAACGTGTAACAACGAGAACAGTGTTATAAGAGTCGATCTTG
GGAATGCAGACTTGTCTGGTCAGTTGGTTCCTCAGCTAGGTCAGCTCAAG
AACTTGCAGTACTTGGAGCTTTATAGTAATAACATAACCGGGCCGGTTCC
AAGCGATCTTGGGAATCTGACAAACTTAGTGAGCTTGGATCTTTACTTGA
ACAGCTTCACTGGTCCAATTCCAGATTCTCTAGGAAAGCTATTCAAGCTT
CGCTTTCTTCGGCTCAACAATAACAGTCTCACCGGACCAATTCCCATGTC
ATTGACTAATATCATGACCCTTCAAGTTTTGGATCTGTCGAACAACCGAT
TATCCGGATCTGTTCCTGATAATGGTTCCTTCTCGCTCTTCACTCCCATC
AGTTTTGCTAACAACTTGGATCTATGCGGCCCAGTTACTAGCCGTCCTTG
TCCTGGATCTCCCCCGTTTTCTCCTCCACCACCTTTTATACCACCTCCCA
TAGTTCCTACACCAGGTGGGTATAGTGCTACTGGAGCCATTGCGGGAGGA
GTTGCTGCTGGTGCTGCTTTACTATTTGCTGCCCCTGCTTTAGCTTTTGC
TTGGTGGCGTAGAAGAAAACCTCAAGAATTCTTCTTTGATGTTCCTGCCG
AAGAGGACCCTGAGGTTCACTTGGGGCAGCTTAAGCGGTTCTCTCTACGG
GAACTTCAAGTAGCAACTGATAGCTTCAGCAACAAGAACATTTTGGGCCG
AGGTGGGTTCGGAAAAGTCTACAAAGGCCGTCTTGCTGATGGAACACTTG
TTGCAGTCAAACGGCTTAAAGAAGAGCGAACCCCAGGTGGCGAGCTCCAG
TTTCAGACAGAAGTGGAGATGATAAGCATGGCCGTTCACAGAAATCTCCT
CAGGCTACGCGGTTTCTGTATGACCCCTACCGAGAGATTGCTTGTTTATC
CTTACATGGCTAATGGAAGTGTCGCTTCCTGTTTGAGAGAACGTCCACCA
TCACAGTTGCCTCTAGCCTGGTCAATAAGACAGCAAATCGCGCTAGGATC
AGCGAGGGGTTTGTCTTATCTTCATGATCATTGCGACCCCAAAATTATTC
ACCGTGATGTGAAAGCTGCTAATATTCTGTTGGACGAGGAATTTGAGGCG
GTGGTAGGTGATTTCGGGTTAGCTAGACTTATGGACTATAAAGATACTCA
TGTCACAACGGCTGTGCGTGGGACTATTGACACATTGCTCCTGAGTATC
TCTCAACTGGAAAATCTTCAGAGAAAACTGATGTTTTGGCTACGGGATC
ATGCTTTTGGAACTGATTACAGGTCAGAGAGCTTTTGATCTTGCAAGACT
GGCGAATGACGATGACGTTATGCTCCTAGATTGGGTGAAAGGGCTTTTGA
AGGAGAAGAAGCTGGAGATGCTTGTGGATCCTGACCTGCAAAGCAATTAC
ACAGAAGCAGAAGTAGAACAGCTCATACAAGTGGCTCTTCTCTGCACACA GAGCTCACCTATGGAACGACCTAAGATGTCTGAGGTTGTTCGAATGCTTG
AAGGTGACGGTTTAGCGGAGAAATGGGACGAGTGGCAGAAAGTGGAAGTT
CTCAGGCAAGAAGTGGAGCTCTCTTCTCACCCCACCTCTGACTGGATCCT
TGATTCGACTGATAATCTTCATGCTATGGAGTTGTCTGGTCCAAGA <u>TAA</u>
acgacattgtaatttgcctaacagaaaagagaaagaacagagaaatatta
agagaatcacttctctgtattctt Predicted Amino Acid Sequence of the *Arabidopsis Thaliana* RKS8 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 18)

MGRKKFEAFGFVCLISLLLLFNSL

WLASSNMEG

DALHSLRANLVDP

NNVLQSWDPTLVN

PCTWFHVTCNNENSVIRV

DLGNADLSGQLV

PQLGQLKNLQYLELYSNNITGPV

PSDLGNLTNLVSLDLYLNSFTGPI

PDSLGKLFKLRFLRLNNNSLTGPI

PMSLTNIMTLQVLDLSNNRLSGSV

PDNGSFSLFTPISFANNLDLCGPV

TSRFCPGSPPFSPPPP

FIPPPIVPTPGGYSATG

AIAGGVAAGAAL

LFAAPALAFAWW

RRRKPQEFFFDVPAEEDPE

VHLGQLKRFSLRELQVAT

DSFSNKNILGRGGFGKVYKGRLAD

GTLVAVKRLKEERTPGGELQFQ

TEVEMISMAVHRNLLRLRGFCM

TPTERLLVYPYMANGSVASCLR

ERPPSQLPLAWSIRQQIALGSA

RGLSYLHDHCDPKIIHRDVKAA

NILLDEEFEAVVGDFGLARLMD

YKDTHVTTAVRGTIGHIAPEYL

STGKSSEKTDVFGYGIMLLELI

TGQRAFDLARLANDDDVMLLDW

VKGLLKEKKLEMLVDPDLQSNY

TEAEVEQLIQVALLCTQSSPME

RPKMSEVVRMLE

GDGLAEKWDEWQKVEVLRQEVELS

SHPTSDWILDSTDNLHAMELSGPR

*Arabidopsis Thaliana* rks10 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 19)
atcaggggttttaacaatgatggattttctctgatgagggatagttctagg gtttgttttaatctcttgaggataaa ATG GAACGAAGATTAATGATCC

CTTGCTTCTTTTGGTTGATTCTCGTTTTGGATTTGGTTCTCAGAGTCTCG

GGCAACGCCGAAGGTGATGCTCTAAGTGCACTGAAAAACAGTTTAGCCGA

CCCTAATAAGGTGCTTCAAAGTTGGGATGCTACTCTTGTTACTCCATGTA

CATGGTTTCATGTTACTTGCAATAGCGACAATAGTGTTACACGTGTTGAC

CTTGGGAATGCAAATCTATCTGGACAGCTCGTAATGCAACTTGGTCAGCT

TCCAAACTTGCAGTACTTGGAGCTTTATAGCAATAACATTACTGGGACAA

TCCCAGAACAGCTTGGAAATCTGACGGAATTGGTGAGCTTGGATCTTTAC

TTGAACAATTTAAGCGGGCCTATTCCATCAACTCTCGGCCGACTTAAGAA

ACTCCGTTTCTTGCGTCTTAATAACAATAGCTTATCTGGAGAAATTCCAA

GGTCTTTGACTGCTGTCCTGACGCTACAAGTTCTGGATCTCTCAAACAAT

CCTCTCACCGGAGATATTCCTGTTAATGGTTCCTTTTCACTTTTCACTCC

AATCAGTTTTGCCAACACCAAGTTGACTCCCCTTCCTGCATCTCCACCGC

CTCCTATCTCTCCTACACCGCCATCACCTGCAGGGAGTAATAGAATTACT

GGAGCGATTGCGGGAGGAGTTGCTGCAGGTGCTGCACTTCTATTTGCTGT

TCCGGCCATTGCACTAGCTTGGTGGCGAAGGAAAAAGCCGCAGGACCACT

TCTTTGATGTACCAGCTGAAGAGGACCCAGAAGTTCATTTAGGACAACTG

AAGAGGTTTTCATTGCGTGAACTACAAGTTGCTTCGGATAATTTTAGCAA

CAAGAACATATTGGGTAGAGGTGGTTTTGGTAAAGTTTATAAAGGACGGT

TAGCTGATGGTACTTTAGTGGCCGTTAAAAGGCTAAAAGAGGAGCGCACC

CAAGGTGGCGAACTGCAGTTCCAGACAGAGGTTGAGATGATTAGTATGGC

GGTTCACAGAAACTTGCTTCGGCTTCGTGGATTTTGCATGACTCCAACCG

AAAGATTGCTTGTTTATCCCTACATGGCTAATGGAAGTGTTGCCTCCTGT

TTAAGAGAACGTCCCGAGTCCCAGCCACCACTTGATTGGCCAAAGAGACA

GCGTATTGCGTTGGGATCTGCAAGAGGGCTTGCGTATTTACATGATCATT

GCGACCCAAAGATTATTCATCGAGATGTGAAAGCTGCAAATATTTTGTTG

GATGAAGAGTTTGAAGCCGTGGTTGGGGATTTTGGACTTGCAAAACTCAT

GGACTACAAAGACACACATGTGACAACCGCAGTGCGTGGGACAATTGGTC

ATATAGCCCCTGAGTACCTTTCCACTGGAAAATCATCAGAGAAACCGAT

GTCTTTGGGTATGGAGTCATGCTTCTTGAGCTTATCACTGGACAAAGGGC

TTTTGATCTTGCTCGCCTCGCGAATGATGATGATGTCATGTTACTAGACT

GGGTGAAAGGGTTGTTAAAAGAGAAGAAATTGGAAGCACTAGTAGATGTT

GATCTTCAGGGTAATTACAAAGACGAAGAAGTGGAGCAGCTAATCCAAGT

GGCTTTACTCTGCACTCAGAGTTCACCAATGGAAAGACCCAAAATGTCTG

AAGTTGTAAGAATGCTTGAAGGAGATGGTTTAGCTGAGAGATGGGAAGAG

TGGCAAAAGGAGGAAATGTTCAGACAAGATTTCAACTACCCAACCCACCA

TCCAGCCGTGTCTGGCTGGATCATTGGCGATTCCACTTCCCAGATCGAAA

ACGAATACCCCTCGGGTCCAAGA <u>TAA</u> gattcgaaacacgaatgttttt tctgtattttgttttctctgtatttattgagggttttagcttc Predicted Amino Acid Sequence of the *Arabidopsis thaliana* RKS10 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 20)
MERRLMIPCFFWLILVL

DLVLRVSGNAEG

DALSALKNSLADP

NKVLQSWDATLVT

PCTWFHVTCNSDNSVTRV

DLGNANLSGQLV

M QLGQLPNLQYLELYSNNITGTI

PEQLGNLTELVSLDLYLNNLSGPI

PSTLGRLKKLRFLRLNNNSLSGEI

PRSLTAVLTLQVLDLSNNPLIGDI

PVNGSFSLTPISFANTK LT PL

PASPPPPISPTPPSPAGSNRITG

AIAGGVAAGAAL

LFAVPAIALAWW

RRKKPQDHFFDVPAEEDPE

VHLGQLKRFSLRELQVAS

DNFSNKNILGRGGFGKVYKGRLAD

GTLVAVKRLKEERTQGGELQFQ

TEVEMISMAVHRNLLRLRGFCM

TPTERLLVYPYMANGSVASCLR

ERPESQPPLDWPKRQRIALGSA

RGLAYLHDHCDPKIIHRDVKAA

NILLDEEFEAVVGDFGLAKLMD

YKDTHVTTAVRGTIGHIAPEYL

STGKSSEKTDVFGYGVMLLELI

TGQRAFDLARLANDDDVMLLDW

VKGLLKEKKLEALVDVDLQGNY

KDEEVEQLIQVALLCTQSSPME

RPKMSEVVRMLE

GDGLAERWEEWQKEEMFRQDFNYPTHH

PAVSGWIIGDSTSQIENEYPSGPR

*Arabidopsis Thaliana* RKS 11 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 21)
ttgttaacctctcgtaactaaaatcttcc

ATG GTAGTAGTAACAAGAAG

ACCATGAAGATTCAAATTCATCTCCTTTACTCGTTCTTGTTCCTCTGTTT

CTCTACTCTCACTCTATCTTCTGAGCCCAGAAACCCTGAAGTTGAGGCGT

TGATAAGTATAAGGAACAATTTGCATGATCCTCATGGAGCTTTGAACAAT

TGGGACGAGTTTTCAGTTGATCCTTGTAGCTGGGCTATGATCACTTGCTC

TCCCGACAACCTCGTCATTGGACTAGGAGCGCCGAGCCAGTCTCTCTCGG

GAGGTTTATCTGAGTCTATCGGAAATCTCACAAATCTCCGACAAGTGTCA

TTGCAAAATAACAACATCTCCGGCAAAATTCCACCGGAGCTCGGTTTTCT

ACCCAAATTACAAACCTTGGATCTTTCCAACAACCGATTCTCCGGTGACA

TCCCTGTTTCCATCGACCAGCTAAGCAGCCTTCAATATCTGAGACTCAAC

AACAACTCTTTGTCTGGGCCCTTCCCTGCTTCTTTGTCCCAAATTCCTCA

CCTCTCCTTCTTGGACTTGTCTTACAACAATCTCAGTGGCCCTGTTCCTA

AATTCCCAGCAAGGACTTTAAACGTTGCTGGTAATCCTTTGATTTGTAGA

AGCAACCCACCTGAGATTTGTTCTGGATCAATCAATGCAAGTCCACTTTC

TGTTTCTTTGAGCTCTTCATCAGGACGCAGGTCTAATAGATTGGCAATAG

CTCTTAGTGTAAGCCTTGGCTCTGTTGTTATACTAGTCCTTGCTCTCGGG

TCCTTTTGTTGGTACCGAAAGAAACAAAGAAGGCTACTGATCCTTAACTT

AAACGCAGATAAACAAGAGGAAGGGCTTCAAGGACTTGGGAATCTAAGAA

GCTTCACATTCAGAGAACTCCATGTTTATACAGATGGTTTCAGTTCCAAG

AACATTCTCGGCGCTGGTGGATTCGGTAATGTGTACAGAGGCAAGCTTGG

AGATGGGACAATGGTGGCAGTGAAACGGTTGAAGGATATTAATGGAACCT

CAGGGGATTCACAGTTTCGTATGGAGCTAGAGATGATTAGCTTAGCTGTT

CATAAGAATCTGCTTCGGTTAATTGGTTATTGCGCAACTTCTGGTGAAAG

GCTTCTTGTTTACCCTTACATGCCTAATGGAAGCGTCGCCTCTAAGCTTA

AATCTAAACCGGCATTGGACTGGAACATGAGGAAGAGGATAGCAATTGGT

GCAGCGAGAGGTTTGTTGTATCTACATGAGCAATGTGATCCCAAGATCAT

TCATAGAGATGTAAAGGCAGCTAATATTCTCTTAGACGAGTGCTTTGAAG

CTGTTGTTGGTGACTTTGGACTCGCAAAGCTCCTTAACCATGCGGATTCT

CATGTCACAACTGCGGTCCGTGGTACGGTTGGCCACATTGCACCTGAATA

TCTCTCCACTGGTCAGTCTTCTGAGAAAACCGATGTGTTTGGGTTCGGTA

TACTATTGCTCGAGCTCATAACCGGACTGAGAGCTCTTGAGTTTGGTAAA

ACCGTTAGCCAGAAAGGAGCTATGCTTGAATGGGTGAGGAAATTACATGA

AGAGATGAAAGTAGAGGAACTATTGGATCGAGAACTCGGAACTAACTACG

ATAAGATTGAAGTTGGAGAGATGTTGCAAGTGGCTTTGCTATGCACACAA

TATCTGCCAGCTCATCGTCCTAAAATGTCTGAAGTTGTTTTGATGCTTGA

AGGCGATGGATTAGCCGAGAGATGGGCTGCTTCGCATAACCATTCACATT

TCTACCATGCCAATATCTCTTTCAAGACAATCTCTTCTCTGTCTACTACT

TCTGTCTCAAGGCTTGACGCACATTGCAATGATCCAACTTATCAAATGTT

TGGATCTTCGGCTTTCGATGATGACGATGATCATCAGCCTTTAGATTCCT

TTGCCATGGAACTATCCGGTCCAAGA <u>TAA</u> cacaatgaaagaaagatat catttttacgatggatcaaacaatccaatgaaaaaa Predicted Amino Acid Sequence of the *Arabidopsis thaliana* RKS11 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 22)
```
MVVVTKKTMKIQIHLLYSFLFL
CFSTLTLSSEPRNPEV
EALISIRNNLHDP
HGALNNWDEFSVD
PCSWAMITCSPDNLVIGL
GAPSQSLSGGLS
ESIGNLTNLRQVSLQNNNISGKI
PPELGFLPKLQTLDLSNNRFSGDI
PVSIDQLSSLQYLRLNNNSLSGPF
PASLSQIPHLSFLDLSYNNLSGPV
PKFPARTFNVAGNPLICRSN
PPEICSGSINASPL
SVSLSSSSGRRSNR
LAIALSVSLGSVVIL
VLALGSFCWY
RKKQRRLLILNLNGADKQEE
GLQGLGNLRSFTFRELHVYT
DGFSSKNILGAGGFGNVYRGKLGD
GTMVAVKRLKDINGTSGDSQFR
MELEMISLAVHKNLLRLIGYCA
TSGERLLVYPYMPNGSVASKLK
SKPALDWNMRKRIAIGAA
RGLLYLHEQCDPKIIHRDVKAA
NILLDECFEAVVGDFGLAKLLN
HADSHVTTAVRGTVGHIAPEYL
STGQSSEKTDVFGFGILLLELI
TGLRALEFGKTVSQKGAMLEW
VRKLHEEMKVEELLDRELGTNY
DKIEVGEMLQVALLCTQYLPAH
RPKMSEVVLMLE
GDGLAERWAASHNHSHFYHANI
SFKTISSLSTTSVSRLDAHCNDPTYQMFG
SSAFDDDDDHQPLDSFAMELSGPR
```

*Arabidopsis Thaliana* RKS12 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 23)
```
tttaaaaaccttgctagttctcaattctcatgactttgcttttagtcttag
aagtggaaa ATG GAACATGGATCATCCCGTGGCTTTATTTGGCTGATTC
TATTTCTCGATTTTGTTTCCAGAGTCACCGGAAAAACACAAGTTGATGCT
CTCATTGCTCTAAGAAGCAGTTTATCATCAGGTGACCATACAAACAATAT
ACTCCAAAGCTGGAATGCCACTCACGTTACTCCATGTTCATGGTTTCATG
TTACTTGCAATACTGAAAACAGTGTTACTCGTCTTGACCTGGGGAGTGCT
AATCTATCTGGAGAACTGGTGCCACAGCTTGCTCAGCTTCCAAATTTGCA
GTACTTGGAACTTTTTAACAATAATATTACTGGGGAGATACCTGAGGAGC
TTGGCGACTTGATGGAACTAGTAAGCTTGGACCTTTTTGCAAACAACATA
AGCGGTCCCATCCCTTCCTCTCTTGGCAAACTAGGAAAACTCCGCTTCTT
GCGTCTTTATAACAACAGCTTATCTGGAGAAATTCCAAGGTCTTTGACTG
CTCTGCCGCTGGATGTTCTTGATATCTCAAACAATCGGCTCAGTGGAGAT
ATTCCTGTTAATGGTTCCTTTTCGCAGTTCACTTCTATGAGTTTTGCCAA
TAATAAATTAAGGCCGCGACCTGCATCTCCTTCACCATCACCTTCAGGAA
CGTCTGCAGCAATAGTAGTGGGAGTTGCTGCGGGTGCAGCACTTCTATTT
GCGCTTGCTTGGTGGCTGAGAAGAAAACTGCAGGGTCACTTTCTTGATGT
ACCTGCTGAAGAAGACCCAGAGGTTTATTTAGGACAATTTAAAAGGTTCT
CCTTGCGTGAACTGCTAGTTGCTACAGAGAAATTTAGCAAAAGAAATGTA
TTGGGCAAAGGACGTTTTGGTATATTGTATAAAGGACGTTTAGCTGATGA
CACTCTAGTGGCTGTGAAACGGCTAAATGAAGAACGTACCAAGGGTGGGG
AACTGCAGTTTCAAACCGAAGTTGAGATGATCAGTATGGCCGTTCATAGG
AACTTGCTTCGGCTTCGTGGCTTTTGCATGACTCCAACTGAAAGATTACT
TGTTTATCCCTACATGGCTAATGGAAGTGTTGCTTCTTGTTTAAGAGAGC
GTCCTGAAGGCAATCCAGCCCTTGACTGGCCAAAAGAAAGCATATTGCT
CTGGGATCAGCAAGGGGGCTCGCATATTTACACGATCATTGCGACCAAAA
GATCATTCACCTGGATGTGAAAGCTGCAAATATACTGTTAGATGAAGAGT
TTGAAGCTGTTGTTGGAGATTTTGGGCTAGCAAAATTAATGAATTATAAC
GACTCCCATGTGACAACTGCTGTACGGGTACGATTGGCCATATAGCGCC
CGAGTACCTCTCGACAGGAAATCTTCTGAGAAGACTGATGTTTTTGGGT
ACGGGGTCATGCTTCTCGAGCTCATCACTGGACAAAAGGCTTTCGATCTT
GCTCGGCTTGCAAATGATGATGATATCATGTTACTCGACTGGGTGAAAGA
GGTTTTGAAAGAGAAGAAGTTGGAAAGCCTTGTGGATGCAGAACTCGAAG
```

```
GAAAGTACGTGGAAACAGAAGTGGAGCAGCTGATACAAATGGCTCTGCTC

TGCACTCAAAGTTCTGCAATGGAACGTCCAAAGATGTCAGAAGTAGTGAG

AATGCTGGAAGGAGATGGTTTAGCTGAGAGATGGGAAGAATGGCAAAAGG

AGGAGATGCCAATACATGATTTTAACTATCAAGCCTATCCTCATGCTGGC

ACTGACTGGCTCATCCCCTATTCCAATTCCCTTATCGAAAACGATTACCC

CTCGGGGCCAAGA TAA ccttttagaaagggtcatttcttgtgggttctt caacaagtatatataggtagtgaagttgtaagaagcaaaaccccacatt cacctttgaatatcactactctataa
```

Predicted Amino Acid Sequence of the *Arabidopsis thaliana* RKS12 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif containing 2 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
                                        (SEQ ID NO: 24)
MEHGSSRGFI

WLILFLDFVSRVTGKTQV

DALIALRSSLSSGDHTNNILQ

SWNATHVT

PCSWFHVTCNTENSVTRL

DLGSANLSGELV

P QLAQLPNLQYLELFNNNITGEI

PEELGDLMELVSLDLFANNISGPI

PSSLGKLGKLRFLRLYNNSLSGEI

PRSLTALP LDVLDISNNRLSGDI

PVNGSFSQFTSMRFA NNKLRPR

PASPSPSPSGGTS

AAIVVGVAAGAALLFALAWWL

RRKLQGHFLDVPAAEEDPE

VYLGQFKRFSLRELLVAT

EKFSKRNVLGKGRFGILYKGRLAD

DTLVAVKRLNEERTKGGELQFQ

TEVEMISMAVHRNLLRLRGFCM

TPTERLLVYPYMANGSVASCLR

ERPEGNPALDWPKRKHIALGSA

RGLAYLHDHCDQKIIHLDVKAA

NILLDEEFEAVVGDFGLAKLMN

YNDSHVTTAVRGTIGHIAPEYL

STGKSSEKTDVFGYGVMLLELI

TGQKAFDLARLANDDDIMLLDW

VKEVLKEKKLESLVDAELEGKY

VETEVEQLIQMALLCTQSSAME

RPKMSEVVRMLE

GDGLAERWEEWQKEEMPIHDFNYQAY

PHAGTDWLIPYSNSLIENDYPSGPR
```

*Arabidopsis Thaliana* RKS13 cDNA

The start codons encoding predicted the methionine residue of the gene product has been indicated by bold capitals.

The first stopcodon has been underlined.

Nucleotides predicted to encode protein sequences are in capitals. Leader and trailer sequences are in lowercase letters.

```
                                       (SEQ ID NO: 25)
taataaacctctaataataatggctttgcttttactctgatgacaagttca aaa ATG GAACAAAGATCACTCCTTTGCTTCCTTTATCTGCTCCTACTAT

TCAATTTCACTCTCAGAGTCGCTGGAAACGCTGAAGGTGATGCTTTGACT

CAGCTGAAAAACAGTTTGTCATCAGGTGACCCTGCAAACAATGTACTCCA

AAGCTGGGATGCTACTCTTGTTACTCCATGTACTTGGTTTCATGTTACTT

GCAATCCTGAGAATAAAGTTACTCGTGTTGACCTTGGGAATGCAAAACTA

TCTGGAAAGTTGGTTCCAGAACTTGGTCAGCTTTTAAACTTGCAGTACTT

GGAGCTTTATAGCAATAACATTACAGGGGAGATACCTGAGGAGCTTGGCG

ACTTGGTGGAACTAGTAAGCTTGGATCTTTACGCAAACAGCATAAGCGGT

CCCATCCCTTCGTCTCTTGGCAAACTAGGAAAACTCCGGTTCTTGCGTCT

TAACAACAATAGCTTATCAGGGGAAATTCCAATGACTTTGACTTCTGTGC

AGCTGCAAGTTCTGGATATCTCAAACAATCGGCTCAGTGGAGATATTCCT

GTTATGGTTCTTTTTCGCTCTTCACTCCTATCAGTTTTGCGAATAATAG

CTTAACGGATCTTCCCGAACCTCCGCCTACTTCTACCTCTCCTACGCCAC

CACCACCTTCAGGGGGGCAAATGACTGCAGCAATAGCAGGGGGAGTTGCT

GCAGGTGCAGCACTTCTATTTGCTGTTCCAGCCATTGCGTTTGCTTGGTG

GCTCAGAAGAAACCACAGGACCACTTTTTTGATGTACCTGCTGAAGAAG

ACCCAGAGGTTCATTTAGGACAACTCAAAAGGTTTACCTTGCGTGAACTG

TTAGTTGCTACTGATAACTTTAGCAATAAAAATGTATTGGGTAGAGGTGG

TTTTGGTAAAGTGTATAAAGGACGTTTAGCCGATGGCAATCTAGTGGCTG

TCAAAAGGCTAAAAGAAGAACGTACCAAGGGTGGGGAACTGCAGTTTCAA
```

-continued

```
ACCGAAGTTGAGATGATCAGTATGGCCGTTCATAGGAACTTGCTTCGGCT

TCGTGGCTTTTGCATGACTCCAACTGAAAGATTACTTGTTTATCCCTACA

TGGCTAATGGAAGTGTTGCTTCTTGTTTAAGAGAGCGTCCTGAAGGCAAT

CCAGCACTTGATTGGCCAAAAAGAAAGCATATTGCTCTGGGATCAGCAAG

GGGGCTTGCGTATTTACATGATCATTGCGACCAAAAAATCATTCACCGGG

ATGTTAAAGCTGCTAATATATTGTTAGATGAAGAGTTTGAAGCTGTTGTT

GGAGATTTTGGGCTCGCAAAATTAATGAATTATAATGACTCCCATGTGAC

AACTGCTGTACGCGGTACAATTGGCCATATAGCGCCCGAGTACCTCTCGA

CAGGAAAATCTTCTGAGAAGACTGATGTTTTTGGGTACGGGGTCATGCTT

CTCGAGCTCATCACTGGACAAAAGGCTTTCGATCTTGCTCGGCTTGCAAA

TGATGATGATATCATGTTACTCGACTGGGTGAAAGAGGTTTTGAAAGAGA

AGAAGTTGGAAAGCCTTGTGGATGCAGAACTCGAAGGAAAGTACGTGGAA

ACAGAAGTGGAGCAGCTGATACAAATGGCTCTGCTCTGCACTCAAAGTTC

TGCAATGGAACGTCCAAAGATGTCAGAAGTAGTGAGAATGCTGGAAGGAG

ATGGTTTAGCTGAGAGATGGGAAGAATGGCAAAAGGAGGAGATGCCAATA

CATGATTTTAACTATCAAGCCTATCCTCATGCTGGCACTGACTGGCTCAT

CCCCTATTCCAATTCCCTTATCGAAAACGATTACCCCTCGGGTCCAAGA T

AA cctttagaaagggtcttttcttgtgggttcttcaacaagtatatata tagattggtgaagttttaagatgcaaaaaaaa
```

Predicted Amino Acid Sequence of the *Arabidopsis thaliana* RKS13 Protein.

Different domains are spaced and shown from the N-terminus towards the C-terminus. Overall domain structure is similar as described in Schmidt et al. (1997).

At the predicted extracellular domain the first domain represents a signal sequence. The second domain contains leucine zipper motifs, containing 2 times 2 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 26)

```
MEQRSLLCFLYLL

LLFNFTLRVAGNAEG

DALTQLKNSLSSGDP

ANNVLQSWDATLVT

PCTWFHVTCNPENKVTRV

DLGNAKLSGKLV

P ELGQLLNLQYLELYSNNITGEI

PEELGDLVELVSLDLYANSISGPI

PSSLGKLGKLRFLRLNNNSLSGEI

PMTLTSVQLQV LDISNNRLSGDI

PVNGSFSLFTPISFANNSLTDLPE

PPPTSTSPTPPPPSG

GQMTAAIAGGVAAGAAL

LFAVPAIAFAWWL

RRKPQDHFFDVPGAEEDPE

VHLGQLKRFTLRELLVAT

DNFSNKNVLGRGGFGKVYKGRLAD

GNLVAVKRLKEERTKGGELQFQ

TEVEMISMAVHRNLLRLRGFCM

TPTERLLVYPYMANGSVASCLR

ERPEGNPALDWPKRKHIALGSA

RGLAYLHDHCDQKIIHRDVKAA

NILLDEEFEAVVGDFGLAKLMN

YNDSHVTTAVRGTIGHIAPEYL

STGKSSEKTDVFGYGVMLLELI

TGQKAFDLARLANDDDIMLLDW

VKEVLKEKKLESLVDAELEGKY

VETEVEQLIQMALLCTQSSAME

RPKMSEVVRMLE

GDGLAERWEEWQKEEMPIHDFNYQA

YPHAGTDWLIPYSNSLIENDYPSGPR
```

*Arabidopsis Thaliana* RKS14 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 27)

```
ctgcacctagagattaatactctcaagaaaaacaagttttgattcggaca aag ATG TTGCAAGGAAGAAGAGAAGCAAAAAGAGTTATGCTTTGTTCT

CTTCAACTTTCTTCTTCTTCTTTATCTGTTTTCTTTCTTCTTCTTCTGCA

GAACTCACAGACAAAGTTGTTGCCTTAATAGGAATCAAAAGCTCACTGAC

TGATCCTCATGGAGTTCTAATGAATTGGGATGACACAGCAGTTGATCCAT

GTAGCTGGAACATGATCACTTGTTCTGATGGTTTTGTCATAAGGCTAGAA

GCTCCAAGCCAAAACTTATCAGGAACTCTTTCATCAAGTATTGGAAATTT

AACAAATCTTCAAACTGTATACAGGTTATTGCAGAACAATTACATAACAG
```

-continued

```
GAAACATCCCTCATGAGATTGGGAAATTGATGAAACTCAAAACACTTGAT

CTCTCTACCAATAACTTCACTGGTCAAATCCCATTCACTCTTTCTTACTC

CAAAAATCTTCACAGGAGGGTTAATAATAACAGCCTGACAGGAACAATTC

CTAGCTCATTGGCAAACATGACCCAACTCACTTTTTTGGATTTGTCGTAT

AATAACTTGAGTGGACCAGTTCCAAGATCACTTGCCAAAACATTCAATGT

TATGGGCAATTCTCAGATTTGTCCAACAGGAACTGAGAAAGACTGTAATG

GGACTCAGCCTAAGCCAATGTCAATCACCTTGAACAGTTCTCAAAGAACT

AAAAACCGGAAAATCGCGGTAGTCTTCGGTGTAAGCTTGACATGTGTTTG

CTTGTTGATCATTGGCTTTGGTTTTCTTCTTTGGTGGAGAAGAAGACATA

ACAAACAAGTATTATTCTTTGACATTAATGAGCAAAACAAGGAAGAAATG

TGTCTAGGGAATCTAAGGAGGTTTAATTTCAAAGAACTTCAATCCGCAAC

TAGTAACTTCAGCAGCAAGAATCTGGTCGGAAAAGGAGGGTTTGGAAATG

TGTATAAAGGTTGTCTTCATGATGGAAGTATCATCGCGGTGAAGAGATTA

AAGGATATAAACAATGGTGGTGGAGAGGTTCAGTTTCAGACAGAGCTTGA

AATGATAAGCCTTGCCGTCCACCGGAATCTCCTCCGCTTATACGGTTTCT

GTACTACTTCCTCTGAACGGCTTCTCGTTTATCCTTACATGTCCAATGGC

AGTGTCGCTTCTCGTCTCAAAGCTAAACCGGTATTGGATTGGGGCACAAG

AAAGCGAATAGCATTAGGAGCAGGAAGAGGGTTGCTGTATTTGCATGAGC

AATGTGATCCAAAGATCATTCACCGTGATGTCAAAGCTGCGAACATACTT

CTTGACGATTACTTTGAAGCTGTTGTCGGAGATTTCGGGTTGGCTAAGCT

TTTGGATCATGAGGAGTCGCATGTGACAACCGCCGTGAGAGGAACAGTGG

GTCACATTGCACCTGAGTATCTCTCAACAGGACAATCTTCTGAGAAGACA

GATGTGTTCGGTTTCGGGATTCTTCTTCTCGAATTGATTACTGGATTGAG

AGCTCTTGAATTCGGAAAAGCAGCAAACCAAAGAGGAGCGATACTTGATT

GGGTAAAGAAACTACAACAAGAGAAGAAGCTAGAACAGATAGTAGACAAG

GATTTGAAGAGCAACTACGATAGAATAGAAGTGGAAGAAATGGTTCAAGT

GGCTTTGCTTTGTACACAGTATCTTCCCATTCACCGTCCTAAGATGTCTG

AAGTTGTGAGAATGCTTGAAGGCGATGGTCTTGTTGAGAAATGGGAAGCT

TCTTCTCAGAGAGCAGAAACCAATAGAAGTTACAGTAAACCTAACGAGTT

TTCTTCCTCTGAACGTTATTCGGATCTTACAGATGATTCCTCGGTGCTGG

TTCAAGCCATGGAGTTATCAGGTCCAAGA TGA caagagaaactatatga atggctttgggtttgtaaaaaa
```

Predicted Amino Acid Sequence of the *Arabidopsis Thaliana* RKS14 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 28)

```
MLQGRREAKKSYALFSSTFF

FFFICFLSSSSAELTDKV

VALIGIKSSLTDP

HGVLMNWDDTAVD

PCSWNMITCSDGFVIR

LEAPSQNLSGTLSS

SIGNLTNLQTVYRLLQNNYITGNI

PHEIGKLMKLKTLDLSTNNFTGQI

PFTLSYSKNLHRRV NNNSLTGTI

PSSLANMTQLTFLDLSYNNLSGPV

PRSLAKTFNVMGNSQICPT

GTEKDCNGTQPKPMSITLNSSQR

TKNRK

IAVVFGVSLTCVCLLIIGFGFLLWW

RRRHNKQVLFFDINEQNKE

EMCLGNLRRFNFKELQSAT

SNFSSKNLVGKGGFGNVYKGCLHD

GSIIAVKRLKDINNGGGEVQFQ

TELEMISLAVHRNLLRLYGFCT

TSSERLLVYPYMSNGSVA

SRLKAKPVLDWGTRKRIALGAG

RGLLYLHEQCDPKIIHRDVKAA

NILLDDYFEAVVGDFGLAKLLD

HEESHVTTAVRGTVGHIAPEYL

STGQSSEKTDVFGFGILLLELI

TGLRALEFGKAANQRGAILDW

VKKLQQEKKLEQIVDKDLKSNY

DRIEVEEMVQVALLCTQYLPIH

RPKMSEVVRMLE

GDGLVEKWEASSQRAET

NRSYSKPNEFSSS

ERYSDLTDDSSVLVQAMELSGPR
```

Most of these receptors and their respective coding sequences have been isolated from *Arabidopsis*. However, orthologous receptors from other plants and the coding sequences for these receptors, which have not yet been isolated, can be used as well. It is believed that these coding sequences will be homologous to the sequences disclosed in the above mentioned references. Thus, in principle any nucleotide sequence, which is homologous to said sequences and which codes for a protein that at least functions as a systemic signal compound receptor would be useful. These nucleotide sequences can be isolated from plants expressing orthologous receptors, however, these nucleotide sequences can also be made by modifying existing nucleotide sequences, which then would code for muteins of the already known receptors.

Muteins of the receptors of the invention are proteins that are obtained from the already known receptors by replacing, adding and/or deleting one or more amino acids, while still retaining their function as receptor for systemic signalling compounds. Such muteins can readily be made by protein engineering, e.g. by changing the open reading frame capable of encoding the protein so that the amino acid sequence is thereby affected. As long as the changes in the amino acid sequences do not altogether abolish the activity of the protein such muteins are embraced in the present invention. Further, it should be understood that muteins should be derivable from the known receptors while retaining biological activity, i.e. all, or a great part of the intermediates between the mutein and the protein depicted in the sequence listing should be capable of being induced by systemic signalling compounds. A great part would mean 30% or more of the intermediates, preferably 40% of more, more preferably 50% or more, more preferably 60% or more, more preferably 70% or more, more preferably 80% or more, more preferably 90% or more, more preferably 95% or more, more preferably 99% or more.

Thus, also part of the invention are receptors which are at least 70% identical to known proteins, but more preferably more than 80% identical, more preferably more than 90% identical and most preferably inure than 95% identical to the above discussed known receptors. For calculation of percentage identity the BLAST algorithm can be used (Nucl. Acids Res., 1997, 25, 3389.3402) using default parameters or, alternatively, the GAP algorithm (J. Mol. Biol., 1970, 48, 443-453), using default parameters, which both are included in the Wisconsin Genetics Software Package, Genetics Computer Group (GCG), 575 Science, Madison, Wis., USA. BLAST searches assume that proteins can be modelled as random sequences. However, many real proteins comprise regions of non-random sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Comput. Chem., 1993, 17, 149-163) and XNU (Comput. Chem., 1993, 17, 191-201) low-complexity filters can be employed alone or in combination.

As used herein, 'sequence identity' or 'identity' or 'homology' in the context of two protein sequences (or nucleotide sequences) includes reference to the residues in the two sequences which are the same when aligned for maximum correspondence over a specified comparison window.

When percentage of sequence identity is used in reference to proteins it is recognised that residue positions which are not identical often differ by conservative amino acid substitutions, where amino acids are substituted for other amino acid residues with similar chemical properties (e.g. charge or hydrophobicity) and therefore do not change the functional properties of the molecule. Where sequences differ in conservative substitutions, the percentage sequence identity may be adjusted upwards to correct for the conservative nature of the substitutions. Sequences, which differ by such conservative substitutions are said to have 'sequence similarity' or 'similarity'. Means for making these adjustments are well known to persons skilled in the art. Typically this involves scoring a conservative substitution as a partial rather than a full mismatch, thereby increasing the percentage sequence identity. Thus, for example, where an identical amino acid is given a score of 1 and a non-conservative substitution is give a score of zero, a conservative substitution is given a score between 0 and 1. The scoring of conservative substitutions is calculated, e.g. according to the algorithm of Meyers and Miller (Computer Applic. Biol. Sci., 1998, 4, 11-17).

As used herein, 'percentage of sequence identity' means the value determined by comparing two optimally aligned sequences over a comparison window, wherein the portion of the amino acid sequence or nucleotide sequence in the comparison window may comprise additions or deletions (i.e., gaps) as compared to the reference sequence for optimal alignment of the two sequences. The percentage is calculated by determining the number of positions at which the identical amino acid or nucleic acid base residue occurs in both sequences to yield the number of matched positions, dividing the number of matched positions by the total number of positions in the window of comparison and multiplying the result by 100 to yield the percentage of sequence identity.

In general not all amino acids of a protein and not all nucleotides of a nucleotide sequence are equally well interchangeable. In most case proteins have one or more regions which are important or crucial for the function. For the RKS receptors of the invention it is easy to determine the less variable regions by aligning the sequences (which can be found in WO 04/007712, on pages 45, and 52-93 (which corresponds to Table 2 on page 20, and paragraphs [0056] to [0140], respectively, of US patent publication 20060265783), which are herein incorporated by reference. See above.) and determining so-called consensus sequences, i.e. parts of the protein which are well conserved between homologous sequences with the same function. When trying to design variants (or muteins) of the RKS receptors, these consensus sequences should preferably be kept intact, while other regions may be varied more. In the group of RKS receptors the most preferred are RKS1, RKS4, RKS7, RKS11 and RKS14. This subgroup shares specific consensus sequences.

Very important is to mention that partial receptors, e.g. only (parts of the) extracellular domain or only intracellular domain or fragments thereof are able to act as constitutive active compounds in the heterodimer receptor protein complex. Our results indicate that the N-terminal part of RKS4 (the extracellular domain) might act as a constitutive activator of the brassinosteroid response with respect to resistance (FIG. 5) and possibly also plant fitness as illustrated by the increase in organ size and fresh weight (FIGS. 7 and 8).

When, in the present invention the N-terminal part of an RKS receptor is mentioned, the extracellular domain of said RKS receptor is meant. A person skilled in the art will understand what part of the receptor is meant by the extracellular domain. Besides, in WO 04/007712 (page 1, lines 9-35, and pages 52-93 of WO 04/007712 (which corresponds to paragraph [0001] and paragraphs [0056] to [0140], respectively, of US patent publication 20060265783) are herein incorporated by reference. See above.) the extracellular domains of the RKS receptors have been indicated.

A further embodiment of the invention is formed by chimaeric receptors, in which the ligand binding part of the above mentioned receptors is replaced by a ligand binding part of another receptor, such as a different signal compound recognising receptor or e.g. a steroid receptor. In this way it is possible to induce different IR pathways, which are triggered by different receptors, as discussed above, by one and the same signal molecule or ligand. This also enables the use of cheaper and more readily available compounds for the induction of the IR response. One example, for instance is to replace the ligand binding part of the RKS receptor with the SA-binding part of the salicyclic acid receptor. After transformation of plants with both the native salicylic acid receptor and the chimaeric RKS receptor application of salicylic acid would trigger both the salicylic acid induced response and the brassinosteroid-induced response. It is, however, also possible to use ligand-binding parts of receptors and ligands, which are not involved in pathogen resistance. It would, for instance be possible to replace the ligand-binding part of any of the above mentioned receptors by the ligand-binding part of another not-related LRR-receptor kinase like ERECTA (Plant Cell, 1996, 8, 735-746).

The nucleotide sequences will need to be expressed in the plant(s) into which they are transformed. For this a genetic construct (expression cassette) that comprises an expressible nucleotide sequence is needed. The expression of the nucleotide sequence depends on the operational elements contained in such a construct, such as a promoter, a terminator, and enhancing elements.

The term "promoter" is intended to mean a short DNA sequence to which RNA polymerase and/or other transcription initiation factors bind prior to transcription of the DNA to which the promoter is functionally connected, allowing transcription to take place. The promoter is usually situated upstream (5') of the coding sequence. In its broader scope, the term "promoter" includes the RNA polymerase binding site as well as regulatory sequence elements located within several hundreds of base pairs, occasionally even further away, from the transcription start site. Such regulatory sequences are, e.g. sequences that are involved in the binding of protein factors that control the effectiveness of transcription initiation in response to physiological conditions. The promoter region should be functional in the host cell and preferably corresponds to the natural promoter region of the receptor protein. However, any heterologous promoter region can be used as long as it is functional in the host cell where expression is desired. The heterologous promoter can be either constitutive, tissue or developmental specific or regulable. A constitutive promoter such as the CaMV 35S promoter or T-DNA promoters, all well known to those skilled in the art, are promoters, which are subjected to substantially no regulation such as induction or repression, but which allows for a steady and substantially unchanged transcription of the DNA sequence to which it is functionally bound in all or most of the active cells of the organism provided that other requirements for the transcription to take place are fulfilled. A tissue-specific promoter is a promoter, which restricts the expression of the coding sequence to a limited part of the plant, i.e. a special tissue and/or a special cell type. An often used tissue-specific promoter is the Rubisco promoter (which is specific for green parts of the plants). A regulable or inducible promoter is a promoter of which the function is regulated by one or more factors, either internally present or externally added (Trends in biotechnology 2005, 23, 283-290). In the absence of an inducer, the DNA sequence will either not be transcribed or will be transcribed at a reduced level relative to transcription levels in the presence of an inducer. In certain instances, a factor may bind specifically to an inducible promoter to activate transcription, said factor being present in an inactive form and convertible (either directly or indirectly) to an active form by the inducer. The inducer may be a chemical/biochemical agent, such as a protein, metabolite (sugar, alcohol, etc.) a growth regulator, a herbicide, or a phenolic compound. Alternatively, the inducer may be a directly imposed physiological stress (for example, heat, salt, wounding, toxic elements, etc.) or an indirectly imposed physiological stress (for example, the action of a pathogen or disease agent, such as a virus). A plant cell containing an inducible promoter may be exposed to an inducer by external application of the inducer to the cell such as by spraying, watering, heating, or similar methods. Examples of inducible promoters include the inducible 70 kD heat shock promoter of Drosophila melanogaster (Ann. Rev. Genet., 1985, 19, 297-323) and the alcohol dehydrogenase promoter which is induced by ethanol (Nagao, R. T. et al., in: Miflin, B. J. (ed.) Oxford Surveys of Plant Molecular and Cell Biology, Vol. 3., pp. 384-438, Oxford Univ. Press, 1986). Examples of promoters that are inducible by a simple chemical are described in Gurr and Rushton (Trends in biotechnology 2005, 23, 283-290), WO 90/08826, WO 93/21334, WO 93/031294 and WO 96/37609.

A terminator is a short piece of DNA that serves to terminate the transcription of the DNA into RNA and is preferably selected from the group consisting of plant transcription terminator sequences, bacterial transcription terminator sequences and plant virus terminator sequences known to those skilled in the art.

Enhancing elements (such as the 35S enhancer) and other elements like scaffold attachment regions (SARs) can be used to increase expression of the genes of the invention. It is also possible to boost expression by introducing an intron (e.g. the Adh-intron) in the open reading frame or to use viral enhancer sequences.

The term "gene" is used to indicate a DNA sequence, which is involved in producing a polypeptide chain and which includes regions preceding and following the coding region (5'-upstream and 3'-downstream sequences) as well as intervening sequences, the so-called introns, which are placed between individual coding segments (so-called exons) or in the 5'-upstream or 3'-downstream region. The 5'-upstream region may comprise a regulatory sequence that controls the expression of the gene, typically a promoter. The 3'-downstream region may comprise sequences, which are involved in termination of transcription of the gene and optionally sequences responsible for polyadenylation of the transcript and the 3' untranslated region.

In eukaryotic cells, an expression cassette usually further comprises a transcriptional termination region located downstream of the open reading frame, allowing transcription to terminate and polyadenylation of the primary transcript to occur. In addition, the codon usage may be adapted to accepted codon usage of the host of choice. The principles governing the expression of a DNA construct in a chosen host cell are commonly understood by those of ordinary skill in the art and the construction of expressible DNA constructs is now routine for any sort of host cell, be it prokaryotic or eukaryotic.

In order for the open reading frame to be maintained in a host cell it will usually be provided in the form of a replicon comprising said open reading frame according to the invention linked to DNA, which is recognised and replicated by the chosen host cell. Accordingly, the selection of the replicon is determined largely by the host cell of choice. Such principles as govern the selection of suitable replicons for a particular chosen host are well within the realm of the ordinary skilled person in the art.

A special type of replicon is one capable of transferring itself, or a part thereof, to another host cell, such as a plant cell, thereby co-transferring the open reading frame according to the invention to said plant cell. Replicons with such capability are herein referred to as vectors. An example of such vector is a Ti-plasmid vector, which, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer DNA sequences into plant cells, or protoplasts, from which new plants may be generated which stably incorporate said DNA in their genomes. A particularly preferred form of Ti-plasmid vectors are the so-called binary vectors (as claimed in EP 0 120 516 B1 and U.S. Pat. No. 4,940,838). Other suitable vectors, which may be used to introduce DNA according to the invention into a plant host, may be selected from the viral vectors, e.g. non-integrative plant viral vectors, such as derivable from the double stranded plant viruses (e.g. CaMV) and single stranded viruses, Gemini viruses and the like. The use of such vectors may be advantageous, particularly when it is difficult to stably transform the plant host. Such may be the case with woody species, especially trees and vines.

The expression "host cells incorporating a DNA sequence according to the invention in their genome" shall mean to comprise cells, as well as multicellular organisms comprising such cells, or essentially consisting of such cells, which stably incorporate said DNA into their genome thereby maintaining the DNA, and preferably transmitting a copy of such DNA to progeny cells, be it through mitosis or meiosis. According to a preferred embodiment of the invention plants are provided, which essentially consist of cells that incorporate one or more copies of said DNA into their genome, and which are capable of transmitting a copy or copies to their progeny, preferably in a Mendelian fashion. By virtue of the transcription and translation of the DNA according to the invention in some or all of the plant's cells, those cells that are capable of producing the receptor(s) for the systemic signal compounds will show an enhanced resistance to pathogen infections.

Transformation of plant species is now routine for an impressive number of plant species, including both the Dicotyledonous as well as the Monocotyledonous. In principle any transformation method may be used to introduce chimeric DNA according to the invention into a suitable ancestor cell, as long as the cells are capable of being regenerated into whole plants. Methods may suitably be selected from the calcium/polyethylene glycol method for protoplasts (Nature, 1982, 296, 72-74; Plant Mol. Biol., 1987, 8, 363-373), electroporation of protoplasts (Bio/Technol., 1985, 3, 1099-1102), microinjection into plant material (Mol. Gen. Genet., 1986, 202, 179-185), (DNA or RNA-coated) particle bombardment of various plant material (Nature, 1987, 327, 70), infection with (non-integrative) viruses and the like. A preferred method according to the invention comprises *Agrobacterium*-mediated DNA transfer. Especially preferred is the use of the so-called binary vector technology as disclosed in EP A 120 516 and U.S. Pat. No. 4,940,838.

Transformation can be facilitated by the use of selectable or screenable markers to discriminate between transformed plants or plant cells and non-transformed plants or plant cells. However, possibly so-called marker-free transformation protocols, such as for instance described in WO 01/29240, can be used.

Generally, after transformation plant cells or cell groupings are selected for the presence of one or more markers which are encoded by plant expressible genes co-transferred with the nucleic acid sequence according to the invention, where after the transformed material is regenerated into a whole plant. Genes which can be used as marker genes can be roughly divided in antibiotic resistance marker genes, such as nptII (giving resistance to kanamycin) and hpt (giving resistance to phosphonotricin), and developmental or metabolic selection marker genes, such as the trehalase gene, the mannose gene (both metabolic markers) and the IPT gene or the RKS receptor kinase genes (developmental markers). For marker-free transformation it is possible to use the previously described T/R system based on transient activity of regenerating gene products WO9743427, or stable integration of inducible regenerating gene products.

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or electroporation (Shimamoto, et al, 1989, Nature 338, 274-276). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Plant Cell, 1990, 2, 603-618). The introduction of genetic material into aleurone protoplasts of other monocot crops such as wheat and barley has been reported (Plant Mol. Biol., 1989, 13, 21-30). Wheat plants have been regenerated from embryogenic suspension culture by selecting only the aged compact and nodular embryogenic callus tissues for the establishment of the embryogenic suspension cultures (Bio/Technol., 1990, 8, 429-434). The combination with transformation systems for these crops enables the application of the present invention to monocots.

Monocotyledonous plants, including commercially important crops such as rice and corn are also amenable to DNA transfer by *Agrobacterium strains* (vide WO 94/00977; EP 0 159 418 B1; Plant. Physiol., 1991, 95, 426-434; The Plant J., 1994, 6, 271-282).

Following DNA transfer and regeneration, putatively transformed plants may be evaluated, for instance using Southern analysis, for the presence of the DNA according to the invention, copy number and/or genomic organization. After the initial analysis, transformed plants showing the desired copy number and expression level of the newly introduced DNA according to the invention may be tested for resistance levels against a pathogen.

Other evaluations may include the testing of pathogen resistance under field conditions, checking fertility, yield, and other characteristics. Such testing is now routinely performed by persons having ordinary skill in the art.

Following such evaluations, the transformed plants may be grown directly, but usually they may be used as parental lines in the breeding of new (inbred) varieties or in the creation of hybrids and the like.

These plants, including plant varieties, with improved resistance against pathogens may be grown in the field, in the greenhouse, or at home or elsewhere. Plants or edible parts thereof may be used for animal feed or human consumption, or may be processed for food, feed or other purposes in any form of agriculture or industry. Agriculture shall mean to include horticulture, arboriculture, flower culture, and the like. Industries which may benefit from plant material according to the invention include but are not limited to the pharmaceutical industry, the paper and pulp manufacturing industry, sugar manufacturing industry, feed and food industry, enzyme manufacturers and the like.

The advantages of the plants, or parts thereof, according to the invention are the decreased need for pesticide treatment, thus lowering costs of material, labour, and environmental pollution, or prolonging shelf-life of products (e.g. fruit, seed, and the like) of such plants. Plants for the purpose of this invention shall mean multicellular organisms capable of photosynthesis, and subject to some form of pathogen induced disease. They shall at least include angiosperms as well as gymnosperms, monocotyledonous as well as dicotyledonous plants.

As is shown in the Examples, resistance can be obtained against a broad diversity of pathogens, ranging from viruses to bacteria, fungi and even insects.

One of the goals of the invention is to provide an enhanced pathogen resistance, while maintaining fitness and yield of the plants. It has been shown (see e.g. WO 04/007712) that introduction of an RKS receptor induced phenotypical changes in a plant. However, the changes that are induced by overexpression of RKS receptor molecules appear not to lower fitness and yield, but they appear to enhance fitness and yield. Thus, an additional advantage of inducing an enhanced pathogen resistance by providing a plant with a gene construct coding for a receptor which responds to a signalling compound, is that overexpression of such a receptor also increases yield and/or overall fitness of the plants.

Further, if such effects are less desired, it may be preferable, in order to maintain optimal fitness of the plants, to express the receptor molecules tissue specifically, i.e. only in those tissues which are (most) susceptible to pathogen infection. Of course, the choice of tissue also depends on the pathogen for which protection is sought: some of the pathogens will only infect e.g. the roots of the plant, while other pathogens are specific for the green parts or only the leaf or the stem. It will be understandable that expression of the receptor only in a limited part of the plant will not greatly harm the fitness of the plant, and in the meantime will be sufficient to give the plant an enhanced resistance against disease.

Although the transgenic plants, by themselves, will show an increased susceptibility to systemic signal compounds which will be produced by those same plants systemically on a basis level or in larger amounts after pathogen attack, it is part of the invention to induce an enhanced induced resistance by applying a systemic signal compound which is recognised by the receptor(s) or a ligand which is recognised by the chimaeric receptor(s) for which the plant is transgenic. Preferably the systemic signal compounds are applied by spraying. For most crop plants it is known when they are most vulnerable to pathogen infection, or when the pathogens, which use such plants as host, are most pathogenic. In order to optimally protect these plants against disease it is advisable to spray these plants at a time point, which allows the induced resistance to build up, before pathogen attack is expected.

In order to provide a quick and simple test if a new plant species indeed can yield an increased resistance upon spraying of a systemic signalling compound, a person skilled in the art can perform a rapid transient expression test known under the name of ATTA (*Agrobacterium tumefaciens* Transient expression Assay). In this assay (of which a detailed description can be found in Van den Ackerveken, G., et al. (Cell, 1996, 87, 1307-1316) the nucleotide sequence coding for the receptor of choice is placed under control of a plant constitutive promoter and introduced into an *Agrobacterium* strain which is also used in protocols for stable transformation. After incubation of the bacteria with acetosyringon or any other phenolic compound that is known to enhance *Agrobacterium* T-DNA transfer, 1 ml of the Agrobacterium culture is infiltrated in situ into a plant by injection after which the plants are placed in a greenhouse. After 2-5 days the leaves can be sprayed with the signalling compound and the following day they can be tested for pathogen resistance, either by applying a pathogen directly on the leaves, or by using the leaves in the well-known detached leaf assay. It is also possible to not actively spray with the signalling compound, but to use the plant's own signalling system to test for increased resistance of not directly affected plant parts.

An alternative test for detecting the level of resistance is by assaying for resistance markers, i.e. molecules that indicate an increased resistance to pathogens. Markers, which can be used in this respect, are PR-1, which is a marker for salicylic acid induction; At2g14560, which is a marker for brassinosteroid and salicylic acid induction, but not for auxin induction, and which is under direct transcriptional control of NPR1 (Plant Physiology 2005, 137, 1147-1159; Science 2005, 308, 1036-1040). The zinc finger protein ZAT7 (At3g46090); and At2g32200, encoding an extracellular peptide signalling molecule represent other markers for SAR-mediated resistance responses (see FIGS. 6, 9 and 10). Other genes with modified expression upon overexpression of RKS4 may also be used as marker. Abundance of these markers when compared to wild-type controls indicates an enhanced pathogen resistance in the plant.

The intracellular amounts of these markers are easy to determine with standard assays, which are well known to a person skilled in the art (see also Experimental part).

Ligand molecules or signal compounds, which would be applicable for spraying, are known to the person skilled in the art. Salicylic acid, jasmonic acid and brassinosteroids are compounds which are produced in bulk and which are readily available. The peptidergic GASA signal compounds which modify the activity of the RKS receptor have been described and can either be made synthetically or through recombinant DNA techniques well known in the art. The concentration of the compounds to be applied depends on the characteristics of the compound itself, the density of endogenous and transgenic receptors present in the plant tissue to be treated and the way in which the compound is to be applied (e.g. by spraying, through nutrient or water-uptake, etc.). For example, specifically designed brassinosteroids with optimised function, and antagonists of brassinosteroid signalling, interfering with normal binding of active brassinosteroids, could be further optimised based on molecular reporter systems based on detecting quantitatively and qualitatively the intracellular responses to brassinosteroid agonists and antagonists. Optimised detection of enhanced resistance responses could be determined in different genetic backgrounds of model plants, or in plants mutated for certain signalling pathways.

Activation of the GASA or systemin peptide ligands is possible by removing the N-terminal part of the pro-protein sequence. Active peptide products can be provided by either spraying active GASA and/or systemin protein, activation of the pro-proteins by extracellular proteases, or by providing the plant with inducible/tissue or stage-specific promoter constructs fused to the active peptide ligand sequences directly.

If it is considered to enhance the effect of providing plants with a larger amount of receptor molecules for the signalling compounds, a second construct coding for one or more of the downstream intermediates of such a processor could enlarge the resistance enhancing effects. Compounds which would qualify for this approach are either represented by gene products transmitting the signalling cascade downstream from the receptor, or gene products activated upon receptor activation. An example of direct signal transmission is provided by the NHL and the SPL gene products, which have been shown to interact directly as two-hybrid protein partners with RKS proteins. An example of genes controlled at the transcriptional level by this signalling cascade are represented by gene products involved in inducing resistance priming, like the previously described At2g14560, or alternatively At 4g14400 (an ankyrin repeat protein involved bringing different intracellular proteins together) and At4g23130 (a transmembrane receptor kinase).

EXAMPLES

Example 1

Cloning Strategies

Production and expression of receptors is performed for example through the Gateway™ cloning system. Overexpression constructs are made by the cloning of full length cDNA clones obtained from SALK, RIKEN or elsewhere as indicated by the *Arabidopsis* gene-mapping tool, e.g. by recombination cloning using vector sequences (M13 forward and reverse or T7 and SP6/T3 primers) and e.g. fusing them to the B1 and B2 recombination sites as used in the gateway cloning technology. Recombination into ectopic binary expression vectors is e.g. performed by gateway recombination. PCR amplification of the expression cassettes alone and subsequent particle bombardment using e.g. the T/R marker free transformation technology (WO 01/29240) might subsequently be performed for routine transformation of plant species with the desired gene product. A specific inducible system for expression may be performed in the same gateway cloning vector where inducible promoters like for example the Tween 20 inducible 1200 bp OPR1 promoter from *Arabidopsis thaliana* (Plant Mol Biol. 2001 November:47(5): 595-605) or tissue or stage inducible promoters like e.g. the early senescence 2000 bp CDPK1 (At1g18890) promoter (Mol Gen Genet. 1994, 244, 331-340) are used.

Chimaeric receptors might be constructed using RT-PCR production of the different receptor domains. Subsequent cloning (as described in Science, 2000, 288, 2360-2363) and expression of the resulting chimaeric receptors may again be performed using the gateway cloning and expression system.

Example 2

Application of Brassinosteroids Induces Resistance in Plants

Two *Arabidopsis* lines were used for the experiment; Ws-0, and Col-0. Nine-day old seedlings were sprayed with mock-Silwet L-77 (0.01%) or brassinosteroids (+0.01% Silwet L-77) After drying, the plants were incubated in the long day growth chamber (MPMI 2005, 18, 583-592). After two days half of the plants were sprayed on their leaves with Waco9 (50 spores/μL), a strain of *Peronospora parasitica* (MPMI 2005, 18, 583-592). Seven days post inoculation, the plants (40 seedlings per line) were scored for sporulation. The mock was used as a control. Experimental infections and analyses were performed as previously described (MPMI 2005, 18, 583-592).

Results (see FIG. 2 and Table 1) showed that, two days after spraying the mock and, Brassinosteroid mix, the plants sprayed with brassinosteroids were elongated but after six days they looked almost the same as the mock, only treated with 0.01% Silwett-L77 in water (just slightly more elongated. Also some of the cotyledons had turned upside-down. Col-0 and Ws-0 plants sprayed with brassinosteroids showed less sporulation of Waco9 compared to the mock control, thus indicating induction of resistance by the application of brassinosteroids.

TABLE I

| Waco9 6 day pi | mean/seedling | std |
|---|---|---|
| Col-0 MQ | 34.49 | 21.48 |
| Col-0 Bras | 19.75 | 9.93 |
| Ws-0 MQ | 71.44 | 28.03 |
| Ws-0 Bras | 46.89 | 21.01 |

Sporulation results

Example 3

RKS Receptors Mediate the Brassinosteroid Perception

Overexpression of RKS genes results in modified responses towards different concentrations of brassinosteroids in a root reponse bioassay (Cell 2002, 110 203-112 & 213-222). FIG. 3 shows that both RKS10-OX and RKS4-OX lines show an increased sensitivity to different concentrations of brassinosteroids. Knock out lines of RKS4, a gene which, in the root, is specifically expressed in the meristem initials of the stele and in provascular tissue, show on the other hand a strong decrease in brassinosteroid sensitivity as illustrated by longer roots at high concentration. This not only indicates that RKS4 is an important regulatory molecule during root growth, but that it also acts through Brassinosteroid signalling. RKS4 controls both the cell elongation and the cellular division rate in several plant organs (see FIG. 8). Its restricted expression in meristematic cells indicates an important function for the RKS4 gene product in growth, depending on receptor and hormone concentrations.

To study the function of RKS4 in detail both gain- and loss-of-function approaches were followed. The RKS4 full-length cDNA was ectopically expressed in *Arabidopsis* Ws-0 plants under the control of the CaMV 35S promoter and we looked for T-DNA insertion lines in the SALK collection (Alonso et al., 2003 available from NASC the European *Arabidopsis* seed-stock center). Two insertion lines, SALK__066568 and SALK__071166, renamed rks4-1 and rks4-2 respectively were studied along with overexpression lines (RKS4-OX). Changes in RKS4 steady state mRNA level were verified by RT-PCR in 12 d seedlings (FIG. 4), which showed that the RKS4 gene is indeed overexpressed in RKS4-OX plants and that its full-length messenger is no longer detectable in any of the two T-DNA insertion lines. Nevertheless the 5'end of the RKS4 mRNA (upstream of the T-DNA insertion) is still transcribed in both rks4-1 and rks4-2 KO lines. In rks4-1 the level of truncated messenger produced was higher than in all other samples. This fragment Corresponds to the extracellular domain of RKS4 receptor. The data from FIG. 4 show that the rks4-1 knock out line shows a strong elevated steady state level of the 5'mRNA compared with wild-type levels of RKS4 gene product. Both knock-out lines do not express the full length RKS4 mRNA any more. The results in FIG. 5 and the Q-PCR data from the reporters PR-1 and At2g14560 (FIGS. 9 and 10) show that this fragment has a positive effect on disease resistance against *Pseudomonas* and on the mRNA levels of resistance reporter gene products.

A similar N-terminal protein product, the tomato LRP protein (homologous of the ELS gene products very similar to the RKS extracellular domain) has been described previously as being associated with viroid infection. This LRP protein is processed during pathogenesis by subtilisins (Plant Journal 1996, 10, 315-330). These specific endoproteinases are involved in modulating the responses of the plant towards pathogen invasion by the specific modification of regulatory gene products within the cell wall. The resulting shifts in resistance as monitored indicate a role for the N-terminal domain of RKS-like gene products in the activation of the induced resistance within the plant as described below.

A number of RKS gene products have been shown to be involved in viral resistance, mediating resistance to a broad-spectrum of Geminiviruses (Genes and Development 2004, 18, 2545-2556). Herein the endogenous function of RKS 7, 14 and 1 has been studied with respect to their effect on viral infection. Successful plant infection proved to depend on the suppression of these RKS receptors by a viral virulence factor NSP. The NSP virulence protein interacts directly with the RKS protein, resulting in the suppression of antiviral responses (Virology 2004, 318, 24-31).

Our data are in agreement with a role of this subclass of RKS receptors since plants for which RKS4 expression has been modulated show an increased level of resistance. Ectopic expression of RKS4 in *Arabidopsis thaliana* does indeed result in an approximately 50% reduction of *Pseudomonas syringae* infection (FIG. 5). Interestingly, this level of resistance is further increased in the rks4-1 KO line (FIG. 5) in which the expression level of the 5' end of the messenger is increased (FIG. 4). This suggests an activation of the receptor by a proteolytic enzyme. These plants are also resistant to *Peronospora parasitica* (FIG. 5B), suggesting a general role for RKS gene products of at least this subgroup in mediating resistance against a variety of pathogens.

Example 4

RKS Genes Regulate Different Resistance Marker Genes

In RKS4 overexpressing plants the At2g14560 gene product, a marker for brassinosteroid induction but not for auxin induction, is upregulated (see FIGS. 9 and 10) The marker At2g14560 is under direct transcriptional control of NPR1, and is strongly induced by SA application (Plant Physiology 2005, 137, 1147-1159; Science 2005, 308, 1036-1040). These findings are in complete agreement with the observation that PR-1, together with other resistance markers, is strongly upregulated in plants with modified levels of RKS4 as compared to control plants (see FIGS. 6, 9 and 10).

We conclude from these results that brassinosteroid signalling mediated by RKS4 is inducing SA signalling responses within the plant as visualized by the strong upregulation of PR-1. Other highly induced resistance marker genes as the C2H2/ZAT7 (see FIG. 6), a transcriptional regulatory gene product (At3g46090) or the resistance-associated gene At2g32200 were respectively 160-fold and 100-fold induced in ectopic RKS4 expressing plants.

Example 5

RKS Induced Phenotypical Changes

Figure 7A:
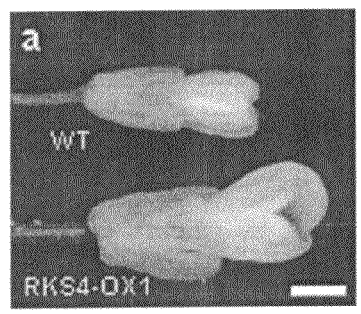
Figure 7B:
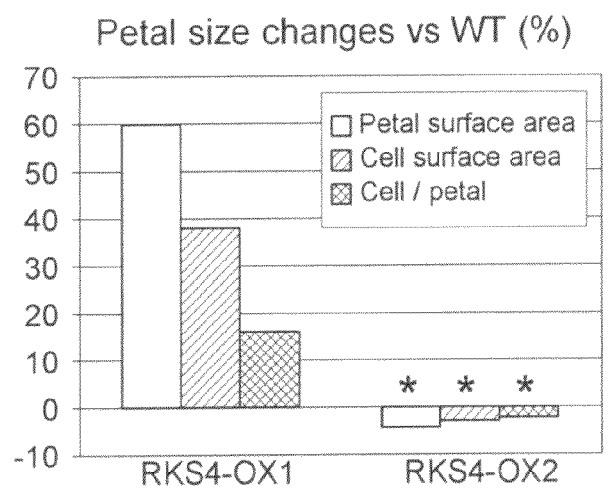
Figure 7C:
Figure 7D:
Figure 7E:
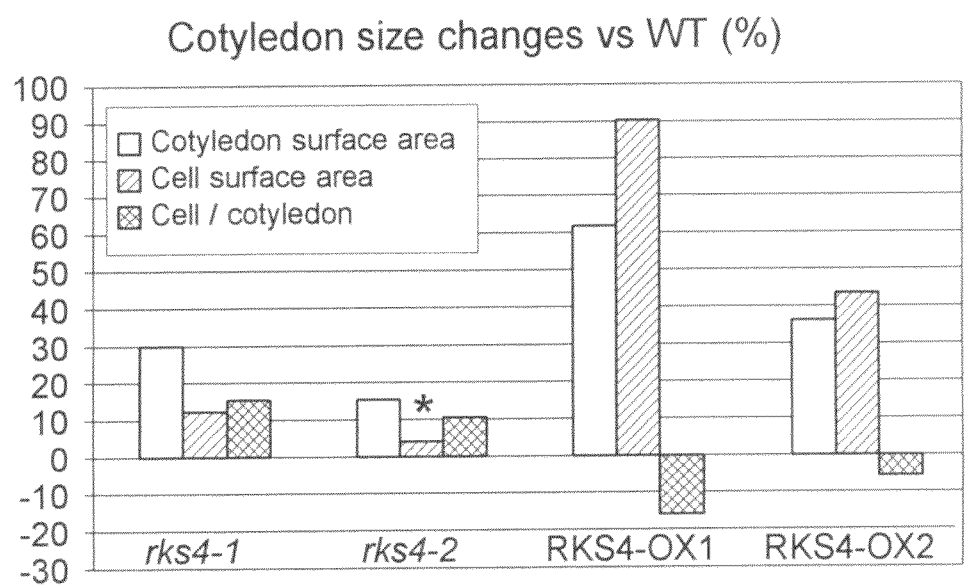
Figure 7F:
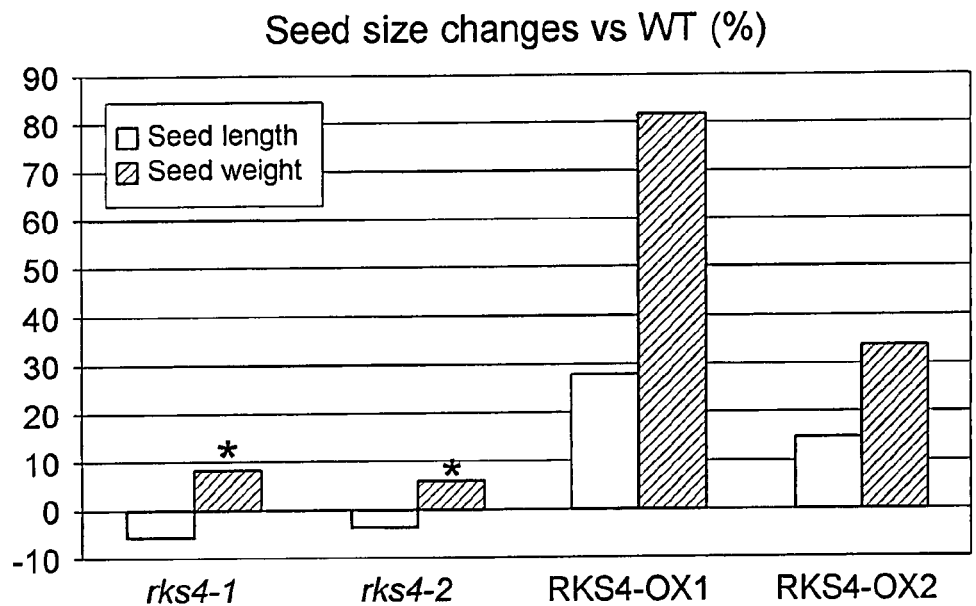
Figure 7G:
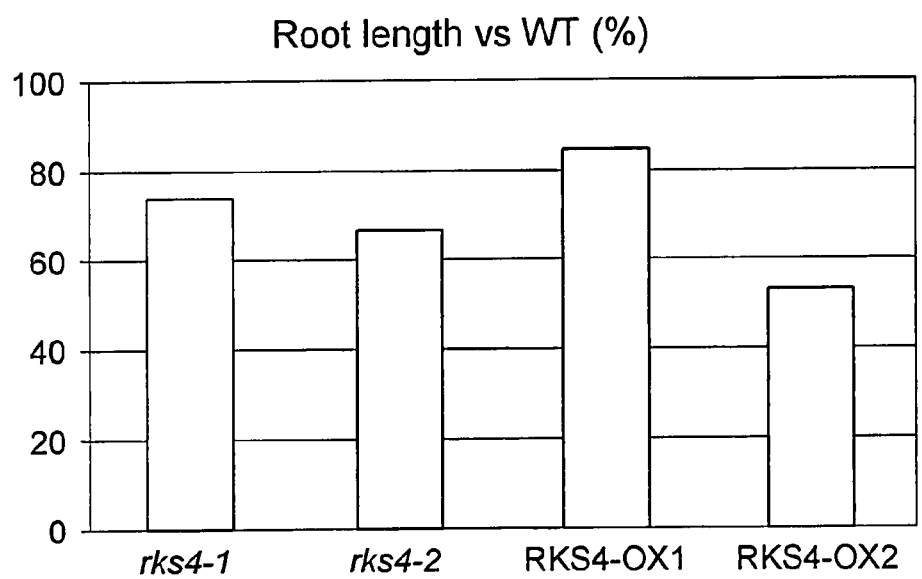
Figure 7H:
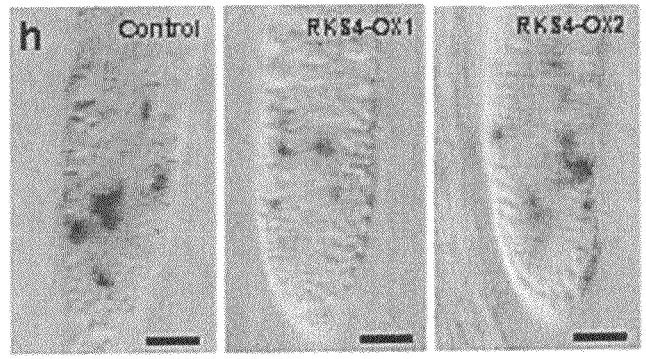
Figure 7I:
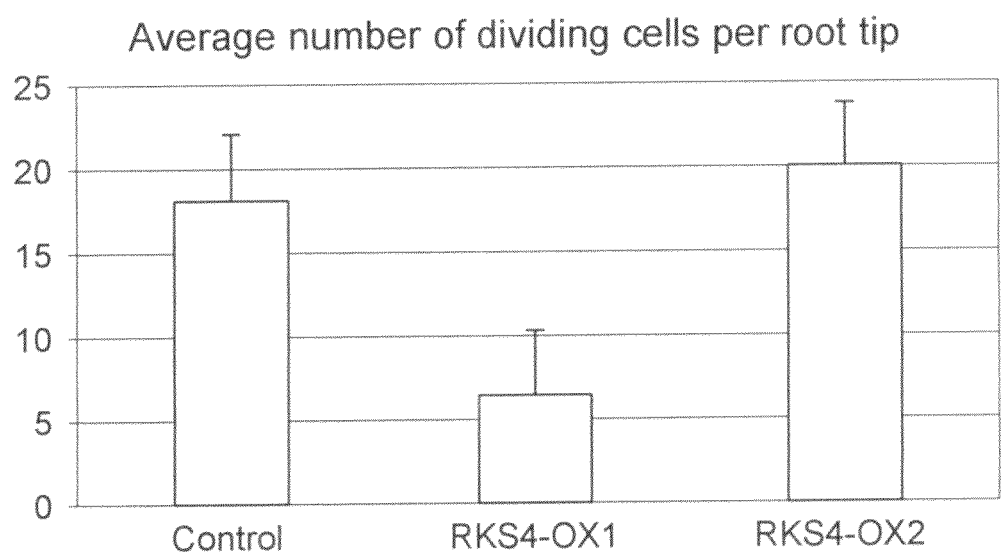

Observation of RKS4 overexpressing plants reveals a vide range of morphological changes; the most dramatic effects being found in flowers which size is drastically increased in RKS4-OX1 (FIG. 7a) but remains unaffected in RKS4-OX2 and KO plants (data not shown). Although we did not perform a quantitative analysis of all floral organs this size change could be at least correlated to an increased petal size. As a matter of fact it appeared that petal surface area in RKS4-OX1 was increased by 60% as compared to the wild-type (FIG. 7b). Measuring cell size clearly showed that this was, caused by both an increase in cell size (37.6%) and number (16.3%). No significant differences were observed however in the RKS4-OX2 (FIG. 7, p-value=0.09) or in the rks4 knock-out plants (data not shown). The latter is not surprising since the RKS4 gene is not expressed in petals. However the difference observed between the two overexpression lines is more puzzling and tends to suggest that the expression of RKS4 above a certain level might reverse the situation to wild-type. Altered expression of RKS4 did not affect silique shape and size (data not shown) as opposed to seed size (as already mentioned above) and weight (FIG. 7f). Seed size, as determined by its length, is indeed significantly reduced in the KO lines, although only by 5.2% and 3.5% for rks4-1 and -2, respectively. The opposite is observed in the overexpression lines that, as in flowers, show a strong length increase in RKS4-OX1 (27.6%) and a weaker one, although significant, in RKS4-OX2 (14.9%). In terms of seed weight the differences follow the same trend but are even more extreme with 81.9% and 33.7% heavier seeds for RKS4-OX1 and -OX2, respectively. The KO lines on the other hand show no significant difference. Notably the seed size/weight changes did not affect seed germination (data not shown). Changes in embryo size or endosperm content were not investigated, but cotyledon size was measured post-germination (FIG. 7e). Surprisingly, cotyledons were clearly larger both in the KO lines (30.1% for rks4-1 and 15.8% for rks4-2) as well as in the overexpression lines (61.7% and 36.9% for RKS4-OX1 and -OX2, respectively). Bigger cotyledons could account for larger embryos and hence an increase in seed weight and size as it is observed in RKS4-OX1 and -OX2. However this is not in agreement with rks4-1 and -2 seeds that are smaller than in the wild-type. Closer observation may explain this discrepancy. As a matter of fact cotyledons are larger in the KO lines mainly due to an increase in cell division (15% for rks4-1 and 10.7% for rks4-2). In the overexpression lines on the other hand cell division is actually decreased by 15.5% (RKS4-OX1) and 4.9% (RKS4-OX2) and larger cotyledons are therefore only the result of an extreme increase in cell elongation (plus 91.3% and 43.9%, respectively). Interestingly; cell elongation is increased as well in rks4-1 (13.1%) and contributes as well to the cotyledon size change but not in rks4-2 (p-value=0.38), showing, as in seeds, a difference in phenotypic strength. The large size increase observed in cotyledons of RKS4-OX1 was also visible later in the size and shape of its rosette leaves, especially under short day conditions, giving extremely robust rosettes with rounder and broader leaves (FIG. 7c-d). However, like in petals, this was not the case for RKS4-OX2 or the KO plants that showed no significant difference (data not shown). As expected from its expression pattern, altering RKS4 expression levels also affected root development. Measuring roots of seedlings grown on vertical plates did indeed reveal that, as in cotyledons, root size/length was significantly increased both in the KO and the overexpression lines (FIG. 7g). The situation as far as the extent of the increase is concern is even identical (compare FIG. 5e and g), with rks4-1 showing a stronger increase than rks4-2 (74% vs. 65.9%) and RKS4-OX1 showing the largest increase of all (83.7%) including RKS4-OX2 that is again less extreme with only 52.7%. To investigate the nature of this increase we made use of a mitotic activity marker described by Colon-Carmona et al. (1999), which was crossed in RKS4-OX lines (FIG. 7h). Quantitative analysis of the number of GUS-positive cells in root tips showed that cell division rate was dramatically reduced in RKS4-OX1, but was not significantly changed in RKS4-OX2 (FIG. 7i), which is more or less in agreement with the limited reduction (4.9%) observed in cotyledon size (FIG. 8e). In spite of the 3-fold reduction in cell division observed in RKS4-OX1, root length is still increased by 84% indicating that as in the cotyledons the size increase in roots is caused by a dramatic increase in cell elongation. In the KO lines however we have not yet been able to investigate whether the situation also corresponds to that observed in cotyledons, i.e. an increase in both cell elongation and division that would account for longer roots.

The sum of these observations is in accordance with the RKS4 promoter activity and suggests that the RKS4 receptor is involved in maintaining the size of the organs in which it is expressed. The fact that an increase and a decrease in its expression both can lead to larger organs (except in seeds) suggests a requirement for a specific level of RKS4 receptor at an optimum keeping organ size constant. Although loss of function of the receptor did not give rise to phenotypes as dramatic as its overexpression it is clear that in the RKS4 knockouts cell division is stimulated at least in cotyledons and maybe in roots as well whereas the opposite is observed in the same organs of overexpression plants, confirming that cell division could be repressed/maintained under a certain level by RKS4. This was not observed in petals on the other hand where overexpression of RKS4 stimulated cell division as well as elongation. However RKS4 is normally not expressed in petals and we might be looking at a pleiotropic effect due to an ectopic interaction that might not represent the endogenous function of the receptor. Interestingly in line RKS4-OX2 that shows a stronger expression of RKS4 the phenotypes observed are milder than in the other overexpression line or even absent like in petals. This probably indicates that a saturation level has been reached in the number of receptors produced leading to weaker effects.

The influence of light conditions on the observed phenotypes during vegetative growth and the known involvement of brassinosteroids in the modulation of photomorphogenis are in agreement with a role of RKS4, as in concordance with literature on RKS1.0 (BAK1/AtSERK3) in brassinosteroid (BR) signalling as also illustrated by the root growth assay described here above.

In conclusion, RKS gene products are involved in brassinosteroid perception. Modulation of these receptors results in elevated levels of resistance against different pathogens like *Pseudomonas* bacteria and viruses. Plants with modified levels of RKS show not only broad-spectrum disease resistance, but also show induced fitness characteristics.

Example 6

Insect Resistance

The analysis of transgenic *Arabidopis* plants for which the activity of RKS genes has been modulated revealed that improved resistance to a broad-spectrum of pathogens could be obtained. To investigate whether the resistance mechanism could be extended to insects preliminary experiments have been performed on RKS4 transgenic lines with Western Flower Thrips (WFT). Surprisingly these lines also proved to be less sensitive to thrips-caused damage.

Material and Methods

Seeds were germinated in 9 cm diameter Petri dishes on moist filter paper. For germination seeds were vernalised at 5° C. and 8 h light for 24 hours. When the cotyledons were fully developed the seedlings were transferred to 11 cm diameter pots filled with an equal mixture of dune sand and potting soil. Plants were grown in a growth chamber at 20° C. 70% relative humidity and 8 h light in a completely randomised design. When the majority of plants had a rosette diameter of 6-7 cm they were infested with the thrips *Frankliniella occidentalis* (Western Flower Thrips, FWT) for a choice test. In total 820 adult thrips were released in 14 groups of 50 and 2 groups of 60 thrips regularly distributed among plants. This was equivalent to 10 thrips per plant. The thrips originated from a thrips population cultivated on chrysanthemum flowers. For the non-choice test, each plant was placed in an individual thrips cage to which 10 adult thrips were added. Usually, thrips damage is scored after one generation of thrips, which is equivalent to three weeks. However, most plants developed flower stalks after two weeks, and thus plants were scored after 16 days (choice test) or 14 days (non-choice test). Silver damage as well as growth damage was measured in a double-blind manner for the whole plant. Data followed a normal distribution and were analysed by ANOVA with genotype and block as factors and silver damage as the dependent variable, followed by a post-hoc Tukey test to identify significantly different genotypes.

Results and Discussion

Choice Test

Thrips damage by *F. occidentalis* on *Arabidopsis* manifested itself in silver damage. Growth damage was almost absent. The total amount of silver damage among the *Arabidopsis* genotypes was significantly different (FIG. 11). RKS4-OX showed the least damage with an average score of 4. The amount of damage between the young and the old leaves did not differ within plants. All leaves showed the same extent of silver damage over all tested lines (t=1.23, df=80, p=0.22). In addition the RKS4 knockout line 1 showed significantly less silver damage than the corresponding wild-type plants, whereas this was less clear in KO2. This difference is in agreement with data obtained with other pathogens.

Non-Choice Test

In order to investigate whether plants with less damage were more resistant or less appealing to the insects, the experiment was repeated in a non-choice setting. Plants were put in individual cages and infested with thrips. This clearly showed that the results obtained with the RKS4 transgenic plants could be confirmed within different conditions (FIG. 12).

Both experiments show that modulating the activity of the RKS4 gene by for example overexpression of the full-length gene or if its N-terminus, as it occurs in the RKS4-KO1 plants, can increase resistance to several pathogens. Interestingly this also seems to apply to insects.

The invention claimed is:

1. A method for enhancing pathogen resistance in a plant by providing the plant with a gene construct comprising:
   (a) a DNA sequence coding for a Receptor Kinase-like SERK (RKS) receptor, wherein the RKS receptor is chosen from the group consisting of RKS0 (SEQ ID NO: 2), RKS1 (SEQ ID NO: 4), RKS2 (SEQ ID NO: 6), RKS3 (SEQ ID NO: 8), RKS4 (SEQ ID NO: 10), RKS5 (SEQ ID NO: 12), RKS6 (SEQ ID NO: 14), RKS7 (SEQ ID NO: 16), RKS8 (SEQ ID NO: 18), RKS10 (SEQ ID NO: 20), RKS11 (SEQ ID NO: 22), RKS12 (SEQ ID NO: 24), RKS13 (SEQ ID NO: 26), and RKS14 (SEQ ID NO: 28), or
   (b) a DNA sequence which is at least 95% identical with a DNA sequence coding for RKS0 (SEQ ID NO: 2), RKS1 (SEQ ID NO: 4), RKS2 (SEQ ID NO: 6), RKS3 (SEQ ID NO: 8), RKS4 (SEQ ID NO: 10), RKS5 (SEQ ID NO: 12), RKS6 (SEQ ID NO: 14), RKS7 (SEQ ID NO: 16), RKS8 (SEQ ID NO: 18), RKS10 (SEQ ID NO: 20), RKS11 (SEQ ID NO: RKS12 (SEQ ID NO: 24), RKS13 (SEQ ID NO: 26), or RKS14 (SEQ ID NO: 28), and wherein the DNA sequence has 4 or 5 leucine rich repeat motifs.

2. The method according to claim 1, wherein the DNA sequence coding for the receptor is under control of a tissue promoter or a regulatable promoter.

3. The method according to claim 2, wherein the regulatable promoter is inducible.

4. The method according to claim 1, wherein the RKS receptor consists of a receptor selected from the group consisting of RKS1 (SEQ ID NO: 4), RKS4 (SEQ ID NO: 10), RKS7 (SEQ ID NO: 16), RKS11 (SEQ ID NO: 22), and RKS14 (SEQ ID NO: 28).

5. A method for enhancing pathogen resistance in a plant by providing the plant a gene construct comprising a DNA sequence coding for the extracellular domain of a Receptor Kinase-like SERK (RKS) receptor,
wherein the RKS receptor is chosen from the group consisting of RKS0 (SEQ ID NO: 2), RKS1 (SEQ ID NO: 4), RKS2 (SEQ ID NO: 6), RKS3 (SEQ ID NO: 8), RKS4 (SEQ ID NO: 10), RKS5 (SEQ ID NO: 12), RKS6 (SEQ ID NO: 14), RKS7 (SEQ ID NO: 16), RKS8 (SEQ ID NO: 18), RKS10 (SEQ ID NO: 20), RKS11 (SEQ ID NO: 22), RKS12 (SEQ ID NO: 24), RKS13 (SEQ ID NO: 26), and RKS14 (SEQ ID NO: 28).

6. The method according to claim 5, wherein the extracellular domain is produced by truncating a RKS receptor or by applying an extracellular protease.

7. The method according to claim 6, wherein the act of applying is performed by external application.

8. The method according to claim 6, wherein said extracellular protease is a subtilisin.

9. The method according to claim 1, wherein the pathogen is selected from the group consisting of viruses, bacteria, fungi and insects.

10. A transgenic plant having a gene construct for enhancing pathogen resistance in the plant comprising a DNA sequence coding for a receptor,
   (a) wherein the receptor is Receptor Kinase-like SERK (RKS) receptor chosen from the group consisting of RKS0 (SEQ ID NO: 2), RKS1 (SEQ ID NO: 4), RKS2 (SEQ ID NO: 6), RKS3 (SEQ ID NO: 8), RKS4 (SEQ ID NO: 10), RKS5 (SEQ ID NO: 12), RKS6 (SEQ ID NO: 14), RKS7 (SEQ ID NO: 16), RKS8 (SEQ ID NO: 18), RKS10 (SEQ ID NO: 20), RKS11 (SEQ ID NO: 22), RKS12 (SEQ ID NO: 24), RKS13 (SEQ ID NO: 26), and RKS14 (SEQ ID NO: 28), or
   (b) a DNA sequence which is at least 95% identical with a DNA sequence coding for RKS0 (SEQ ID NO: 2), RKS1 (SEQ ID NO: 4), RKS2 (SEQ ID NO: 6), RKS3 (SEQ ID NO: 8), RKS4 (SEQ ID NO: 10), RKS5 (SEQ ID NO: 12), RKS6 (SEQ ID NO: 14), RKS7 (SEQ ID NO: 16), RKS8 (SEQ ID NO: 18), RKS10 (SEQ ID NO: 20), RKS11 (SEQ ID NO: RKS12 (SEQ ID NO: 24), RKS13 (SEQ ID NO: 26), or RKS14 (SEQ ID NO: 28), and wherein the DNA sequence has 4 or 5 leucine rich repeat motifs.

11. A transgenic plant having increased sensitivity for induced pathogen resistance comprising a stably transformed DNA sequence coding for a receptor for a systemic signal compound,
wherein the receptor is Receptor Kinase-like SERK (RKS) receptor chosen from the group consisting of RKS0 (SEQ ID NO: 2), RKS1 (SEQ ID NO: 4), RKS2 (SEQ ID NO: 6), RKS3 (SEQ ID NO: 8), RKS4 (SEQ ID NO: 10), RKS5 (SEQ ID NO: 12), RKS6 (SEQ ID NO: 14), RKS7 (SEQ ID NO: 16), RKS8 (SEQ ID NO: 18), RKS10 (SEQ ID NO: 20), RKS11 (SEQ ID NO: 22), RKS12 (SEQ ID NO: 24), RKS13 (SEQ ID NO: 26), and RKS14 (SEQ ID NO: 28), or
a DNA sequence which is at least 95% identical with a DNA sequence coding for RKS0 (SEQ ID NO: 2), RKS1 (SEQ ID NO: 4), RKS2 (SEQ ID NO: 6), RKS3 (SEQ ID NO: 8), RKS4 (SEQ ID NO: 10), RKS5 (SEQ ID NO: 12), RKS6 (SEQ ID NO: 14), RKS7 (SEQ ID NO: 16), RKS8 (SEQ ID NO: 18), RKS10 (SEQ ID NO: 20), RKS11 (SEQ ID NO: 22), RKS12 (SEQ ID NO: 24), RKS13 (SEQ ID NO: 26), or RKS14 (SEQ ID NO: 28), and wherein the DNA sequence has 4 or 5 leucine rich repeat motifs.

12. The method according to claim 1, wherein at least one motif is bordered by a domain containing a conserved pair of cystein residues in a disulphate bridge.

13. The method according to claim 10, wherein at least one motif is bordered by a domain containing a conserved pair of cystein residues in a disulphate bridge.

14. The method according to claim 11, wherein at least one motif is bordered by a domain containing a conserved pair of cystein residues in a disulphate bridge.

* * * * *

UNITED STATES PATENT AND TRADEMARK OFFICE
CERTIFICATE OF CORRECTION

PATENT NO. : 8,642,837 B2
APPLICATION NO. : 11/699401
DATED : February 4, 2014
INVENTOR(S) : de Boer et al.

It is certified that error appears in the above-identified patent and that said Letters Patent is hereby corrected as shown below:

IN THE SPECIFICATION:

Column 2, line 64:
  Now reads: "BMI1"
  Should read: -- BRI1 --

Column 3, line 47:
  Now reads: "Cell, 2002, no 213-222;"
  Should read: -- Cell, 2002, 110, 213-222; --

Column 3, line 55:
  Now reads: "CASA peptide"
  Should read: -- GASA peptide --

Column 6, line 67:
  Now reads: "50 spores/A;"
  Should read: -- 50 spores/µL; --

Column 7, line 18:
  Now reads: "2002, no 213-222)"
  Should read: -- 2002, 110, 213-222) --

Column 8, line 8:
  Now reads: "(b), (e), (0 and (g)"
  Should read: -- (b), (e), (f) and (g) --

Column 11, line 5:
  Now reads: "like GASH or systemin"
  Should read: -- like GASA or systemin --

Signed and Sealed this
Twelfth Day of August, 2014

Michelle K. Lee
*Deputy Director of the United States Patent and Trademark Office*

CERTIFICATE OF CORRECTION (continued)
U.S. Pat. No. 8,642,837 B2

IN THE SPECIFICATION (continued):

Column 20, line 46:
 Now reads: "consisting of complete repeats"
 Should read: -- consisting of 4 complete repeats --

Column 45, line 35:
 Now reads: "preferably inure than 95%"
 Should read: -- preferably more than 95% --

Column 45, line 38:
 Now reads: "3389.3402"
 Should read: -- 3389-3402 --

IN THE CLAIMS:

Claim 1, column 129, line 32:
 Now reads: "(SEQ ID NO:"
 Should read: -- (SEQ ID NO: 22) --

Claim 10, column 130, line 30:
 Now reads: "(SEQ ID NO:"
 Should read: -- (SEQ ID NO: 22) --